US008492532B2

(12) United States Patent
Morita et al.

(10) Patent No.: US 8,492,532 B2
(45) Date of Patent: Jul. 23, 2013

(54) ATTENUATED CHIMERIC FLAVIVIRUS BEARING ATTENUATED JAPANESE ENCEPHALITIS VIRUS GENE AS BACKBONE

(75) Inventors: Kouichi Morita, Nagasaki (JP); Takeshi Nabeshima, Nagasaki (JP); Shinichi Miyake, Kanonji (JP); Toshiyuki Onishi, Kanonji (JP); Isao Fuke, Kanonji (JP); Toyokazu Ishikawa, Kanonji (JP); Hideo Goda, Kanonji (JP); Masahide Ishibashi, Kanonji (JP); Michiaki Takahashi, Suita (JP)

(73) Assignee: The Research Foundation for Microbial Diseases of Osaka University, Osaka (JP)

( * ) Notice: Subject to any disclaimer, the term of this patent is extended or adjusted under 35 U.S.C. 154(b) by 664 days.

(21) Appl. No.: 12/292,518

(22) Filed: Nov. 20, 2008

(65) Prior Publication Data

US 2009/0104702 A1 Apr. 23, 2009

Related U.S. Application Data

(62) Division of application No. 11/793,277, filed as application No. PCT/JP2005/024161 on Dec. 22, 2005, now Pat. No. 7,749,734.

(30) Foreign Application Priority Data

Dec. 24, 2004 (JP) ................. 2004-374630

(51) Int. Cl.
*C12N 7/00* (2006.01)
*A61K 39/12* (2006.01)

(52) U.S. Cl.
USPC ............. 536/23.72; 435/69.1; 435/235.1; 424/218.1

(58) Field of Classification Search
None
See application file for complete search history.

(56) References Cited

U.S. PATENT DOCUMENTS

2004/0120964 A1 6/2004 Mikszta et al.

FOREIGN PATENT DOCUMENTS

| JP | 6-511150 | 12/1994 |
|---|---|---|
| JP | 2003-523189 | 8/2003 |
| WO | 93/06214 | 4/1993 |
| WO | 98/37911 | 9/1998 |
| WO | 01/39802 | 6/2001 |
| WO | 01/60847 | 8/2001 |
| WO | 01/60847 A2 | 8/2001 |
| WO | 01/60847 A3 | 8/2001 |
| WO | 2004/045529 | 6/2004 |

OTHER PUBLICATIONS

Monath et al., Journal of Virology, Feb. 2002, 76(4):1932-1943.*
Yoshida, I., et al., "Establishment of an Attenuated ML-17 Strain of Japanese Encephalitis Virus," Biken Journal, vol. 24, No. 1-2, 1981, pp. 47-67.
Pletnev, Alexander G., et al., "West Nile virus/dengue type 4 virus chimeras that are reduced in neurovirulence and peripheral virulence without loss of immunogenicity or protective efficacy," PNAS, vol. 99, No. 5, Mar. 5, 2002, pp. 3036-3041.
Ni, Haolin, "Molecular basis of attenuation of neurovirulence of wild-type Japanese encephalitis virus strain SA14," Journal of General Virology, 1995, vol. 76 (Pt. 2) pp. 409-413.
Aihara, Shinobu, "Identification of Mutations That Occurred on the Genome of Japanese Encephalitis Virus During the Attenuation Process," Virus Genes 5:2, 1991, pp. 95-109.
Arroyo, Juan, et al., "Molecular Basis for Attenuation of Neurovirulence of a Yellow Fever Virus/Japanese Encephalitis Virus Chimera Vaccine (ChiMeriVax-JE)," Journal of Virology, vol. 75, No. 2, Jan. 2001, pp. 934-942.
Guirakhoo, F., et al., "A Single Amino Acid Substitution in the Envelope Protein of Chimeric Yellow Fever-Dengue 1 Vaccine Virus Reduces Neurovirulence for Suckling Mice and Viremia/Viscerotropism for Monkeys," Journal of Virology, vol. 78, No. 18, Sep. 2004, pp. 9998-10008.
Supplementary European Search Report issued Jan. 30, 2009 in the European Application No. EP05822652.3.
Wu et al., "Phenotypic and Genotypic Characterization of the Neurovirulence and Neuroinvasiveness of a Large-Plaque Attenuated Japanese Encephalitis Virus Isolate," Microbes and Infection, vol. 5 (2003) pp. 475-480.
Indian Patent Office Communication issued Feb. 7, 2011 in Indian Patent Application No. 3239/CHENP/2007.
E. Mathenge et al., "Fusion PCR generated Japanese encephalitis virus/dengue 4 virus chimera exhibits lack of neuroinvasiveness, attenuated neurovirulence, and a dual-flavi immune response in mice", *Journal of General Virology* (2004), vol. 85, pp. 2503-2513.
P. Shah et al., "Molecular characterization of attenuated Japanese encephalitis live vaccine strain ML-17", *Vaccine* (2006), vol. 24, pp. 402-411.

* cited by examiner

*Primary Examiner* — Stacy B. Chen
(74) *Attorney, Agent, or Firm* — Wenderoth, Lind & Ponack, L.L.P.

(57) ABSTRACT

A nucleic acid molecule containing nucleotide sequences that encode the capsid protein, pre-membrane protein and non-structural protein of Japanese encephalitis virus, and a nucleotide sequence that encodes the envelop protein of a second flavivirus, wherein the nucleotide sequence(s) that encode(s) the pre-membrane protein and/or non-structural protein of Japanese encephalitis virus contain(s) nucleotide mutations that produce one or more amino acid mutations that attenuate the virus.

5 Claims, 4 Drawing Sheets

FIG. 1

| Gene | Nt. Position | Nt. JaOH0566 | Nt. ML-17 | AA Position | AA JaOH0566 | AA ML-17 |
|---|---|---|---|---|---|---|
| prM | 479 | G | A | 127 | M | I |
| M | 919 | A | C | 274 | N | T |
| E | 1139 | T | C | | | |
| | 2456 | C | T | | | |
| NS1 | 3254 | G | A | | | |
| NS2A | 3723 | G | T | 1209 | A | S |
| | 3845 | T | C | | | |
| | 4080 | T | C | | | |
| NS3 | 4997 | C | T | | | |
| | 5330 | A | G | | | |
| NS4B | 7319 | A | T | | | |
| | 7481 | T | C | | | |
| | 7484 | T | A | 2462 | N | K |
| | 7485 | G | A | 2463 | V | I |
| | 7533 | A | T | 2479 | T | S |
| NS5 | 8052 | C | A | 2652 | L | M |
| | 8072 | T | G | | | |
| | 8132 | A | G | | | |
| | 8273 | G | A | | | |
| | 8349 | C | G | 2751 | P | A |
| | 8351 | G | C | | | |
| | 8784 | A | G | 2896 | T | A |
| | 10237 | G | A | 3380 | S | N |
| 3' NTR | 10563 | G | A | | | |
| | 10804 | G | C | | | |

FIG. 2

| Gene | prM/M | | NS2A | NS4B | |
|---|---|---|---|---|---|
| AA Position | 127 | 274 | 1209 | 2462-3 | 2479 |
| ML-17 | IKLSN | ----LGSTNGQR--- | ---VAASFAE--- | AAFLVNPKITTVREAGVLVTAATLSLWNGAS--- |
| JaOH0566 | M** | N | *A** | ***NV********************T**** |
| JaOArS982 | M** | N | A | ***NV********************T**** |
| JaGAr01 | M** | N | A | ***NV********************T**** |
| Nakayama | M** | N | A | ***NV********************T**** |
| Beijing | M** | N | A | ***NV********************T**** |
| SA14 | M** | N | A | ***NV********************T**** |
| SA14-14-2 | M** | N | A | ***NV********************T**** |

| Gene | NS5 | | | |
|---|---|---|---|---|
| AA Position | 2652 | 2751 | 2896 | 3380 |
| ML-17 | VSMKSG---SGAAGNV---EPPAGAK---WCGNLIGTR--- |
| JaOH0566 | L | *P** | *T* | S**** |
| JaOArS982 | L | **** | **** | S**** |
| JaGAr01 | L | **** | **** | S**** |
| Nakayama | L | **** | **** | S**** |
| Beijing | L | **** | **** | S**** |
| SA14 | L | **** | **** | S**** |
| SA14-14-2 | L | **** | **** | S**** |

FIG. 4

5' CAP — C — prM — E — NS 1-5 — 3'

Primer 1A → Fragment 1A
Primer 2A → Fragment 2A
Primer 3A ← 
Primer 4A → Fragment 3A
Primer 1A → Fragment 2A
Primer 4A → Fragment 4A
Primer 5A → Fragment 3A
Primer 1A → Fragment 5A
Primer 6A ←
Primer 6A ← cDNA of ML-17/WN (E gene) having T7 promoter at 5' terminus

→ In vitro transcription, followed by transfection

ATTENUATED CHIMERIC FLAVIVIRUS BEARING ATTENUATED JAPANESE ENCEPHALITIS VIRUS GENE AS BACKBONE

This application is a divisional of Ser. No. 11/793,277, filed Jul. 27, 2007 now U.S. Pat. No. 7,749,734, which is a 371 U.S. national stage of International Application No. PCT/JP2005/024161 filed Dec. 22, 2005.

TECHNICAL FIELD

The present invention relates to an attenuated chimeric flavivirus having a gene of attenuated Japanese encephalitis virus as the backbone, which is useful as an attenuated live vaccine for preventing flavivirus infections.

BACKGROUND ART

Currently, more than about 60 kinds of viruses belonging to Flaviviridae (hereinafter abbreviated flaviviruses) are known, including Japanese encephalitis virus, West Nile virus, dengue 1-4 virus, yellow fever virus, St. Louis encephalitis virus, tick-borne encephalitis virus, Kunjin virus, Central European encephalitis virus, Kyasanur Forest virus, Murray Valley encephalitis virus, Omsk hemorrhagic fever virus, Powassan virus, Russian spring-summer encephalitis virus, Yokose virus, Apoi virus, and Aroa virus.

These flaviviruses have a genome of single-stranded (+) RNA and are similar to each other in terms of gene structure. The open reading frame (ORF) of the flavivirus genome encodes three structural proteins (capsid (C) protein, pre-membrane (prM) protein, which is the precursor for membrane (M) protein, and envelop (E) protein) and subsequent seven non-structural (NS) proteins (NS1, NS2A, NS2B, NS3, NS4A, NS4B, and NS5) from the 5' terminus thereof.

These structural proteins and non-structural proteins of the flaviviruses are translated as single polyproteins; the polyproteins translated are then processed by the protease and NS3 protein having protease activity of host cells and the virus, resulting in the formation of a mature virion comprising the above-described three kinds of structural proteins.

It is known that many of the above-described flaviviruses infect to mammals including humans, and birds, via insects such as mosquitoes and ticks, and cause encephalitis and/or febrile symptoms. Originally, each of these flavivirus species is indigenous to a particular region; therefore, the endemic area of the infection had been limited. However, in recent years, due to development in traffics/distributions, climate change and the like, various flavivirus infections have expanded to places other than the original habitats of causal flaviviruses, posing an important problem with public health.

In preventing the expansion of viral infections, prevention with vaccines is effective. However, despite the fact that a large number of viruses belonging to Flaviviridae have been recognized as described above, only attenuated live vaccines for yellow fever virus and Japanese encephalitis virus infections and inactivated vaccines for Japanese encephalitis virus and tick-borne encephalitis virus infections are in practical application as vaccines for flavivirus infections. Particularly, attenuated live vaccines are useful as vaccines that are inexpensive and induce long-term immunity, but there are no approved live vaccines other than those described above.

In these circumstances, as a means of quickly developing novel attenuated live vaccines for various flavivirus infections, a strategy utilizing a chimeric flavivirus prepared by a gene engineering technique has recently been drawing attention.

For example, ChimeriVax™-JE is a chimeric flavivirus prepared by replacing the genes that encode two structural proteins (prM-E) of the yellow fever virus vaccine 17D strain with the corresponding genes of the Japanese encephalitis virus vaccine SA14-14-2 strain (see, for example, pamphlet for International Patent Publication No. 98/37911 and pamphlet for International Patent Publication No. 01/39802). ChimeriVax™-JE is attenuated to the extent that allows its use as a vaccine as a result of a plurality of amino acid mutations from the wild type that are present in the virus polyprotein corresponding to the E protein of the Japanese encephalitis virus vaccine SA14-14-2 strain (see, for example, Arroyo et al., J. Virol. 75:934-942, 2001).

Furthermore, on the basis of this technique for ChimeriVax™-JE, chimeric flaviviruses with dengue 1-4 viruses (ChimeriVax™-DEN (1-4)) (see, for example, pamphlet for International Patent Publication No. 98/37911 and pamphlet for International Patent Publication No. 01/39802) and a chimeric flavivirus with West Nile virus (ChimeriVax™-West Nile) (see, for example, pamphlet for International Patent Publication No. 2004/045529), which have a gene of the yellow fever virus vaccine 17D strain as the backbone, have also been developed.

These chimeric flaviviruses are also attenuated to the extent that allows their use as vaccines, with their attenuation resulting mainly from amino acid substitutions from the wild type that are present in the virus polyprotein corresponding to the prM-E protein.

However, it has been reported that the attenuation of ChimeriVax™-DEN1 results mainly from amino acid mutations in the E protein that occur during the passage of this chimeric flavivirus in cells for vaccine production (see, for example, Guirakhoo et al., J. Virol. 78:9998-10008, 2004). Furthermore, because re-infection with dengue viruses of different serotypes is likely as a cause of the onset of dengue hemorrhagic fever, this vaccine has not found a practical application.

Also, ChimeriVax™-West Nile has the attenuation promoted by artificially introducing an amino acid mutation in the E protein derived from the wild-type highly virulent West Nile virus NY-99 strain (see, for example, pamphlet for International Patent Publication No. 2004/045529).

As a chimeric flavivirus using a gene backbone other than yellow fever virus (YF-17D), a chimeric flavivirus prepared by replacing the gene that encodes the prM-E protein of dengue-4 virus with the corresponding gene of the West Nile virus NY99 strain (WN/DEN4 chimeric virus) has been reported (see, for example, Pletnev et al., Proc. Natl. Acad. Sci. USA 99:3036-3041, 2002).

Although the WN/DEN4 chimeric virus is attenuated compared to the parent strains thereof, i.e., West Nile virus and dengue-4 virus, the mechanism of the attenuation has not yet been fully elucidated, and the virus has not found a practical application as a vaccine.

DISCLOSURE OF THE INVENTION

When attenuated live chimeric flavivirus vaccines for various flavivirus infections is developed by conventional methods as described above, it is necessary to investigate the safety, that is, brain neurotoxicity, infectivity from peripheral to the central nervous system (brain nerve invasiveness), infection-preventing effect, neutralizing antibody production and the like of the chimeric virus constructed for each combination of flavivirus species, and this may be a major cause of prolonging the period to the practical application of attenuated live vaccine.

Furthermore, live vaccines still pose the problem of reductions in antibody productivity as they are attenuated for the sake of safety. This is because attenuation of viruses by modifying the E protein as described above potentially reduces their immune induction potential (antibody productivity) as vaccines because the antigenic determinant for inducing a neutralizing antibody is present in the E protein.

Accordingly, it is an object of the present invention to provide an attenuated chimeric flavivirus having an attenuating mutation in a portion other than the E protein.

The present inventors diligently investigated to solve the above-described problem, found that the Japanese encephalitis virus vaccine ML-17 strain for swine had a plurality of amino acid mutations intrinsic to the ML-17 strain in the prM and NS proteins other than the E protein, and obtained the suggestion that these amino acid mutations might be involved in the attenuation of the ML-17 strain. Based on this finding, the present inventors were inspired to construct a chimeric flavivirus having the structural and non-structural proteins other than the E protein (that is, C protein, prM protein, and NS protein) of a Japanese encephalitis virus comprising one or more of the amino acid mutations intrinsic to the ML-17 strain, conducted further investigations, and developed the present invention.

Accordingly, the present invention provides:

[1] A nucleic acid molecule comprising nucleotide sequences that encode the capsid protein, pre-membrane protein and non-structural protein of Japanese encephalitis virus, and a nucleotide sequence that encodes the envelop protein of a second flavivirus,
wherein the nucleotide sequence(s) that encode(s) the pre-membrane protein and/or non-structural protein of Japanese encephalitis virus comprise(s) nucleotide mutations that produce one or more amino acid mutations that attenuate the virus.
[2] The nucleic acid molecule described in [1], wherein the Japanese encephalitis virus is the ML-17 strain.
[3] The nucleic acid molecule described in [1] or [2], wherein the second flavivirus is selected from the group consisting of West Nile virus, dengue 1-4 virus, yellow fever virus, St. Louis encephalitis virus, tick-borne encephalitis virus, Kunjin virus, Central European encephalitis virus, Kyasanur Forest virus, Murray Valley encephalitis virus, Omsk hemorrhagic fever virus, Powassan virus, Russian spring-summer encephalitis virus, Yokose virus, Apoi virus, and Aroa virus.
[4] An attenuated chimeric flavivirus encoded by the nucleic acid molecule described in any one of [1] to [3].
[5] An attenuated live vaccine comprising the attenuated chimeric flavivirus described in [4].
[6] A method of preparing the nucleic acid molecule described in [1], which comprises the following steps:
a step for replacing a nucleotide sequence that encodes the envelop protein in a nucleic acid molecule comprising a nucleotide sequence that encodes Japanese encephalitis virus with the nucleotide sequence that encodes the envelop protein of the second flavivirus; and
a step for introducing nucleotide mutations that produce one or more amino acid mutations that attenuate the virus into the nucleotide sequence(s) that encode(s) the pre-membrane protein and/or non-structural protein of Japanese encephalitis virus.
[7] A method of preparing the nucleic acid molecule described in [1], which comprises the following step:
a step for replacing a nucleotide sequence that encodes the envelop protein in a nucleic acid molecule comprising a nucleotide sequence that encodes a Japanese encephalitis virus having one or more amino acid mutations that attenuate the virus in the pre-membrane protein and/or non-structural protein with the nucleotide sequence that encodes the envelop protein of the second flavivirus.
[8] A method of preparing an attenuated chimeric flavivirus, which comprises a step for expressing chimeric flavivirus proteins from the nucleic acid molecule described in any one of [1] to [3].
[9] A nucleic acid molecule comprising a nucleotide sequence that encodes a Japanese encephalitis virus having one or more amino acid mutations that attenuate the virus in the pre-membrane protein and/or non-structural protein.
[10] A vector comprising the nucleic acid molecule described in [9].
[11] An attenuated Japanese encephalitis virus encoded by the nucleic acid molecule described in [9].
[12] A method of preparing the nucleic acid molecule described in [9], which comprises a step for introducing nucleotide mutations that produce one or more amino acid mutations that attenuate the virus into nucleotide sequence(s) that encode(s) the pre-membrane protein and/or non-structural protein in a nucleic acid molecule comprising a nucleotide sequence that encodes Japanese encephalitis virus.
[13] A method of preparing an attenuated Japanese encephalitis virus, which comprises a step for expressing Japanese encephalitis virus proteins from the nucleic acid molecule described in [9].

By the present invention, an attenuated chimeric flavivirus having attenuating mutation(s) in portion(s) other than the E protein is provided. Because the attenuation of the chimeric flavivirus of the present invention can be achieved without modifying the E protein, attenuated live vaccines for various flavivirus infections can be brought into practical application in a short time, without reducing the immune induction potential.

BRIEF DESCRIPTION OF THE DRAWINGS

FIG. 1 shows the differences in the nucleotide sequence of genomic cDNA and the amino acid sequence of polyprotein between the Japanese encephalitis virus L-17 strain and JaOH0566 strain. Nt represents nucleotide; AA represents amino acid. Amino acid positions are shown by number, as counted from the amino acid next to the starting methionine of the polyprotein.

FIG. 2 shows the results of a comparison of amino acids that have mutated from the parent strain (JaOH0566 strain) (indicated by bold letters) in the polyprotein of the Japanese encephalitis virus ML-17 strain, with the corresponding amino acids in the polyproteins of the JaOH0566 strain, JaOArS982 strain, JaGAr01 strain, Nakayama strain, Beijing strain, SA14 strain, and SA14-14-2 strain. Amino acid positions are shown by number, as counted from the amino acid next to the starting methionine of the polyprotein. * represents that the amino acid at the indicated position is the same as that of the ML-17 strain. The amino acid sequences specified in the top row of the upper table of FIG. 2, starting from the left most column correspond to amino acids 128-132, 272-279, 1207-1213 and 2456-2487 of SEQ ID NO: 2. The amino acids specified in the top row of the lower table of FIG. 2, starting from the left most column correspond to amino acids 2651-2656, 2750-2756, 2894-2900 and 3378-3386 of SEQ ID NO: 2.

FIG. 4 shows an outline of the method of preparing the cDNA of the ML-17/WN (E gene) chimeric flavivirus by the Long-PCR method.

BEST MODE FOR EMBODYING THE INVENTION

Figure 3:
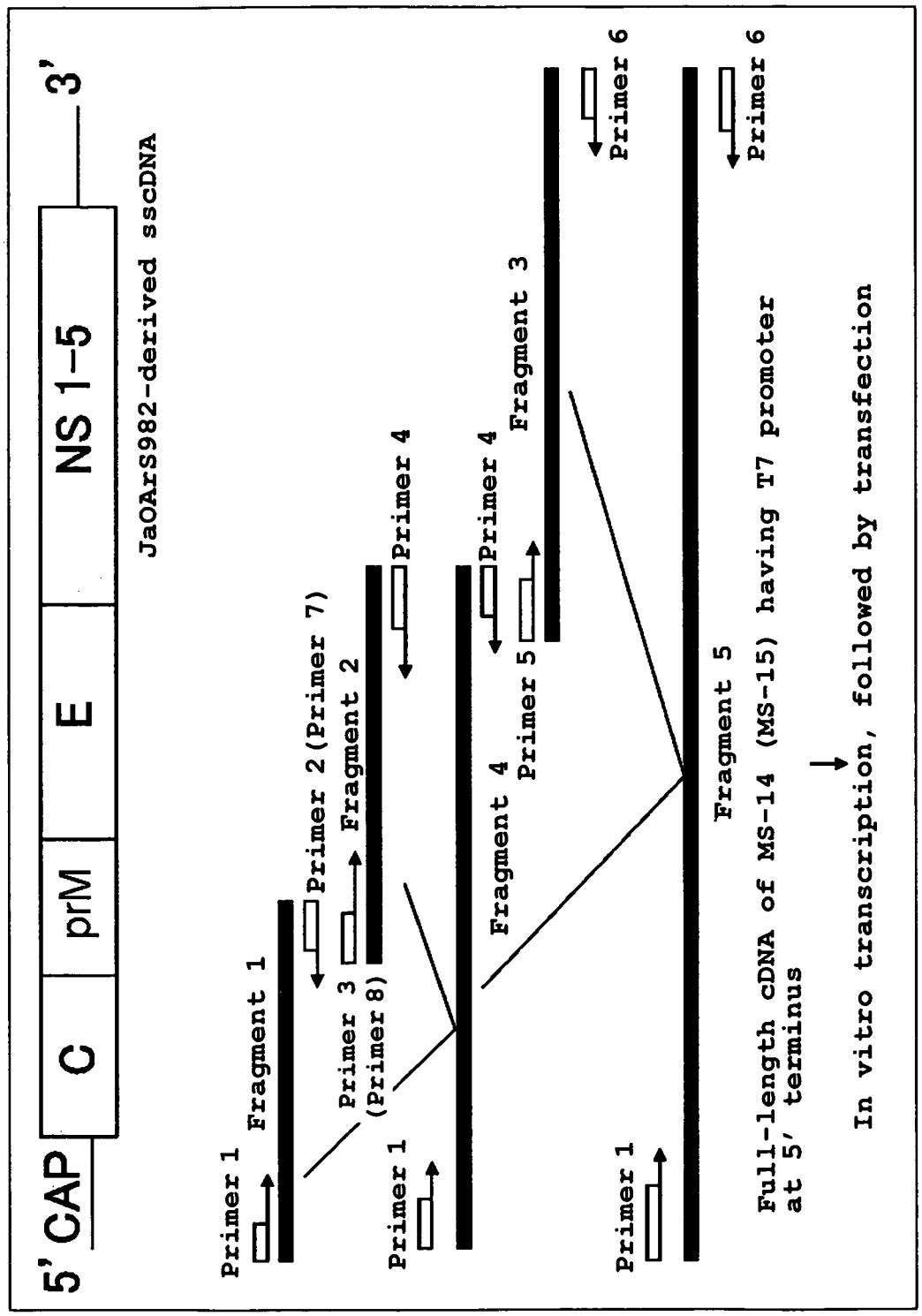
FIG. 3 shows an outline of the method of preparing the full-length cDNA of the recombinant Japanese encephalitis virus MS-14 strain and MS-15 strain by the Long-PCR method.

The present invention provides a nucleic acid molecule comprising nucleotide sequences that encode the C protein, prM protein and NS protein of Japanese encephalitis virus (a first flavivirus), and a nucleotide sequence that encodes the E protein of a second flavivirus. Preferably, the present invention provides a nucleic acid molecule comprising a nucleotide sequence of the 5' untranslated region, the nucleotide sequences that encode the C protein, prM protein and NS protein, and a nucleotide sequence of the 3' untranslated region of Japanese encephalitis virus, and the nucleotide sequence that encodes the E protein of the second flavivirus. Furthermore, this nucleic acid molecule comprises nucleotide mutations that produce one or more amino acid mutations capable of attenuating the virus as described below, in the nucleotide sequence(s) that encode(s) the prM protein and/or NS protein of Japanese encephalitis virus.

The present invention also provides a chimeric flavivirus encoded by such a nucleic acid molecule.

In this specification, "a nucleic acid molecule" means a single-stranded or double-stranded DNA or RNA.

In this specification, "a nucleotide sequence" means a sequence of deoxyribonucleotide (shown by A, G, C, and T) or a sequence of ribonucleotide (shown by A, G, C, and U) unless otherwise specified.

In this specification, the left end represents the 5' terminus and the right end represents the 3' terminus for a single-stranded nucleotide sequence; the left end represents the N terminus (amino terminus) and the right end represents the C terminus (carboxyl terminus) for an amino acid sequence unless otherwise specified.

In this specification, amino acids are shown using 1-letter abbreviation or 3-letter abbreviation in the standard denotation system for amino acids unless otherwise specified.

In this specification, "attenuated" means that a virus is low virulent (low toxic) such that the virus can be used safely as a vaccine for an animal subject to vaccination {for example, human and non-human mammals (for example, monkeys, horses, cattle, sheep, swine, dogs, cats, rabbits, rats, mice and the like), and birds and the like}.

In this specification, "the virus can be used (safely) as a vaccine" means that growth of the virus is observed at the site of inoculation of the vaccine but ends without manifesting serious symptoms, and that specific immunity is conferred which prevents the onset of a disease caused by a highly virulent virus inoculated in a subsequent challenge test with the virus against an individual inoculated with the vaccine.

Japanese encephalitis virus used as a first flavivirus to prepare the chimeric flavivirus of the present invention is not subject to limitation, as long as the prM protein and/or NS protein of the chimeric flavivirus of the present invention finally comprises one or more amino acid mutations that attenuate the virus as described below.

Therefore, any strain may be used out of the various strains of Japanese encephalitis virus (for example, ML-17 strain, JaOH0566 strain, JaOArS982 strain, JaGAr01 strain, Nakayama strain, Beijing strain, SA14 strain, SA14-14-2 strain and the like).

The genomes of various Japanese encephalitis virus strains have been cloned, and the complete or partial nucleotide sequences thereof have been determined. See, for example, Sumiyoshi et al., Virology 161:497-510, 1987 for the JaOArS982 strain; McAda et al., Virology 158:348-360, 1987 for the Nakayama strain; Hashimoto et al., Virus Genes 1:305-317, 1988 for the Beijing strain; Nitayaphan et al., Virology 177:541-552, 1990 for the SA14 strain and SA14-14-2 strain.

Information on the genome sequences of various Japanese encephalitis viruses can also be obtained from publicly accessible gene databases such as GenBank. See, for example, GenBank accession number: M18370 for the JaOArS982 strain; GenBank accession number: AF069076 for the JaGAr01 strain; GenBank accession number: L48961 for the Beijing-1 strain; GenBank accession number: M55506 for the SA14 strain; GenBank accession number: AF315119 for the SA14-14-2 strain.

To prepare a nucleic acid molecule comprising a nucleotide sequence that encodes the chimeric virus of the present invention, a nucleic acid molecule comprising a nucleotide sequence that encodes Japanese encephalitis virus is prepared, and can be used as the gene backbone for chimeric flavivirus. As examples of the nucleic acid molecule comprising a nucleotide sequence that encodes Japanese encephalitis virus, genomic RNA, cDNA, synthetic RNA, synthetic DNA and the like can be mentioned.

Alternatively, to prepare a nucleic acid molecule comprising a nucleotide sequence that encodes the chimeric flavivirus of the present invention, any fragment (for example, PCR-amplified DNA fragment and the like) of a nucleic acid molecule comprising a nucleotide sequence that encodes Japanese encephalitis virus can be used.

The genomic RNA of Japanese encephalitis virus can be prepared by a commonly known method from cells (for example, MMC-LK2 cells, HeLa cells, N2a cells, PS cells, BSC-1 cells, HL-CZ cells, LLC-MK2 cells, Vero cells, BHK cells, mosquito-derived C6/36 cells, mouse- or hamster-derived intracerebral cells), growing chicken eggs and the like infected with Japanese encephalitis virus. Japanese encephalitis virus strain used to prepare a genomic RNA is not subject to limitation; for example, the strains as listed above can be used.

A cDNA of Japanese encephalitis virus can be constructed from a genomic RNA according to a commonly known method (for example, the method described in Sumiyoshi et al., Virology 161:497-510, 1987).

Alternatively, a genomic RNA or cDNA of Japanese encephalitis virus or any fragment thereof can also be chemically synthesized on the basis of genome sequence information on Japanese encephalitis virus by a commonly known method.

The genomic RNA or cDNA of Japanese encephalitis virus or any fragment thereof can be amplified with a genomic RNA or cDNA as the template by Polymerase Chain Reaction (abbreviated as "PCR method"), Reverse Transcriptase-Polymerase Chain Reaction (abbreviated as "RT-PCR method"), Long Polymerase Chain Reaction (abbreviated as "Long-PCR method"), and/or Long-Reverse Transcriptase-Polymerase Chain Reaction (abbreviated as "Long-RT-PCR method").

Alternatively, a genomic RNA or cDNA of Japanese encephalitis virus or any fragment thereof can also be inserted to a vector and cloned.

As examples of the vector used, plasmids such as pBR322, pBR325, pBR327, pBR328, pUC7, pUC8, pUC9, pCU18, pUC19, pHSG298, pHSG299, pSC101, pGBM5, and pCRII can be mentioned. As the cloning vector, bacteriophage, cosmid, phagemid and the like can also be used. These cloning vectors are commercially available from, for example, NIPPON GENE CO., LTD. and the like.

As the second flavivirus used in the present invention, a flavivirus other than Japanese encephalitis virus, for example, West Nile virus, denguel-4 virus, yellow fever virus, St. Louis encephalitis virus, tick-borne encephalitis virus, Kunjin virus, Central European encephalitis virus, Kyasanur Forest virus, Murray Valley encephalitis virus, Omsk hemorrhagic fever virus, Powassan virus, Russian spring-summer encephalitis virus, Yokose virus, Apoi virus, Aroa virus and the like can be mentioned. For these flavivirus species as well, any strain may be used out of the various mutant strains thereof.

Nucleotide sequences and amino acid sequences that encode the E proteins of various flaviviruses as described above are commonly known, and furthermore, for many of these flavivirus species, the entire nucleotide sequence of the genome thereof has been reported. See, for example, the following: West Nile virus (for example, Wengler et al., Virology 147:264-274, 1985); dengue-1 virus (for example, Mason et al., Virology 161:262-267, 1987); dengue-2 virus (for example, Deubel et al., Virology 155:365-377, 1986; Gruenberg et al., J. Gen. Virol. 69:1391-1398, 1988; Hahn et al., Virology 162:167-180, 1988); dengue-3 virus (for example, Osatomi et al., Virus Genes 2:99-108, 1988); dengue-4 virus (for example, Mackow et al., Virology 159:217-228, 1987; Zhao et al., Virology 155:77-88, 1986); yellow fever virus (for example, Rice et al., Science 229:726-733, 1985); St. Louis encephalitis virus (for example, Trent et al., Virology 156:293-304, 1987); tick-borne encephalitis virus (for example, Mandl et al., Virology 166:197-205, 1988); Kunjin virus (for example, Coia et al., J. Gen. Virol. 69 (Pt 1):1-21, 1988); Kyasanur Forest virus (for example, Venugopal et al., Journal of General Virology 75:227-232, 1994; Kuno et al., Journal of Virology 72:73-83, 1998); Murray Valley encephalitis virus (for example, Dalgarno et al., J. Mol. Biol. 187:309-323, 1986); Omsk hemorrhagic fever virus (for example, Lin et al., Virology 313:81-90, 2003; Li et al., Journal of General Virology 85:1619-1624, 2004; Gritsun et al., Journal of General Virology 74:287-291, 1993); Powassan virus (for example, Kuno et al., Am. J. Trop. Med. Hyg. 65:671-676, 2001; Mandl et al., Virology 194:173-184, 1993); Russian spring-summer encephalitis virus (for example, Kuno et al., Journal of Virology 72:73-83, 1998); Apoi virus (for example, Billoir et al., Journal of General Virology 81:781-790, 2000); Aroa virus (for example, Gaunt et al., Journal of General Virology 82:1867-1976, 2001).

Information on the nucleotide sequences of the genomes of various flaviviruses can also be obtained from publicly accessible gene databases such as GenBank. See, for example, the following: West Nile virus (for example, GenBank accession number: M12294; NC_001563); dengue-1 virus (for example, GenBank accession number: M23027); dengue-2 virus (for example, GenBank accession number: M19197; NC_001474); dengue-3 virus (for example, GenBank accession number: M93130); dengue-4 virus (for example, GenBank accession number: M14931); yellow fever virus (for example, GenBank accession number: X03700; NC_002031); St. Louis encephalitis virus (for example, GenBank accession number: M16614); tick-borne encephalitis virus (for example, GenBank accession number: U27495; NC_001672); Kunjin virus (for example, GenBank accession number: AY274504; AY274505); Kyasanur Forest virus (for example, GenBank accession number: X74111); Murray Valley encephalitis virus (for example, GenBank accession number: AF161266; NC_000943); Omsk hemorrhagic fever virus (for example, GenBank accession number: AY193805; AY438626; X66694; NC_005062); Powassan virus (for example, GenBank accession number: AF310922; AF310920; AF310912; L06436; NC_003687); Yokose virus (for example, GenBank accession number: AB114858; NC_005039); Apoi virus (for example, GenBank accession number: AF160193; NC_003676); Aroa virus (for example, GenBank accession number: AF372413).

To prepare a nucleic acid molecule comprising a nucleotide sequence that encodes the chimeric virus of the present invention, a nucleic acid molecule comprising a nucleotide sequence that encodes a second flavivirus is prepared, and a region that encodes the E protein thereof can be used. As examples of the nucleic acid molecule comprising a nucleotide sequence that encodes a second flavivirus, genomic RNA, cDNA, synthetic RNA, synthetic DNA and the like can be mentioned.

Alternatively, to prepare a nucleic acid molecule comprising a nucleotide sequence that encodes the chimeric flavivirus of the present invention, any fragment (for example, PCR-amplified DNA fragment and the like) of a nucleic acid molecule comprising a nucleotide sequence that encodes a second flavivirus can be used.

The genomic RNA of a second flavivirus can be prepared by the same method as that for Japanese encephalitis virus.

A cDNA of a second flavivirus can also be constructed from a genomic RNA by the same technique as that for Japanese encephalitis virus.

Alternatively, a genomic RNA or cDNA of a second flavivirus or any fragment thereof can also be chemically synthesized on the basis of commonly known genome sequence information on the virus used as the second flavivirus, by a commonly known method.

The genomic RNA or cDNA of a second flavivirus or any fragment thereof can be amplified by the PCR method, RT-PCR method, Long-PCR method and/or Long-RT-PCR method, with a genomic RNA or cDNA as the template, as in Japanese encephalitis virus.

Alternatively, a genomic RNA or cDNA of a second flavivirus or any fragment thereof can also be inserted to an appropriate vector as listed above and cloned, as in Japanese encephalitis virus.

A nucleic acid molecule (DNA or RNA) comprising a nucleotide sequence that encodes the chimeric flavivirus of the present invention is prepared by replacing a nucleotide sequence that encodes the E protein in a nucleic acid molecule comprising a nucleotide sequence that encodes Japanese encephalitis virus with a nucleotide sequence that encodes the envelop protein of a second flavivirus.

Replacement of the region that encodes the E protein in a nucleic acid molecule comprising a nucleotide sequence that encodes Japanese encephalitis virus can be performed by a commonly known recombinant technology (for example, the method utilizing the Long-PCR method described in Morita et al., Virology 287:417-426, 2001, and the like).

Alternatively, a nucleic acid molecule (DNA or RNA) comprising a nucleotide sequence that encodes the chimeric flavivirus of the present invention can also be prepared by chemical synthesis by designing the entire nucleotide sequence that encodes the chimeric flavivirus of the present invention, on the basis of genome sequence information on Japanese encephalitis virus and a second flavivirus.

When a nucleic acid molecule comprising a nucleotide sequence that encodes the chimeric flavivirus of the present invention is prepared as DNA, a promoter sequence for in vitro transcription is introduced to the 5' terminus of the DNA. The DNA that encodes the chimeric flavivirus of the present invention is transcribed to RNA by an RNA polymerase corresponding to the promoter introduced, at any stage prior to expression of the chimeric flavivirus protein. As examples of the promoter sequence used, the T7 RNA polymerase promoter, SP6 RNA polymerase promoter and the like can be mentioned.

The RNA that encodes the chimeric flavivirus of the present invention is introduced by a commonly known gene introduction technology in the art such as transfection, electroporation, or microinjection, into cells suitable for protein expression (for example, C6/36 cells, Vero cells, BHK cells, MMC-LK2 cells, HeLa cells, N2a cells, PS cells and the like), and the chimeric flavivirus protein is expressed in these cells.

Alternatively, for the chimeric flavivirus of the present invention, the chimeric flavivirus protein can be obtained by utilizing a method of protein production not using a cell system, wherein a genetic information translation system for the organism is provided in a test tube by the addition of a substrate, enzyme and the like to cell homogenate or extract (also referred to as cell-free system expression; see, for example, U.S. Pat. No. 5,478,730; Madin et al., Proc. Natl. Acad. Sci. USA 97:559-564, 2000; Sawasaki et al., Proc. Natl. Acad. Sci. USA 99:14652-14657, 2002).

The nucleic acid molecule comprising a nucleotide sequence that encodes the chimeric flavivirus of the present invention comprises a nucleotide mutation that produces one or more amino acid mutations that attenuate the virus in the nucleotide sequence that encodes the prM protein and/or NS protein derived from Japanese encephalitis virus in this nucleic acid molecule.

In detail, when expressed with the amino acid sequences of the individual structural proteins and non-structural proteins of the Japanese encephalitis virus JaOArS982 strain (see H. Sumiyoshi et al., Virology 161:497-510, 1987) as a reference, the amino acid mutations that attenuate the virus are the following amino acid substitutions: substitution of the 1st methionine of the prM protein by isoleucine; substitution of the 148th asparagine of the prM protein (56th of M protein) by threonine; substitution of the 4th alanine of the NS2A protein by serine; substitution of the 51st asparagine of the NS4B protein by lysine; substitution of the 52nd valine of the NS4B protein by isoleucine; substitution of the 68th threonine of the NS4B protein by serine; substitution of the 126th leucine of the NS5 protein by methionine; and/or substitution of the 854th serine of the NS5 protein by asparagine.

Alternatively, the above-described amino acid substitutions can also be performed using conservative amino acids for the amino acids introduced at the respective amino acid positions.

In this specification, "conservative amino acids" mean amino acids similar to each other in terms of physicochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met).

Preferably, the chimeric flavivirus of the present invention comprises at least substitution of the 1st methionine of the prM protein by isoleucine and/or substitution of the 148th asparagine of the prM protein (56th of M protein) by threonine, out of the above-described amino acid substitutions.

The above-described amino acid mutations can be introduced in any step for preparing a nucleic acid molecule comprising a nucleotide sequence that encodes the chimeric flavivirus of the present invention.

Introduction of the above-described amino acid mutations can be performed using, for example, the site-directed mutagenesis method utilizing the Long-PCR method, described in Morita et al., Virology 287:417-426, 2001, or by applying a commonly known method such as the Kunkel method or the gapped duplex method or a mutagenesis kit utilizing these methods (available from, for example, Takara Bio Inc.) and the like to a cDNA cloned to plasmid.

Alternatively, these mutations can be introduced to the chimeric flavivirus of the present invention by using a nucleic acid molecule comprising a nucleotide sequence that encodes a Japanese encephalitis virus having one or more amino acid mutations that attenuate the virus in the prM and/or NS protein to prepare a nucleic acid molecule comprising a nucleotide sequence that encodes the chimeric flavivirus of the present invention.

A nucleic acid molecule comprising a nucleotide sequence that encodes a Japanese encephalitis virus having one or more amino acid mutations that attenuate the virus in the prM and/or NS protein can be prepared by artificially introducing these mutations to a genomic RNA or cDNA of a Japanese encephalitis virus strain not containing these mutations (for example, JaOH0566 strain, JaOArS982 strain, JaGAr01 strain, Nakayama strain, Beijing strain, SA14 strain, SA14-14-2 strain and the like), using the aforementioned commonly known method of site-directed mutagenesis.

A recombinant Japanese encephalitis virus can be prepared by expressing a virus protein from the nucleic acid molecule comprising a nucleotide sequence that encodes a Japanese encephalitis virus having one or more amino acid mutations that attenuate the virus in the prM and/or NS protein, thus artificially prepared, by a commonly known method as described above.

By infecting this recombinant Japanese encephalitis virus to suitable cells as described above, and culturing the cells, a large amount of genomic RNA can be prepared from the cultured cells.

Furthermore, this recombinant Japanese encephalitis virus is an attenuated Japanese encephalitis virus per se, and can be a promising candidate for an attenuated live vaccine for Japanese encephalitis.

A nucleic acid molecule comprising a nucleotide sequence that encodes a Japanese encephalitis virus having one or more amino acid mutations that attenuate the virus in the prM and/or NS protein can also be prepared by acquiring a genomic RNA or cDNA from a Japanese encephalitis virus mutant strain natively comprising one or more such amino acid mutations.

As examples of the Japanese encephalitis virus mutant strain natively comprising one or more amino acid mutations that attenuate the virus in the prM and/or NS protein, the Japanese encephalitis virus ML-17 strain can be mentioned. The ML-17 strain is a Japanese encephalitis virus vaccine strain for swine (see, for example, Yoshida et al., BIKEN JOURNAL 24:47-67, 1981), and is available from The Research Foundation for Microbial Diseases of Osaka University (based in Osaka University, 3-1, Yamadaoka, Suita-shi, Osaka).

Alternatively, from among mutant strains of Japanese encephalitis virus resulting from passage in cells and the like, a strain having one or more amino acid mutations that attenuate the virus in the prM and/or NS protein may be selected by a commonly known method, and a genomic RNA or cDNA thereof can also be used to prepare the chimeric flavivirus of the present invention.

The nucleic acid molecule (genomic RNA or cDNA) comprising a nucleotide sequence that encodes a Japanese encephalitis virus having one or more amino acid mutations that attenuate the virus in the prM and/or NS protein, thus prepared, may be inserted to a cloning vector as described above after being fragmented as required. For example, utilizing such a recombinant vector, the chimeric flavivirus of the present invention can be prepared safely and conveniently.

Construction of the chimeric flavivirus of the present invention can be confirmed by, for example, acquiring the gene from the chimeric virus prepared, determining all or a portion of the base sequence thereof or corresponding amino acid sequence (for example, the portion where the mutation has been introduced, the joint of the two viruses and the like), and confirming that the sequence matches with the intended sequence.

The present invention also provides an attenuated live vaccine comprising the chimeric flavivirus of the present invention (hereinafter also referred to as the vaccine of the present invention). Because the E protein of virus contains an antigenic determinant that induces a neutralizing antibody, inoculation of the chimeric flavivirus of the present invention as a vaccine results in the production of an antibody against the second flavivirus species used as the E protein.

To prevent various flavivirus infections, the vaccine of the present invention can be inoculated to, for example, animals such as humans and non-human mammals (for example, monkeys, horses, cattle, sheep, swine, dogs, cats, rabbits, rats, mice and the like), and birds.

The vaccine of the present invention can be produced in the form of a suspension or freeze-dried preparation. The vaccine of the present invention can comprise, in addition to the chimeric flavivirus of the present invention, a pharmaceutically acceptable stabilizer (for example, sucrose, lactose, glucose, gelatin, gelatin hydrolysates, sodium L-glutamate, serum albumin and the like), soothing agent (for example, glucose and the like) and the like in common use in vaccine preparations.

Upon vaccination, the vaccine of the present invention can normally be dissolved or suspended in a pharmaceutically acceptable carrier. As examples of the carrier, liquid carriers such as water, saline (including physiological saline), and buffer solutions (for example, phosphate buffer solution) can be mentioned.

The vaccine of the present invention is representatively prescribed as a sterile aqueous solution containing $10^2$ to $10^6$ PFU of the chimeric flavivirus of the present invention per a dose of 0.1 to 1.0 ml, and can be inoculated, for example, subcutaneously, intradermally, intramuscularly and the like.

Alternatively, because some flaviviruses are known to infect via the mucosa, the vaccine of the present invention may be administered orally or transnasally according to the second flavivirus species chosen.

Furthermore, a nucleic acid molecule (RNA or DNA) comprising a nucleotide sequence that encodes the chimeric flavivirus of the present invention per se can also be used as a nucleic acid vaccine preparation.

Confirmation of the efficacy and safety of the chimeric virus constructed can be performed by, for example, evaluating brain neurotoxicity, infectivity from peripheral to the central nervous system (brain nerve invasiveness), infection-preventing effect, presence or absence of viremia, neutralizing antibody production and the like in animals (for example, mice, monkeys and the like) by a commonly known method of evaluation in the art.

The present invention is hereinafter described in more detail by means of the following Examples, which, however, are for illustrative purposes only and never limit the scope of the invention.

EXAMPLES

Example 1

Determination of Attenuating Mutation Sites of the Japanese Encephalitis Virus Vaccine ML-17 Strain To determine the attenuating mutation sites of the Japanese encephalitis virus vaccine ML-17 strain, first, the nucleotide sequence of full-length genomic cDNA and the amino acid sequence of polyprotein were compared between the ML-17 strain and its parent strain, i.e., the wild-type virulent Japanese encephalitis virus JaOH0566 strain.

The nucleotide sequence of full-length genomic cDNA of the ML-17 strain (obtained from The Research Foundation for Microbial Diseases of Osaka University) (SEQ ID NO:1) and the nucleotide sequence of full-length genomic cDNA of the JaOH0566 strain (SEQ ID NO:3) were determined according to the method disclosed in Sumiyoshi et al., Virology 161:497-510, 1987. For both strains, the cDNAs were constructed using the PCR primers shown in Table 1A, and the nucleotide sequences of the cDNAs constructed were determined using the primers for sequencing shown in Table 1B. Furthermore, the amino acid sequence of the polyprotein of the ML-17 strain (SEQ ID NO:2) and the amino acid sequence of the polyprotein of the JaOH0566 strain (SEQ ID NO:4) were deduced from the nucleotide sequences of the respective full-length genomic cDNAs.

TABLE 1A

Japanese encephalitis virus (JEV) PCR primers

| Name of primer | Corresponding nucleotide position on the genome* | Nucleotide sequence |
|---|---|---|
| JEV 1-34F | 1-34-F | AGAAGTTTATCTGTGTGAACTTCTTG GCTTAGTA (SEQ ID NO:5) |
| JEV 2851-2817R | 2851-2817-R | GCAAAGAGAATGCTTTTTCCCCATGC TTTCCAGCC (SEQ ID NO:6) |
| JEV 2707-2741F | 2707-2741-F | TCCTGCTCAAAGAGAATGCAGTGGAC CTCAGTGTG (SEQ ID NO:7) |
| JEV 5554-5520R | 5554-5520-R | GTCATGAAGATGGCTGCTGCCTCCCC TAATTCCAC (SEQ ID NO:8) |
| JEV 5414-5449F | 5414-5449-F | ACTGATGTCACCGAACAGAGTGCCCA ACTACAACCT (SEQ ID NO:9) |
| JEV 8257-8223R | 8257-8223-R | TTTTCTATAACCTTGGGCATGTAAGG GCAGAGAAC (SEQ ID NO:10) |
| JEV 8119-8153F | 8119-8153-F | GGGAATCCTCTCCAAGTCCAGAAGTA GAAGAACAA (SEQ ID NO:11) |
| JEV 10976-10943R | 10976-10943-R | AGATCCTGTGTTCTTCCTCACCACCA GCTACATA (SEQ ID NO:12) |

TABLE 1B

Primers for Japanese encephalitis virus (JEV) sequencing

| Name of primer | Corresponding nucleotide position on the genome* | Nucleotide sequence |
|---|---|---|
| JEV 1-20F | 1-20-F | AGAAGTTTATCTGTGTGAAC (SEQ ID NO:13) |
| JEV 421-440F | 421-440-F | AAGGCTCAATCATGTGGCTC (SEQ ID NO:14) |
| JEV 821-840F | 821-840-F | GAAAGCCACACGGTATCTCA (SEQ ID NO:15) |
| JEV 1174-1193F | 1174-1193-F | CTGACATCTCGACGGTGGCT (SEQ ID NO:16) |
| JEV 1559-1578F | 1559-1578-F | TGGACTGAACACTGAAGCGT (SEQ ID NO:17) |
| JEV 1942-1961F | 1942-1961-F | TTGTCATTGAACTATCCTAC (SEQ ID NO:18) |
| JEV 2326-2345F | 2326-2345-F | GAACACTCTTTGGGGGAATG (SEQ ID NO:19) |
| JEV 2520-2539F | 2520-2539-F | TGTGGAAGTGGCATCTTTGT (SEQ ID NO:20) |
| JEV 2746-2765F | 2746-2765-F | TGAACAAGCCCGTGGGAAGA (SEQ ID NO:21) |
| JEV 3147-3166F | 3147-3166-F | ACTTGGCCAGAGACACACAC (SEQ ID NO:22) |
| JEV 3538-3557F | 3538-3557-F | ATGGTGAAATGGTTGACCCT (SEQ ID NO:23) |
| JEV 3935-3954F | 3935-3954-F | AGCATGGATGATTGTCCGAG (SEQ ID NO:24) |
| JEV 4111-4130F | 4111-4130-F | AGAAAGGAGCTGTACTCTTG (SEQ ID NO:25) |
| JEV 4339-4358F | 4339-4358-F | CCTACGTGGTGTCAGGAAAA (SEQ ID NO:26) |
| JEV 4741-4760F | 4741-4760-F | TTTTCCACACACTATGGCAC (SEQ ID NO:27) |
| JEV 5112-5131F | 5112-5131-F | GACCGTCAGGAGGAACCAGT (SEQ ID NO:28) |
| JEV 5517-5535F | 5517-5535-F | AAGGTGGAATTAGGGGAGG (SEQ ID NO:29) |
| JEV 5914-5932F | 5914-5932-F | AAGAGGGAGAAGGCAGAGT (SEQ ID NO:30) |
| JEV 6319-6338F | 6319-6338-F | ATGCCATACTGGAGGACAAC (SEQ ID NO:31) |
| JEV 6685-6704F | 6685-6704-F | GAAAGGGTATAGGGAAGATG (SEQ ID NO:32) |
| JEV 7106-7125F | 7106-7125-F | CACCACATCGCTAGCCTCAA (SEQ ID NO:33) |
| JEV 7508-7527F | 7508-7527-F | GGTATTGGTGACGGCGGCTA (SEQ ID NO:34) |
| JEV 7920-7939F | 7920-7939-F | TGTGGGCGTGGAGGATGGAG (SEQ ID NO:35) |
| JEV 8292-8311F | 8292-8311-F | CTAGTGCGTCTCCCCCTGTC (SEQ ID NO:36) |
| JEV 8713-8732F | 8713-8732-F | CTGACACCACCCCTTTTGGA (SEQ ID NO:37) |
| JEV 9144-9162F | 9144-9162-F | GCTTTGGGGTTCCTGAATG (SEQ ID NO:38) |
| JEV 9470-9488F | 9470-9488-F | AGAAGATCAAAGGGGGAGT (SEQ ID NO:39) |
| JEV 9870-9889F | 9870-9889-F | CCGTGCAGAGGACAGGATGA (SEQ ID NO:40) |
| JEV 10281-10298F | 10281-10298-F | TATGCGGCGATAAACCAG (SEQ ID NO:41) |
| JEV 10662-10679F | 10662-10679-F | GCGCAGCCCCAGGAGGAC (SEQ ID NO:42) |
| JEV 375-356R | 375-356-R | CGTCAATGAGTGTTCCAAGT (SEQ ID NO:43) |
| JEV 3084-3065R | 3084-3065-R | CAATCCAGTACGACAAGTCA (SEQ ID NO:44) |
| JEV 5757-5738R | 5757-5738-R | TGACCTTTTTCCCGGCTCTT (SEQ ID NO:45) |
| JEV 8518-8499R | 8518-8499-R | TTCTTGATTTTCTCCTGATT (SEQ ID NO:46) |
| JEV 10976-10955R | 10976-10955-R | AGATCCTGTGTTCTTCCTCACC (SEQ ID NO:47) |

*: F represents a forward primer; R represents a reverse primer.

As a result of a comparison of the nucleotide sequences of the genomic cDNAs, it was found, as shown in FIG. 1, that the ML-17 strain had 25 nucleotide substitutions, with 10 amino acid substitutions produced due to 10 of these nucleotide substitutions, at the 127th, 274th, 1209th, 2462nd, 2463rd 2479th, 2652nd, 2751st, 2896th, and 3380th amino acids, as counted from the amino acid next to the starting methionine of the polyprotein.

Furthermore, the above-described amino acid mutations in the polyprotein of the ML-17 strain were compared with the amino acid sequences of the corresponding sites of the polyproteins of the JaOArS982 strain, JaGAr01 strain, Nakayama strain, Beijing strain, and SA14 strain, which are other wild-type virulent Japanese encephalitis viruses, and the SA14-14-2 strain, which is another Japanese encephalitis virus vaccine.

The putative amino acid sequences of the polyproteins of the following strains were obtained from GenBank and used in this Example:

Amino acid sequence of the polyprotein of the JaOArS982 strain (GenBank accession number: M18370);
Amino acid sequence of the polyprotein of the JaGAr01 strain (GenBank accession number: AF069076);
Amino acid sequence of the polyprotein of the Beijing-1 strain (GenBank accession number: L48961);
Amino acid sequence of the polyprotein of the SA14 strain (GenBank accession number: M55506);
Amino acid sequence of the polyprotein of the SA14-14-2 strain (GenBank accession number: AF315119).

For the amino acid sequence of the polyprotein of the Nakayama strain, the amino acid sequence of the region necessary for the comparison was obtained from the gene and/or amino acid partial sequence information described in GenBank accession number: AF112297; McAda et al., Virology. 158(2):348-60, 1987 and the like, and used in this Example.

As shown in FIG. 2, as a result of a comparison of the amino acid sequences of the polyproteins, a total of eight amino acid substitutions at the 127th, 274th, 1209th, 2462nd, 2463rd, 2479th, 2652nd, and 3380th amino acid positions, as counted from the amino acid next to the starting methionine of the polyprotein, out of the above-described 10 amino acid substitutions between the ML-17 strain and the JaOH0566 strain, were found to be amino acid mutations intrinsic to the ML-17 strain.

From a comparison with the positions in the individual structural proteins and non-structural proteins in the polyprotein of the Japanese encephalitis virus (JaOArS982 strain) described in Sumiyoshi et al., Virology 161:497-510, 1987, it was found that the positions of these eight amino acid substitutions in the polyprotein corresponded to the 1st and 148th amino acids of the prM protein (56th of M protein); the 4th amino acid of the NS2A protein; the 51st, 52nd, and 68th amino acids of the NS4B protein; and the 126th and 854th amino acids of the NS5 protein, respectively.

Example 2

Preparation of Recombinant Japanese Encephalitis Virus MS-14 Strain and MS-15 Strain To confirm the effects of amino acid mutations intrinsic to the ML-17 strain on the attenuation of the virus, according to the site-directed mutagenesis method utilizing the Long-PCR method, described in Morita et al., Virology 287:417-426, 2001, using the gene of the wild-type virulent Japanese encephalitis virus JaOArS982 strain as the backbone, MS-14 strain, which is a recombinant Japanese encephalitis virus incorporating a nucleotide mutation that produces substitution of the 1st methionine of the prM protein by isoleucine (substitution of G by A at position 479 of the genome), and MS-15 strain, which is a recombinant Japanese encephalitis virus incorporating a nucleotide mutation that produces substitution of the 148th asparagine of the prM protein (56th of the M protein) by threonine (substitution of A by C at position 919 of the genome), were prepared.

(Preparation of the MS-14 Strain)

As shown in FIG. 3, with the gene RNA of Japanese encephalitis virus (JaOArS982 strain) as the template, using a set of primer 1 and primer 2, a set of primer 3 and primer 4, and a set of primer 5 and primer 6, by the Long-RT-PCR method, Japanese encephalitis virus gene fragments corresponding to the respective primer sets (fragments 1, 2, and 3) were prepared.

Furthermore, after each fragment was purified by agarose electrophoresis, first, with fragments 1 and 2 as the templates, using a set of primers 1 and 4, again by the Long-PCR method, gene fragment 4 was prepared. This gene fragment was purified in the same manner; next, with gene fragments 3 and 4 as the templates, using a set of primers 1 and 6, the Long-PCR method was performed to prepare a full-length Japanese encephalitis virus cDNA having the T7 promoter sequence at the 5' terminus thereof (fragment 5).

With this full-length Japanese encephalitis virus cDNA (fragment 5) as the template, an in vitro RNA synthesis reaction was performed to prepare an artificial full-length Japanese encephalitis virus gene RNA. This RNA was introduced into mosquito cells (C6/36 cells) by the electroporation method and the cells were cultured for 5 days, after which the recombinant virus (MS-14 strain) emerging in the culture supernatant was recovered.

(Preparation of the MS-15 Strain)

For the MS-15 strain, the recombinant virus was recovered according to the above-described method except that the recombinant virus was prepared using primer 7 instead of primer 2, and primer 8 instead of primer 3.

Furthermore, for control, a mutation-free virus was acquired using primer 9 instead of primer 2, and primer 10 instead of primer 3.

The primers used in this Example are shown in Table 2.

| Name of primer | Corresponding nucleotide position on the genome* | Nucleotide sequence* |
|---|---|---|
| primer 1 | T7 promoter-1-45-S | AAATTTAATACGACTCACTATAAGAAG TTTATCTGTGTGAACTTCTTGGCTTAG TATCGTTG (SEQ ID NO:48) |
| primer 9 | 972-927-R | AAGCCGGAGCGACCAACAGCAGGAGGA TGGTAAATACCACGCGTTG (SEQ ID NO:56) |
| primer 10 | 927-972-S | CAACGCGTGGTATTTACCATCCTCCTG CTGTTGGTCGCTCCGGCTT (SEQ ID NO:57) |
| primer 4 | 2670-2626-R | GCTCCAATCTAGTGACAGATCTGACTC CGCACACGCCTTCCTTGT (SEQ ID NO:51) |
| primer 5 | 2501-2547-S | CACAAGAAAAGAGATGAGATGTGGAAG TGGCATCTTTGTGCACAACG (SEQ ID NO:52) |
| primer 6 | 10976-10937-R | AGATCCTGTGTTCTTCCTCACCACCAG CTACATACTTCGG (SEQ ID NO:53) |
| primer 3 | 439-484/5-S (479G→A) | CGCAAGCTTGGCAGTTGTCATAGCTTA CGCAGGAGCAATAA_A_GTTG (SEQ ID NO:50) |
| primer 2 | 471-515-R (479G→A) | CGTCATCAAAAGCTTCCCCTGGAAATT CGACAACTT_T_ATTGCTCC (SEQ ID NO:49) |
| primer 8 | 882-926-5 (919A→C) | TTCCTGGCGGCGACACTTGGCTGGATG CTTGGCAGTA_CC_AACGGT (SEQ ID NO:55) |
| primer 7 | 900-944 -R (919A→C) | GGTAAATACCACGCGTTGACCGTTG_G_T ACTGCCAACCATCCAGCC (SEQ ID NO:54) |

In the table above, S represents a sense sequence; R represents a complementary sequence. The underline represents the T7 promoter sequence; the double underline represents a nucleotide mutation.

Example 3

Evaluation of the Growing Potentials of the Recombinant Japanese Encephalitis Virus MS-14 Strain and MS-15 Strain in BHK Cells The growing potentials of the recombinant Japanese encephalitis virus MS-14 strain and MS-15 strain prepared in Example 2 in BHK cells were evaluated. For control, the wild-type virulent Japanese encephalitis virus JaOArS982 strain was used.

Each of the MS-14 strain, MS-15 strain, and JaOArS982 strain was infected to BHK cells; 24, 48, and 72 hours after infection, cell culture supernatants were collected and checked for the emergence of virus. The virus contents in the culture supernatants at each time were measured by the plaque method. For all strains, growth in the BHK cells was confirmed.

Example 4

Evaluation of the Neurotoxicity of the Recombinant Japanese Encephalitis Virus MS-14 Strain and MS-15 Strain in Normal Mature Mice Using the recombinant Japanese encephalitis virus MS-14 strain and MS-15 strain prepared in Example 2, the neurotoxicity of each strain was evaluated by the intraperitoneal inoculation method in normal mature mice. For virulent control, the wild-type virulent Japanese encephalitis virus JaOArS982 strain was used; for attenuated control, the Japanese encephalitis virus vaccine ML-17 strain was used.

Ten mice (4-week-old male and female ICR mice, 5 animals in each group) were given $10^1$ to $10^6$ plaque forming units of the MS-14 strain, MS-15 strain, ML-17 strain, or JaOArS982 strain by intracerebral inoculation, and observed daily for 3 weeks, and $LD_{50}$ was calculated by the Read-Muench method. The results of this test are shown in Table 3.

TABLE 3

| Virus strain | Feature | $LD_{50}$ (ffu) |
|---|---|---|
| JaOH0566 | Wild type | $6.3 \times 10^1$ |
| ML-17 | Vaccine strain | $>1.0 \times 10^6$ |
| JaOArS982 | Wild type | $1.6 \times 10^1$ |
| MS-14 | Recombinant mutant: 127M→I (prM) | $>1.0 \times 10^6$ |
| MS-15 | Recombinant mutant: 274N→T (M) | $1.0 \times 10^3$ |
| MS-14 rev* | Wild type (revertant) | $3.2 \times 10^1$ |

*MS-14 rev represents a revertant of MS-14, prepared from MS-14 using Long-PCR-based site-directed mutagenesis.

As shown in Table 3, the MS-14 strain and MS-15 strain were significantly attenuated compared to the virulent JaOArS982 strain. Particularly, the MS-14 strain had a toxicity similar to that of the ML-17 strain, which is a Japanese encephalitis virus vaccine strain.

This demonstrated that neurotoxicity in mice could be reduced by amino acid substitution in the prM protein.

From the results above, it was suggested that amino acid mutations introduced to the MS-14 strain and MS-15 strain, which are recombinant Japanese encephalitis viruses, might be useful in preparing a Japanese encephalitis live vaccine. Furthermore, because MS-14 exhibits a low degree of pathogenicity in high-dose inoculation, it was suggested that a mutation on NS might also be necessary for attenuation.

Example 5

Construction of cDNA of Chimeric Flavivirus of Japanese Encephalitis Virus and West Nile Virus (ML-17/WN (E Gene))

To prepare ML-17/WN (E gene), which is a chimeric flavivirus wherein the E protein of the Japanese encephalitis virus vaccine ML-17 strain is replaced by the E protein of West Nile virus, a cDNA of ML-17/WN (E gene) was constructed in accordance with the method of preparing a recombinant Japanese encephalitis virus utilizing the Long-PCR method, described in Morita et al., Virology 287:417-426, 2001.

As shown in FIG. 4, with the gene RNA of a Japanese encephalitis virus live vaccine strain (ML-17 strain) as the template, using a set of primer 1A and primer 2A and a set of primer 5A and primer 6A, by the Long-RT-PCR method, Japanese encephalitis virus gene fragments corresponding to the respective primer sets (fragments 1A and 3A) were prepared.

Also, with the gene RNA of West Nile virus (NY99-35262-11 strain) as the template, using a set of primer 3A and primer 4A, by the Long-RT-PCR method, West Nile virus gene fragment 2A was prepared.

After each fragment was purified by agarose electrophoresis, first, with fragments 1A and 2A as the templates, using a set of primers 1A and 4A, again by the Long-PCR method, gene fragment 4A was prepared.

This gene fragment was purified in the same manner; then, with gene fragments 3A and 4A as the templates, using a set of primers 1A and 6A, the Long-PCR method was performed to prepare a chimeric virus cDNA (fragment 5A) of ML-17/WN (E gene), which has the T7 promoter sequence at the 5' terminus thereof and the West Nile virus E protein gene.

The primers used in this Example are shown in Table 4.

| Name of primer | Corresponding nucleotide position on the genome* | Nucleotide sequence* |
|---|---|---|
| primer 5A | JE2478-2513 WN2431-N | GGAGGAGTTCTGCTCTTCCTCTCCGTG AACGTGCACGCTGACACTGGATGTGCC ATTGACATCACAAGAAAAGAG (SEQ ID NO:62) |
| primer 4A | JE2478-2513 WN2433-R | CTCTTTTCTTGTGATGTCAATGGCACA TCCAGTGTCAGCGTGCACGTTCACGGA GAGGAAGAGCAGAACTCCT (SEQ ID NO:61) |
| primer 6A | JE-NR | AGATCCTGTGTTCTTCCTCACCACCAG CTACATACTTCGG (SEQ ID NO:63) |
| primer 3A | ML17 941 WN 967 S | CACCATCCTCCTGCTGCTGGTCGCTCC GGCTTACAGTTTCAACTGCCTTGGAAT GAGCAACAGAGACTTC (SEQ ID NO:60) |
| primer 2A | ML17 945 WN 967 R | CCAAGAAGTCTCTGTTGCTCATTCCAA GGCAGTTGAAACTGTAAGCCGGAGCGA CCAGCAGCAGGAGGAT (SEQ ID NO:59) |
| primer 1A | T7 promoter JE1-40 N | <u>AAATTTAATACGACTCACTATAGAAG</u> TTTATCTGTGTGAACTTCTTGGCTTAG TATCGTTG (SEQ ID NO:58) |

*: JE represents the Japanese encephalitis virus JaOAr982 strain;
ML17 represents the sequence of the Japanese encephalitis virus ML-17 strain;
WN represents the sequence of West Nile virus. S or N represents a sense sequence;
R represents a complementary sequence. The underline indicates the T7 promoter sequence.

Example 6

Production of Chimeric Flavivirus from cDNA of ML-17/WN (E Gene)

With the cDNA of the chimeric flavivirus of Japanese encephalitis virus and West Nile virus, constructed in Example 5 (fragment 5A in FIG. 4), as the template, an in vitro RNA synthesis reaction was performed to prepare an artificial full-length chimeric virus gene RNA. This RNA was introduced into mosquito cells (C6/36 cells) by the electroporation method and the cells were cultured for 5 days, after which the chimeric virus emerging in the culture supernatant was recovered.

Example 7

Evaluation of the Growing Potential of ML-17/WN (E Gene) Chimeric Flavivirus The chimeric virus used was the ML-17/WN (E gene) as obtained in Example 6. ML-17/WN (E gene) and the ML-17 strain were grown in C6/36 cells and BHK cells, and the infected culture broths were dispensed and stored at −70° C. For both types of cells, an Eagle MEM culture broth supplemented with non-essential amino acids was used, with fetal bovine serum added at a concentration as required (2 to 10%). The infectivity titers of the culture broths in the growth experiment are shown in Table 5. ML-17/WN (E gene) had a growing potential equivalent to that of ML-17.

TABLE 5

Growth of ML-17/WN (E gene) chimeric flavivirus and ML-17 in C6/36 cells and BHK cells

|  | Virus strain | Titer (ffu/ml) |
|---|---|---|
| C6/36 | ML-17/WN E gene | $2.1 \times 10^7$ |
|  | ML-17 | $2.0 \times 10^7$ |
| BHK | ML-17/WN E gene | $5.3 \times 10^6$ |
|  | ML-17 | $4.0 \times 10^5$ |

Example 8

Evaluation of the Neurotoxicity of ML-17/WN (E Gene) Chimeric Virus

Using the recombinant chimeric virus ML-17/WN (E gene) prepared in Example 6, the neurotoxicity was evaluated by the intracerebral inoculation method in normal mature mice. Also examined by intraperitoneal administration was infection from peripheral to the central nervous system (brain nerve invasiveness). For control, the JaOH0566 strain, which is a wild-type highly virulent strain Japanese encephalitis viruses, the West Nile virus NY99-3562-11 strain, and the Japanese encephalitis virus vaccine ML-17 strain, which is an attenuated strain, were used.

C57BL/B6 mice at 4 weeks after birth were given 101 to $10^7$ of each virus by intracerebral inoculation, and observed for 28 days. $LD_{50}$ was calculated by the Read-Muench method.

Table 6 shows the $LD_{50}$ of ML-17/WN (E gene) obtained from the experiment. ML-17/WN (E gene) was significantly attenuated compared to the highly virulent JaOH0566 strain. Particularly, ML-17/WN (E gene) had a toxicity similar to that of the ML-17 strain, which is a Japanese encephalitis virus vaccine strain.

TABLE 6

$LD_{50}$ of ML-17/WN (E gene) in C57BL/B6 mice

| Virus strain | $LD_{50}$ (ffu) |
|---|---|
| JaOH0566 | $6.0 \times 10^1$ |
| NY99-35262-11 | $5.0 \times 10^0$ |
| ML-17 | $>1.0 \times 10^7$ |
| ML-17/WN (E gene) | $>1.0 \times 10^7$ |

Example 9

Property of the ML-17/WN (E Gene) Chimeric Virus

The infectivity of the ML-17/WN (E gene) chimeric virus to mosquitoes was investigated. *Culex tritaeniorhynchus* OK7 was allowed to suck a mixture of the virus in rabbit blood (antibody negative) by the transmembrane method. By evaluating the PFU (Plaque-Forming Unit) and the incidence rate in suckling mice, the infection rate was calculated.

After the mosquitoes allowed to suck the chimeric virus by the transmembrane method were reared for 10 days and 21 days, they were emulsified, and demonstration of the presence of the virus was attempted by intracerebral inoculation in suckling mice and PFU evaluation. Even when the ML-17/WN (E gene) virus was allowed to be sucked at not less than $10^2$ PFU per mosquito, there was absolutely no evidence for the presence of the virus.

The ML-17/WN (E gene) chimeric virus did not exhibit susceptibility to *Culex tritaeniorhynchus*.

Example 10

Evaluation of the Defensive Potency of a Live Vaccine Comprising the ML-17/WN (E Gene) Chimeric Virus An immunization experiment was performed using 2-week-old C57BL/B6 and C3H/He mice.

An investigation was performed using the two inbred lines of mice. The non-immunized control group was fatally infected by an intracerebral challenge with West Nile virus (NY99-35262-11 strain), whereas the group given ML-17/WN (E gene) by intraperitoneal inoculation exhibited significant defense against infection.

INDUSTRIAL APPLICABILITY

According to the present invention, an attenuated chimeric flavivirus having attenuating mutation(s) in portion(s) other than the E protein is provided. Because the attenuation of the chimeric flavivirus of the present invention can be achieved without modifying the E protein, attenuated live vaccines for various flavivirus infections can be brought into practical application in a short time, without reducing the immune induction potential.

This application is based on a patent application No. 2004-374630 filed in Japan, the contents of which are entirely incorporated herein by reference.

The invention claimed is:

1. An isolated nucleic acid molecule comprising a nucleotide sequence that encodes a Japanese encephalitis virus having one or more amino acid mutations that attenuate the virus in the i) pre-membrane protein or ii) the pre-membrane protein and non-structural protein, and having no amino acid mutations that attenuate the virus in the envelope protein, wherein the position of the amino acid mutation that attenuates said Japanese encephalitis virus is at least one selected from the group consisting of the 127th, 274th, 1209th, 2462nd, 2463rd, 2479th, 2652nd and 3380th, counted from the amino acid next to the starting methionine of the Japanese encephalitis viral polyprotein.

2. A vector comprising the nucleic acid molecule of claim 1.

3. An isolated attenuated Japanese encephalitis virus encoded by the nucleic acid molecule of claim 1.

4. A method of preparing the nucleic acid molecule of claim 1, which comprises a step for introducing nucleotide mutations that produce one or more amino acid mutations that attenuate the virus into nucleotide sequence(s) that encode(s) i) the pre-membrane protein or ii) the pre-membrane protein and non-structural protein in a nucleic acid molecule comprising a nucleotide sequence that encodes Japanese encephalitis virus.

5. A method of preparing an attenuated Japanese encephalitis virus, which comprises expressing the nucleic acid molecule of claim 1 to prepare an attenuated Japanese encephalitis virus.

* * * * *

SEQUENCE LISTING

<160> NUMBER OF SEQ ID NOS: 63

<210> SEQ ID NO 1
<211> LENGTH: 10976
<212> TYPE: DNA
<213> ORGANISM: Japanese encephalitis virus
<220> FEATURE:
<221> NAME/KEY: CDS
<222> LOCATION: (96)..(10391)

<400> SEQUENCE: 1

```
agaagtttat ctgtgtgaac ttcttggctt agtatcgttg agaagaatcg agagattagt        60
gcagtttaaa cagttttta gaacggaaga taacc atg act aaa aaa cca gga           113
                                    Met Thr Lys Lys Pro Gly
                                     1               5 ggg ccc ggt aaa aac cgg gct atc aat atg ctg aaa cgc ggc cta ccc         161
Gly Pro Gly Lys Asn Arg Ala Ile Asn Met Leu Lys Arg Gly Leu Pro
            10                  15                  20 cgc gta ttc cca cta gtg gga gtg aag agg gta gta atg agc ttg ttg         209
Arg Val Phe Pro Leu Val Gly Val Lys Arg Val Val Met Ser Leu Leu
25                  30                  35 gac ggc aga ggg cca gta cgt ttc gtg ctg gct ctt atc acg ttc ttc         257
Asp Gly Arg Gly Pro Val Arg Phe Val Leu Ala Leu Ile Thr Phe Phe
        40                  45                  50 aag ttt aca gca tta gcc ccg acc aag gcg ctt tta ggc cga tgg aaa         305
Lys Phe Thr Ala Leu Ala Pro Thr Lys Ala Leu Leu Gly Arg Trp Lys
55                  60                  65                  70 gca gtg gaa aag agt gta gca atg aaa cat ctc act agt ttc aaa cga         353
Ala Val Glu Lys Ser Val Ala Met Lys His Leu Thr Ser Phe Lys Arg
                75                  80                  85 gaa ctt gga aca ctc att gac gcc gtg aac aag cgg ggc aga aag caa         401
Glu Leu Gly Thr Leu Ile Asp Ala Val Asn Lys Arg Gly Arg Lys Gln
            90                  95                 100 aac aaa aga gga gga aat gaa ggc tca atc atg tgg ctt gcg agc ttg         449
Asn Lys Arg Gly Gly Asn Glu Gly Ser Ile Met Trp Leu Ala Ser Leu
        105                 110                 115 gca gtt gtc ata gct tgt gca gga gcc ata aag ttg tca aat ttc cag         497
Ala Val Val Ile Ala Cys Ala Gly Ala Ile Lys Leu Ser Asn Phe Gln
120                 125                 130 ggg aag ctt ttg atg acc att aac aac acg gac att gca gac gtt atc         545
Gly Lys Leu Leu Met Thr Ile Asn Asn Thr Asp Ile Ala Asp Val Ile
135                 140                 145                 150 gta att ccc acc tca aaa gga gag aac aga tgc tgg gtc cgg gca atc         593
Val Ile Pro Thr Ser Lys Gly Glu Asn Arg Cys Trp Val Arg Ala Ile
                155                 160                 165 gac gtc ggc tac atg tgt gag gac act atc acg tac gaa tgt cct aag         641
Asp Val Gly Tyr Met Cys Glu Asp Thr Ile Thr Tyr Glu Cys Pro Lys
            170                 175                 180 ctt gcc atg ggc aat gat cca gag gat gtg gac tgc tgg tgt gac aac         689
Leu Ala Met Gly Asn Asp Pro Glu Asp Val Asp Cys Trp Cys Asp Asn
        185                 190                 195 caa gaa gtc tac gtc caa tat gga cgg tgc acg cgg acc agg cat tcc         737
Gln Glu Val Tyr Val Gln Tyr Gly Arg Cys Thr Arg Thr Arg His Ser
200                 205                 210 aag cga agc agg aga tcc gtg tcg gtc caa aca cat ggg gag agt tca         785
Lys Arg Ser Arg Arg Ser Val Ser Val Gln Thr His Gly Glu Ser Ser
215                 220                 225                 230 cta gtg aat aaa aaa gag gct tgg ctg gat tca acg aaa gcc aca cga         833
Leu Val Asn Lys Lys Glu Ala Trp Leu Asp Ser Thr Lys Ala Thr Arg
                235                 240                 245
```

-continued

```
tat ctc atg aaa act gag aac tgg atc ata agg aat cct ggc tat gct      881
Tyr Leu Met Lys Thr Glu Asn Trp Ile Ile Arg Asn Pro Gly Tyr Ala
        250                 255                 260 ttc ctg gcg gcg gta ctc ggc tgg atg ctt ggc agt acc aac ggt caa      929
Phe Leu Ala Ala Val Leu Gly Trp Met Leu Gly Ser Thr Asn Gly Gln
        265                 270                 275 cgc gtg gta ttc acc atc ctg ctg ctg gtc gct ccg gct tac agt          977
Arg Val Val Phe Thr Ile Leu Leu Leu Val Ala Pro Ala Tyr Ser
    280                 285                 290 ttt aat tgt ctg gga atg ggc aat cgt gac ttc ata gaa gga gcc agt     1025
Phe Asn Cys Leu Gly Met Gly Asn Arg Asp Phe Ile Glu Gly Ala Ser
295                 300                 305                 310 gga gcc act tgg gtg gac ttg gtg cta gaa gga gat agc tgc ttg aca     1073
Gly Ala Thr Trp Val Asp Leu Val Leu Glu Gly Asp Ser Cys Leu Thr
                315                 320                 325 att atg gca aac gac aaa cca aca ttg gac gtc cgc atg atc aac atc     1121
Ile Met Ala Asn Asp Lys Pro Thr Leu Asp Val Arg Met Ile Asn Ile
                330                 335                 340 gaa gct agc caa ctt gcc gag gtt aga agt tac tgt tat cat gct tca     1169
Glu Ala Ser Gln Leu Ala Glu Val Arg Ser Tyr Cys Tyr His Ala Ser
        345                 350                 355 gtc act gac atc tcg acg gtg gct cgg tgc ccc acg act gga gaa gcc     1217
Val Thr Asp Ile Ser Thr Val Ala Arg Cys Pro Thr Thr Gly Glu Ala
        360                 365                 370 cac aac gag aag cga gct gat agt agc tat gtg tgc aaa caa ggc ttc     1265
His Asn Glu Lys Arg Ala Asp Ser Ser Tyr Val Cys Lys Gln Gly Phe
375                 380                 385                 390 act gat cgt ggg tgg ggc aac gga tgt gga ctt ttc ggg aag gga agc     1313
Thr Asp Arg Gly Trp Gly Asn Gly Cys Gly Leu Phe Gly Lys Gly Ser
                395                 400                 405 att gac aca tgt gca aaa ttc tcc tgc acc agc aaa gcg att ggg aga     1361
Ile Asp Thr Cys Ala Lys Phe Ser Cys Thr Ser Lys Ala Ile Gly Arg
                410                 415                 420 aca atc cag cca gaa aac atc aaa tac aaa gtt ggc att ttt gtg cat     1409
Thr Ile Gln Pro Glu Asn Ile Lys Tyr Lys Val Gly Ile Phe Val His
        425                 430                 435 gga gcc act act tcg gaa aac cat ggg aat tat tca gcg caa gtt ggg     1457
Gly Ala Thr Thr Ser Glu Asn His Gly Asn Tyr Ser Ala Gln Val Gly
        440                 445                 450 gcg tcc cag gcg gca aag ttc aca gta aca ccc aat gct cct tcg ata     1505
Ala Ser Gln Ala Ala Lys Phe Thr Val Thr Pro Asn Ala Pro Ser Ile
455                 460                 465                 470 acc ctc aaa ctt ggt gac tac gga gaa gtc aca ctg gac tgt gag cca     1553
Thr Leu Lys Leu Gly Asp Tyr Gly Glu Val Thr Leu Asp Cys Glu Pro
                475                 480                 485 agg agt gga ctg aac act gaa gcg ttt tac gtc atg acc gtg ggg tca     1601
Arg Ser Gly Leu Asn Thr Glu Ala Phe Tyr Val Met Thr Val Gly Ser
                490                 495                 500 aag tca ttt ctg gtc cat agg gaa tgg ttt cat gac ctc gct ctc ccc     1649
Lys Ser Phe Leu Val His Arg Glu Trp Phe His Asp Leu Ala Leu Pro
        505                 510                 515 tgg acg tcc cct tcg agc aca gcg tgg aga aac aga gaa ctc ctc atg     1697
Trp Thr Ser Pro Ser Ser Thr Ala Trp Arg Asn Arg Glu Leu Leu Met
        520                 525                 530 gag ttt gaa gag gcg cac gcc aca aaa cag tcc gtt gtt gct ctt ggg     1745
Glu Phe Glu Glu Ala His Ala Thr Lys Gln Ser Val Val Ala Leu Gly
535                 540                 545                 550 tca cag gaa gga ggc ctc cat cag gcg ttg gca gga gcc atc gtg gtg     1793
Ser Gln Glu Gly Gly Leu His Gln Ala Leu Ala Gly Ala Ile Val Val
                555                 560                 565
```

```
gag tac tca agt tca gtg aag tta aca tca ggc cac ctg aaa tgt agg      1841
Glu Tyr Ser Ser Ser Val Lys Leu Thr Ser Gly His Leu Lys Cys Arg
            570                 575                 580 ctg aaa atg gac aaa ctg gct ctg aaa ggc aca acc tat ggc atg tgc      1889
Leu Lys Met Asp Lys Leu Ala Leu Lys Gly Thr Thr Tyr Gly Met Cys
            585                 590                 595 aca gaa aaa ttc tcc ttc gcg aaa aat ccg gcg gac act ggt cac ggg      1937
Thr Glu Lys Phe Ser Phe Ala Lys Asn Pro Ala Asp Thr Gly His Gly
        600                 605                 610 aca gtt gtc att gaa ctc tcc tac tct ggg agt gat ggc ccc tgc aaa      1985
Thr Val Val Ile Glu Leu Ser Tyr Ser Gly Ser Asp Gly Pro Cys Lys
615                 620                 625                 630 att ccg att gtc tcc gtt gcg agc ctc aat gac atg acc ccc gtc ggg      2033
Ile Pro Ile Val Ser Val Ala Ser Leu Asn Asp Met Thr Pro Val Gly
                635                 640                 645 cgg ctg gtg aca gtg aac ccc ttc gtc gcg act tcc agt gcc aat tca      2081
Arg Leu Val Thr Val Asn Pro Phe Val Ala Thr Ser Ser Ala Asn Ser
            650                 655                 660 aag gtg ctg gtc gag atg gaa ccc ccc ttc gga gac tcc tac atc gta      2129
Lys Val Leu Val Glu Met Glu Pro Pro Phe Gly Asp Ser Tyr Ile Val
            665                 670                 675 gtt gga cgg gga gac aag cag atc aac cac cat tgg cat aaa gct gga      2177
Val Gly Arg Gly Asp Lys Gln Ile Asn His His Trp His Lys Ala Gly
        680                 685                 690 agc acg ctg ggc aaa gcc ttt tca aca act ttg aag gga gct cag aga      2225
Ser Thr Leu Gly Lys Ala Phe Ser Thr Thr Leu Lys Gly Ala Gln Arg
695                 700                 705                 710 ctg gca gcg ctg ggt gac aca gcc tgg gac ttt ggc tcc att gga ggg      2273
Leu Ala Ala Leu Gly Asp Thr Ala Trp Asp Phe Gly Ser Ile Gly Gly
                715                 720                 725 gtc ttc aac tcc ata gga aaa gcc gtt cac caa gtg ttt ggt ggt gcc      2321
Val Phe Asn Ser Ile Gly Lys Ala Val His Gln Val Phe Gly Gly Ala
            730                 735                 740 ttc aga aca ctc ttc ggg gga atg tct tgg atc aca caa ggg cta atg      2369
Phe Arg Thr Leu Phe Gly Gly Met Ser Trp Ile Thr Gln Gly Leu Met
            745                 750                 755 ggt gcc cta cta ctc tgg atg ggc gtc aac gca cga gac cga tca att      2417
Gly Ala Leu Leu Leu Trp Met Gly Val Asn Ala Arg Asp Arg Ser Ile
760                 765                 770 gct ttg gcc ttc tta gcc aca gga ggt gtg ctc gtg ttt tta gcg acc      2465
Ala Leu Ala Phe Leu Ala Thr Gly Gly Val Leu Val Phe Leu Ala Thr
775                 780                 785                 790 aat gtg cat gct gac act gga tgt gcc att gac atc aca aga aaa gag      2513
Asn Val His Ala Asp Thr Gly Cys Ala Ile Asp Ile Thr Arg Lys Glu
                795                 800                 805 atg agg tgt gga agt ggc atc ttc gtg cac aac gac gtg gaa gcc tgg      2561
Met Arg Cys Gly Ser Gly Ile Phe Val His Asn Asp Val Glu Ala Trp
            810                 815                 820 gtg gat agg tat aaa tat ttg cca gaa acg ccc aga tcc cta gca aag      2609
Val Asp Arg Tyr Lys Tyr Leu Pro Glu Thr Pro Arg Ser Leu Ala Lys
            825                 830                 835 atc gtc cac aaa gcg cac aag gaa ggc gtg tgc gga gtc aga tct gtc      2657
Ile Val His Lys Ala His Lys Glu Gly Val Cys Gly Val Arg Ser Val
840                 845                 850 act aga ctg gag cat caa atg tgg gaa gcc gta cgg gat gaa ttg aac      2705
Thr Arg Leu Glu His Gln Met Trp Glu Ala Val Arg Asp Glu Leu Asn
855                 860                 865                 870 gtc ctg ctc aaa gag aat gca gtg gac ctc agt gtg gtt gtg aac aag      2753
Val Leu Leu Lys Glu Asn Ala Val Asp Leu Ser Val Val Val Asn Lys
                875                 880                 885
```

| | | |
|---|---|---|
| ccc gtg ggg aga tat cgc tca gcc cct aaa cgc ctg tcc atg acg caa<br>Pro Val Gly Arg Tyr Arg Ser Ala Pro Lys Arg Leu Ser Met Thr Gln<br>         890                  895                  900 | | 2801 |
| gag aag ttt gaa atg ggc tgg aaa gca tgg gga aaa agc att ctc ttt<br>Glu Lys Phe Glu Met Gly Trp Lys Ala Trp Gly Lys Ser Ile Leu Phe<br>        905                  910                  915 | | 2849 |
| gcc ccg gaa ttg gcc aac tcc aca ttt gtc gta gat gga cct gag aca<br>Ala Pro Glu Leu Ala Asn Ser Thr Phe Val Val Asp Gly Pro Glu Thr<br>920                  925                  930 | | 2897 |
| aag gaa tgc cct gat gag cac aga gct tgg aac agc atg caa atc gaa<br>Lys Glu Cys Pro Asp Glu His Arg Ala Trp Asn Ser Met Gln Ile Glu<br>935                  940                  945                  950 | | 2945 |
| gac ttc ggc ttt ggc atc aca tca acc cgt gtg tgg ctg aag att aga<br>Asp Phe Gly Phe Gly Ile Thr Ser Thr Arg Val Trp Leu Lys Ile Arg<br>                  955                  960                  965 | | 2993 |
| gag gag agc act gac gag tgt gat gga gcg atc ata ggt acg gct gtc<br>Glu Glu Ser Thr Asp Glu Cys Asp Gly Ala Ile Ile Gly Thr Ala Val<br>        970                  975                  980 | | 3041 |
| aaa gga cat gtg gca gtc cat agt gac ttg tcg tac tgg att gag agt<br>Lys Gly His Val Ala Val His Ser Asp Leu Ser Tyr Trp Ile Glu Ser<br>985                  990                  995 | | 3089 |
| cgc tac aac gac aca tgg aaa ctt gag agg gca gtc ttt gga gaa<br>Arg Tyr Asn Asp Thr Trp Lys Leu Glu Arg Ala Val Phe Gly Glu<br>                1000                1005              1010 | | 3134 |
| gtt aaa tcc tgc act tgg cca gag aca cac acc cta tgg gga gat<br>Val Lys Ser Cys Thr Trp Pro Glu Thr His Thr Leu Trp Gly Asp<br>1015                1020              1025 | | 3179 |
| ggt gtt gag gaa agt gaa ctc atc atc ccg cac acc ata gcc gga<br>Gly Val Glu Glu Ser Glu Leu Ile Ile Pro His Thr Ile Ala Gly<br>        1030                1035              1040 | | 3224 |
| cca aaa agc aag cat aat cgg agg gaa gga tat aag aca caa aac<br>Pro Lys Ser Lys His Asn Arg Arg Glu Gly Tyr Lys Thr Gln Asn<br>1045                1050              1055 | | 3269 |
| cag gga cct tgg gac gag aat ggc ata gtc ttg gac ttt gac tat<br>Gln Gly Pro Trp Asp Glu Asn Gly Ile Val Leu Asp Phe Asp Tyr<br>        1060                1065              1070 | | 3314 |
| tgc cca ggg aca aaa gtc acc att aca gag gat tgt ggc aag aga<br>Cys Pro Gly Thr Lys Val Thr Ile Thr Glu Asp Cys Gly Lys Arg<br>1075                1080              1085 | | 3359 |
| ggc cct tcg gtc aga acc act act gac agt gga aag ttg atc act<br>Gly Pro Ser Val Arg Thr Thr Thr Asp Ser Gly Lys Leu Ile Thr<br>1090                1095              1100 | | 3404 |
| gac tgg tgc tgt cgc agt tgc tcc ctt ccg ccc cta cga ttc cgg<br>Asp Trp Cys Cys Arg Ser Cys Ser Leu Pro Pro Leu Arg Phe Arg<br>1105                1110              1115 | | 3449 |
| aca gaa aat ggc tgc tgg tac gga atg gaa atc aga cct gtc agg<br>Thr Glu Asn Gly Cys Trp Tyr Gly Met Glu Ile Arg Pro Val Arg<br>1120                1125              1130 | | 3494 |
| cat gat gaa aca aca ctc gtc aga tcg cag gtt gat gct ttt aat<br>His Asp Glu Thr Thr Leu Val Arg Ser Gln Val Asp Ala Phe Asn<br>1135                1140              1145 | | 3539 |
| ggt gaa atg gtt gac cct ttt cag ctg ggc ctt ctg gtg atg ttt<br>Gly Glu Met Val Asp Pro Phe Gln Leu Gly Leu Leu Val Met Phe<br>1150                1155              1160 | | 3584 |
| ctg gcc acc cag gag gtc ctt cgc aag agg tgg acg gcc aga ttg<br>Leu Ala Thr Gln Glu Val Leu Arg Lys Arg Trp Thr Ala Arg Leu<br>1165                1170              1175 | | 3629 |
| acc att cct gcg gtt ttg ggg gcc cta ctt gtg ctg atg ctt ggg<br>Thr Ile Pro Ala Val Leu Gly Ala Leu Leu Val Leu Met Leu Gly<br>1180                1185              1190 | | 3674 |

-continued

| | | |
|---|---|---|
| ggc atc act tac act gat ttg gcg agg tat gtg gtg cta gtc gct<br>Gly Ile Thr Tyr Thr Asp Leu Ala Arg Tyr Val Val Leu Val Ala<br>1195                    1200                    1205 | 3719 |
| gcc tct ttc gca gag gcc aac agt gga gga gat gtc ctg cac ctt<br>Ala Ser Phe Ala Glu Ala Asn Ser Gly Gly Asp Val Leu His Leu<br>1210                    1215                    1220 | 3764 |
| gct ttg att gcc gtt ttc aag atc caa cca gca ttt tta gtg atg<br>Ala Leu Ile Ala Val Phe Lys Ile Gln Pro Ala Phe Leu Val Met<br>1225                    1230                    1235 | 3809 |
| aac atg ctt agc acg aga tgg acg aac caa gaa aac gtg gtt ctg<br>Asn Met Leu Ser Thr Arg Trp Thr Asn Gln Glu Asn Val Val Leu<br>1240                    1245                    1250 | 3854 |
| gtc cta ggg gct gcc ttt ttc caa ttg gcc tca gta gat ctg caa<br>Val Leu Gly Ala Ala Phe Phe Gln Leu Ala Ser Val Asp Leu Gln<br>1255                    1260                    1265 | 3899 |
| ata gga gtt cac gga atc ctg aat gcc gcc gct ata gca tgg atg<br>Ile Gly Val His Gly Ile Leu Asn Ala Ala Ala Ile Ala Trp Met<br>1270                    1275                    1280 | 3944 |
| att gtc cgg gcg atc acc ttc ccc aca acc tcc tcc gtc acc atg<br>Ile Val Arg Ala Ile Thr Phe Pro Thr Thr Ser Ser Val Thr Met<br>1285                    1290                    1295 | 3989 |
| cca gtc tta gcg ctt cta act ccg gga atg agg gct cta tac cta<br>Pro Val Leu Ala Leu Leu Thr Pro Gly Met Arg Ala Leu Tyr Leu<br>1300                    1305                    1310 | 4034 |
| gat act tac aga atc atc ctc ctc gtc ata ggg att tgc tct ctg<br>Asp Thr Tyr Arg Ile Ile Leu Leu Val Ile Gly Ile Cys Ser Leu<br>1315                    1320                    1325 | 4079 |
| ctg caa gag agg aaa aag acc atg gca aaa aag aaa gga gct gta<br>Leu Gln Glu Arg Lys Lys Thr Met Ala Lys Lys Lys Gly Ala Val<br>1330                    1335                    1340 | 4124 |
| ctc ttg ggc tta gcg ctc aca tcc act gga tgg ttt tcg ccc acc<br>Leu Leu Gly Leu Ala Leu Thr Ser Thr Gly Trp Phe Ser Pro Thr<br>1345                    1350                    1355 | 4169 |
| act ata gct gcc gga cta atg gtc tgc aac cca aac aag aag aga<br>Thr Ile Ala Ala Gly Leu Met Val Cys Asn Pro Asn Lys Lys Arg<br>1360                    1365                    1370 | 4214 |
| ggg tgg cca gct act gag ttt ttg tcg gca gtt gga ttg atg ttt<br>Gly Trp Pro Ala Thr Glu Phe Leu Ser Ala Val Gly Leu Met Phe<br>1375                    1380                    1385 | 4259 |
| gcc atc gta ggt ggt ttg gcg gag ttg gat att gaa tcc atg tca<br>Ala Ile Val Gly Gly Leu Ala Glu Leu Asp Ile Glu Ser Met Ser<br>1390                    1395                    1400 | 4304 |
| ata ccc ttc atg ctg gca ggt ctc atg gca gtg tcc tac gtg gtg<br>Ile Pro Phe Met Leu Ala Gly Leu Met Ala Val Ser Tyr Val Val<br>1405                    1410                    1415 | 4349 |
| tca gga aaa gca aca gat atg tgg ctt gaa cgg gct gcc gac atc<br>Ser Gly Lys Ala Thr Asp Met Trp Leu Glu Arg Ala Ala Asp Ile<br>1420                    1425                    1430 | 4394 |
| agc tgg gag atg gat gct gca atc aca gga agc agt cgg agg ctg<br>Ser Trp Glu Met Asp Ala Ala Ile Thr Gly Ser Ser Arg Arg Leu<br>1435                    1440                    1445 | 4439 |
| gat gtg aag cta gat gat gac gga gat ttt cac ttg att gac gat<br>Asp Val Lys Leu Asp Asp Asp Gly Asp Phe His Leu Ile Asp Asp<br>1450                    1455                    1460 | 4484 |
| ccc ggt gtt cca tgg aag gtc tgg gtc ctg cgc atg tct tgc att<br>Pro Gly Val Pro Trp Lys Val Trp Val Leu Arg Met Ser Cys Ile<br>1465                    1470                    1475 | 4529 |
| ggg tta gcc gcc ctc acg cct tgg gcc att gtt ccc gcc gct ttt<br>Gly Leu Ala Ala Leu Thr Pro Trp Ala Ile Val Pro Ala Ala Phe<br>1480                    1485                    1490 | 4574 |

| | | | | | | | | | | | | | |
|---|---|---|---|---|---|---|---|---|---|---|---|---|---|
| ggt | tat | tgg | ctc | act | tta | aaa | aca | aca | aaa | aga | ggg | ggc gtg ttt | 4619 |
| Gly | Tyr | Trp | Leu | Thr | Leu | Lys | Thr | Thr | Lys | Arg | Gly | Gly Val Phe | |
| | 1495 | | | | 1500 | | | | 1505 | | | | |
| tgg | gac | acg | cca | tcc | cca | aaa | cct | tgc | tca | aaa | gga | gac acc act | 4664 |
| Trp | Asp | Thr | Pro | Ser | Pro | Lys | Pro | Cys | Ser | Lys | Gly | Asp Thr Thr | |
| 1510 | | | | | 1515 | | | | | 1520 | | | |
| aca | gga | gtt | tac | cgc | att | atg | gct | aga | ggg | att | ctt | ggc act tac | 4709 |
| Thr | Gly | Val | Tyr | Arg | Ile | Met | Ala | Arg | Gly | Ile | Leu | Gly Thr Tyr | |
| | 1525 | | | | 1530 | | | | 1535 | | | | |
| cag | gcc | ggc | gtc | gga | gtc | atg | tac | gag | aat | gtt | ttc | cac aca cta | 4754 |
| Gln | Ala | Gly | Val | Gly | Val | Met | Tyr | Glu | Asn | Val | Phe | His Thr Leu | |
| 1540 | | | | | 1545 | | | | | 1550 | | | |
| tgg | cac | aca | act | aga | gga | gca | gct | att | atg | agt | gga | gaa gga aaa | 4799 |
| Trp | His | Thr | Thr | Arg | Gly | Ala | Ala | Ile | Met | Ser | Gly | Glu Gly Lys | |
| | 1555 | | | | 1560 | | | | 1565 | | | | |
| ttg | acg | cca | tac | tgg | ggt | agt | gtg | aaa | gaa | gac | cgc | ata gct tac | 4844 |
| Leu | Thr | Pro | Tyr | Trp | Gly | Ser | Val | Lys | Glu | Asp | Arg | Ile Ala Tyr | |
| 1570 | | | | | 1575 | | | | | 1580 | | | |
| gga | ggc | cca | tgg | agg | ttt | gat | cga | aaa | tgg | aat | gga | act gat gac | 4889 |
| Gly | Gly | Pro | Trp | Arg | Phe | Asp | Arg | Lys | Trp | Asn | Gly | Thr Asp Asp | |
| | 1585 | | | | 1590 | | | | 1595 | | | | |
| gtg | caa | gtg | atc | gtg | gta | gaa | ccg | ggg | aag | gct | gca | gta aac atc | 4934 |
| Val | Gln | Val | Ile | Val | Val | Glu | Pro | Gly | Lys | Ala | Ala | Val Asn Ile | |
| 1600 | | | | | 1605 | | | | | 1610 | | | |
| cag | aca | aaa | cca | gga | gtg | ttt | cgg | act | ccc | ttc | ggg | gag gtt ggg | 4979 |
| Gln | Thr | Lys | Pro | Gly | Val | Phe | Arg | Thr | Pro | Phe | Gly | Glu Val Gly | |
| | 1615 | | | | 1620 | | | | 1625 | | | | |
| gct | gtt | agt | ctg | gat | tat | ccg | cga | gga | aca | tcc | ggc | tca ccc att | 5024 |
| Ala | Val | Ser | Leu | Asp | Tyr | Pro | Arg | Gly | Thr | Ser | Gly | Ser Pro Ile | |
| 1630 | | | | | 1635 | | | | | 1640 | | | |
| ctg | gat | tcc | aat | gga | gac | atc | ata | ggc | ctg | tac | ggc | aat gga gtt | 5069 |
| Leu | Asp | Ser | Asn | Gly | Asp | Ile | Ile | Gly | Leu | Tyr | Gly | Asn Gly Val | |
| | 1645 | | | | 1650 | | | | 1655 | | | | |
| gag | ctt | ggc | gat | ggc | tca | tac | gtc | agc | gcc | atc | gtg | cag ggt gac | 5114 |
| Glu | Leu | Gly | Asp | Gly | Ser | Tyr | Val | Ser | Ala | Ile | Val | Gln Gly Asp | |
| 1660 | | | | | 1665 | | | | | 1670 | | | |
| cgt | cag | gag | gaa | cca | gtc | cca | gaa | gct | tac | acc | cca | aac atg ttg | 5159 |
| Arg | Gln | Glu | Glu | Pro | Val | Pro | Glu | Ala | Tyr | Thr | Pro | Asn Met Leu | |
| | 1675 | | | | 1680 | | | | 1685 | | | | |
| aga | aag | aga | cag | atg | acc | gta | cta | gat | ttg | cac | cct | ggt tca ggg | 5204 |
| Arg | Lys | Arg | Gln | Met | Thr | Val | Leu | Asp | Leu | His | Pro | Gly Ser Gly | |
| 1690 | | | | | 1695 | | | | | 1700 | | | |
| aaa | acc | aag | aaa | att | ctg | cca | caa | ata | att | aag | gac | gct att cag | 5249 |
| Lys | Thr | Lys | Lys | Ile | Leu | Pro | Gln | Ile | Ile | Lys | Asp | Ala Ile Gln | |
| | 1705 | | | | 1710 | | | | 1715 | | | | |
| cag | cgc | cta | aga | aca | gct | gtg | ttg | gca | ccg | acg | cgg | gtg gta gca | 5294 |
| Gln | Arg | Leu | Arg | Thr | Ala | Val | Leu | Ala | Pro | Thr | Arg | Val Val Ala | |
| 1720 | | | | | 1725 | | | | | 1730 | | | |
| gca | gaa | atg | gca | gaa | gct | tta | aga | ggg | ctc | cca | gta | cga tat caa | 5339 |
| Ala | Glu | Met | Ala | Glu | Ala | Leu | Arg | Gly | Leu | Pro | Val | Arg Tyr Gln | |
| | 1735 | | | | 1740 | | | | 1745 | | | | |
| act | tca | gca | gtg | cag | aga | gag | cac | caa | ggg | aat | gaa | ata gtg gat | 5384 |
| Thr | Ser | Ala | Val | Gln | Arg | Glu | His | Gln | Gly | Asn | Glu | Ile Val Asp | |
| 1750 | | | | | 1755 | | | | | 1760 | | | |
| gtg | atg | tgc | cac | gcc | act | ctg | acc | cat | aga | ctg | atg | tca ccg aac | 5429 |
| Val | Met | Cys | His | Ala | Thr | Leu | Thr | His | Arg | Leu | Met | Ser Pro Asn | |
| | 1765 | | | | 1770 | | | | 1775 | | | | |
| aga | gtg | ccc | aac | tac | aac | cta | ttt | gtc | atg | gat | gaa | gct cat ttc | 5474 |
| Arg | Val | Pro | Asn | Tyr | Asn | Leu | Phe | Val | Met | Asp | Glu | Ala His Phe | |
| 1780 | | | | | 1785 | | | | | 1790 | | | |

-continued

| | | |
|---|---|---|
| acc gac cca gcc agt ata gcc gca cga gga tac att gct acc aag<br>Thr Asp Pro Ala Ser Ile Ala Ala Arg Gly Tyr Ile Ala Thr Lys<br>1795                        1800                        1805 | 5519 |
| gtg gaa tta ggg gag gca gca gcc atc ttt atg aca gcg acc ccg<br>Val Glu Leu Gly Glu Ala Ala Ala Ile Phe Met Thr Ala Thr Pro<br>1810                        1815                        1820 | 5564 |
| cct gga acc acg gat cct ttt cct gac tca aat gcc cca atc cat<br>Pro Gly Thr Thr Asp Pro Phe Pro Asp Ser Asn Ala Pro Ile His<br>1825                        1830                        1835 | 5609 |
| gat ttg caa gat gag ata cca gac agg gcg tgg agc agt gga tac<br>Asp Leu Gln Asp Glu Ile Pro Asp Arg Ala Trp Ser Ser Gly Tyr<br>1840                        1845                        1850 | 5654 |
| gaa tgg atc aca gaa tat gcg gga aaa acc gtg tgg ttt gtg gca<br>Glu Trp Ile Thr Glu Tyr Ala Gly Lys Thr Val Trp Phe Val Ala<br>1855                        1860                        1865 | 5699 |
| agc gtg aaa atg ggg aac gag att gca atg tgc ctc caa aga gcg<br>Ser Val Lys Met Gly Asn Glu Ile Ala Met Cys Leu Gln Arg Ala<br>1870                        1875                        1880 | 5744 |
| ggg aaa aag gtc atc caa ctc aac cgc aag tcc tat gac aca gaa<br>Gly Lys Lys Val Ile Gln Leu Asn Arg Lys Ser Tyr Asp Thr Glu<br>1885                        1890                        1895 | 5789 |
| tac cca aaa tgt aag aat gga gac tgg gat ttt gtc atc acc act<br>Tyr Pro Lys Cys Lys Asn Gly Asp Trp Asp Phe Val Ile Thr Thr<br>1900                        1905                        1910 | 5834 |
| gac att tct gaa atg ggg gcc aac ttc ggt gcg agc agg gtc atc<br>Asp Ile Ser Glu Met Gly Ala Asn Phe Gly Ala Ser Arg Val Ile<br>1915                        1920                        1925 | 5879 |
| gac tgt aga aag agc gtg aag ccc acc atc tta gaa gag gga gaa<br>Asp Cys Arg Lys Ser Val Lys Pro Thr Ile Leu Glu Glu Gly Glu<br>1930                        1935                        1940 | 5924 |
| ggc aga gtc atc ctc gga aac cca tcg ccc ata acc agt gca agc<br>Gly Arg Val Ile Leu Gly Asn Pro Ser Pro Ile Thr Ser Ala Ser<br>1945                        1950                        1955 | 5969 |
| gca gct caa cgg agg ggc aga gta ggc aga aac cct aac cag gtt<br>Ala Ala Gln Arg Arg Gly Arg Val Gly Arg Asn Pro Asn Gln Val<br>1960                        1965                        1970 | 6014 |
| gga gat gaa tac cac tat ggg ggg gcc acc agt gaa gat gac agt<br>Gly Asp Glu Tyr His Tyr Gly Gly Ala Thr Ser Glu Asp Asp Ser<br>1975                        1980                        1985 | 6059 |
| aac cta gcc cat tgg aca gag gca aag atc atg tta gat aac ata<br>Asn Leu Ala His Trp Thr Glu Ala Lys Ile Met Leu Asp Asn Ile<br>1990                        1995                        2000 | 6104 |
| cac atg ccc aat gga ctg gtg gcc cag ctc tat gga cca gag agg<br>His Met Pro Asn Gly Leu Val Ala Gln Leu Tyr Gly Pro Glu Arg<br>2005                        2010                        2015 | 6149 |
| gaa aag gcc ttc aca atg gat ggc gaa tac cgt ctc aga ggt gaa<br>Glu Lys Ala Phe Thr Met Asp Gly Glu Tyr Arg Leu Arg Gly Glu<br>2020                        2025                        2030 | 6194 |
| gaa aag aaa aac ttc tta gag ctg ctt agg acg gct gac ctc ccg<br>Glu Lys Lys Asn Phe Leu Glu Leu Leu Arg Thr Ala Asp Leu Pro<br>2035                        2040                        2045 | 6239 |
| gtg tgg ctg gcc tac aag gtg gcg tcc aat ggc atc cag tac acc<br>Val Trp Leu Ala Tyr Lys Val Ala Ser Asn Gly Ile Gln Tyr Thr<br>2050                        2055                        2060 | 6284 |
| gat aga aag tgg tgt ttt gat ggg ccg cgt acg aat gcc ata ctg<br>Asp Arg Lys Trp Cys Phe Asp Gly Pro Arg Thr Asn Ala Ile Leu<br>2065                        2070                        2075 | 6329 |
| gag gac aac acc gag gta gag ata gtc acc cgg atg ggt gag agg<br>Glu Asp Asn Thr Glu Val Glu Ile Val Thr Arg Met Gly Glu Arg<br>2080                        2085                        2090 | 6374 |

-continued

| | | |
|---|---|---|
| aaa atc ctc aag ccg aga tgg ctt gat gca aga gtt tat gca gat<br>Lys Ile Leu Lys Pro Arg Trp Leu Asp Ala Arg Val Tyr Ala Asp<br>2095                          2100                          2105 | 6419 | |
| cac caa gct ctc aag tgg ttc aaa gac ttc gca gca gga aag aga<br>His Gln Ala Leu Lys Trp Phe Lys Asp Phe Ala Ala Gly Lys Arg<br>2110                          2115                          2120 | 6464 | |
| tca gcc gtt agc ttc ata gag gtg ctc ggt cgt atg cct gag cat<br>Ser Ala Val Ser Phe Ile Glu Val Leu Gly Arg Met Pro Glu His<br>2125                          2130                          2135 | 6509 | |
| ttc atg gga aag acg cgg gaa gct tta gac acc atg tac ttg gtt<br>Phe Met Gly Lys Thr Arg Glu Ala Leu Asp Thr Met Tyr Leu Val<br>2140                          2145                          2150 | 6554 | |
| gca acg gct gag aaa ggt ggg aaa gca cac cga atg gct ctc gaa<br>Ala Thr Ala Glu Lys Gly Gly Lys Ala His Arg Met Ala Leu Glu<br>2155                          2160                          2165 | 6599 | |
| gag ctg cca gat gca ctg gaa acc att aca ctt att gtt gct atc<br>Glu Leu Pro Asp Ala Leu Glu Thr Ile Thr Leu Ile Val Ala Ile<br>2170                          2175                          2180 | 6644 | |
| act gtg atg aca gga gga ttc ttt cta ctc atg atg cag cga aag<br>Thr Val Met Thr Gly Gly Phe Phe Leu Leu Met Met Gln Arg Lys<br>2185                          2190                          2195 | 6689 | |
| ggt ata ggg aag atg ggt ctt gga gct cta gtg ctc acg cta gct<br>Gly Ile Gly Lys Met Gly Leu Gly Ala Leu Val Leu Thr Leu Ala<br>2200                          2205                          2210 | 6734 | |
| acc ttc ttc ctg tgg gcg gca gag gtt ccc gga aca aaa ata gca<br>Thr Phe Phe Leu Trp Ala Ala Glu Val Pro Gly Thr Lys Ile Ala<br>2215                          2220                          2225 | 6779 | |
| ggg acc ctg ctg atc gcc ctg ctg ctt atg gtg gtt ctc atc cca<br>Gly Thr Leu Leu Ile Ala Leu Leu Leu Met Val Val Leu Ile Pro<br>2230                          2235                          2240 | 6824 | |
| gaa ccg gaa aag cag agg tca caa aca gat aat caa ctg gcg gtg<br>Glu Pro Glu Lys Gln Arg Ser Gln Thr Asp Asn Gln Leu Ala Val<br>2245                          2250                          2255 | 6869 | |
| ttt ctc atc tgt gtc ttg acc gtg gtt gga gtg gtg gca gca aac<br>Phe Leu Ile Cys Val Leu Thr Val Val Gly Val Val Ala Ala Asn<br>2260                          2265                          2270 | 6914 | |
| gag tac ggg atg cta gaa aaa acc aaa gca gac ctc aag agc atg<br>Glu Tyr Gly Met Leu Glu Lys Thr Lys Ala Asp Leu Lys Ser Met<br>2275                          2280                          2285 | 6959 | |
| ttt ggc gga aag acg cag gca tca gga ctg act gga tta cca agc<br>Phe Gly Gly Lys Thr Gln Ala Ser Gly Leu Thr Gly Leu Pro Ser<br>2290                          2295                          2300 | 7004 | |
| atg gca ctg gac ctg cgt cca gcc aca gct tgg gca ctg tat ggg<br>Met Ala Leu Asp Leu Arg Pro Ala Thr Ala Trp Ala Leu Tyr Gly<br>2305                          2310                          2315 | 7049 | |
| ggg agc aca gtc gtg cta acc cct ctt ctg aag cac ctg atc acg<br>Gly Ser Thr Val Val Leu Thr Pro Leu Leu Lys His Leu Ile Thr<br>2320                          2325                          2330 | 7094 | |
| tcg gaa tac gtc acc aca tcg cta gcc tca att aac tca caa gct<br>Ser Glu Tyr Val Thr Thr Ser Leu Ala Ser Ile Asn Ser Gln Ala<br>2335                          2340                          2345 | 7139 | |
| ggc tca tta ttt gtc ttg cca cga ggc gtg cct ttt acc gac cta<br>Gly Ser Leu Phe Val Leu Pro Arg Gly Val Pro Phe Thr Asp Leu<br>2350                          2355                          2360 | 7184 | |
| gac ttg acc gtt ggc ctc gtc ttc ctt ggc tgt tgg ggt caa atc<br>Asp Leu Thr Val Gly Leu Val Phe Leu Gly Cys Trp Gly Gln Ile<br>2365                          2370                          2375 | 7229 | |
| acc ctc aca acg ttt ttg aca gcc atg gtt ctg gcg aca ctt cac<br>Thr Leu Thr Thr Phe Leu Thr Ala Met Val Leu Ala Thr Leu His<br>2380                          2385                          2390 | 7274 | |

| | | |
|---|---|---|
| tat ggg tac atg ctc cct gga tgg caa gca gaa gca ctc agg gct<br>Tyr Gly Tyr Met Leu Pro Gly Trp Gln Ala Glu Ala Leu Arg Ala<br>　　 2395　　　　　　　 2400　　　　　　　 2405 | | 7319 |
| gcc cag aga agg aca gcg gct gga ata atg aag aat gcc gtt gtt<br>Ala Gln Arg Arg Thr Ala Ala Gly Ile Met Lys Asn Ala Val Val<br>2410　　　　　　　 2415　　　　　　　 2420 | | 7364 |
| gac gga atg gtc gcc act gat gtg cct gaa ctg gaa agg acc act<br>Asp Gly Met Val Ala Thr Asp Val Pro Glu Leu Glu Arg Thr Thr<br>　　 2425　　　　　　　 2430　　　　　　　 2435 | | 7409 |
| cct ctg atg caa aag aaa gtc gga cag gtg ctc ctc ata ggg gta<br>Pro Leu Met Gln Lys Lys Val Gly Gln Val Leu Leu Ile Gly Val<br>2440　　　　　　　 2445　　　　　　　 2450 | | 7454 |
| agc gtg gca gcg ttc ctc gtc aac ccc aaa atc acc act gtg aga<br>Ser Val Ala Ala Phe Leu Val Asn Pro Lys Ile Thr Thr Val Arg<br>　　 2455　　　　　　　 2460　　　　　　　 2465 | | 7499 |
| gaa gca ggg gtg ttg gtg aca gcg gct acg ctc tct ttg tgg gac<br>Glu Ala Gly Val Leu Val Thr Ala Ala Thr Leu Ser Leu Trp Asp<br>2470　　　　　　　 2475　　　　　　　 2480 | | 7544 |
| aac gga gcc agt gcc gtt tgg aat tcc acc act gcc acg gga ctc<br>Asn Gly Ala Ser Ala Val Trp Asn Ser Thr Thr Ala Thr Gly Leu<br>　　 2485　　　　　　　 2490　　　　　　　 2495 | | 7589 |
| tgc cat gta atg cga ggt agc tac ctg gct gga ggc tcc att gct<br>Cys His Val Met Arg Gly Ser Tyr Leu Ala Gly Gly Ser Ile Ala<br>2500　　　　　　　 2505　　　　　　　 2510 | | 7634 |
| tgg act ctc atc aag aac gct gac aag ccc tcc tta aaa agg gga<br>Trp Thr Leu Ile Lys Asn Ala Asp Lys Pro Ser Leu Lys Arg Gly<br>　　 2515　　　　　　　 2520　　　　　　　 2525 | | 7679 |
| agg cct ggg ggc agg acg cta ggg gag cag tgg aag gaa aaa cta<br>Arg Pro Gly Gly Arg Thr Leu Gly Glu Gln Trp Lys Glu Lys Leu<br>2530　　　　　　　 2535　　　　　　　 2540 | | 7724 |
| aat gcc atg agc aga gaa gag ttt ttt aaa tac cgg aga gag gcc<br>Asn Ala Met Ser Arg Glu Glu Phe Phe Lys Tyr Arg Arg Glu Ala<br>　　 2545　　　　　　　 2550　　　　　　　 2555 | | 7769 |
| ata atc gag gtg gac cgc act gaa gca cgc agg gct aga cgt gaa<br>Ile Ile Glu Val Asp Arg Thr Glu Ala Arg Arg Ala Arg Arg Glu<br>2560　　　　　　　 2565　　　　　　　 2570 | | 7814 |
| aat aac ata gtg gga gga cat ccg gtt tcg cga ggc tca gca aaa<br>Asn Asn Ile Val Gly Gly His Pro Val Ser Arg Gly Ser Ala Lys<br>　　 2575　　　　　　　 2580　　　　　　　 2585 | | 7859 |
| ctc cgt tgg ctc gta gag aaa gga ttt gtc tcg cca ata gga aaa<br>Leu Arg Trp Leu Val Glu Lys Gly Phe Val Ser Pro Ile Gly Lys<br>2590　　　　　　　 2595　　　　　　　 2600 | | 7904 |
| gtc att gat cta ggg tgt ggg cgt gga gga tgg agc tac tac gca<br>Val Ile Asp Leu Gly Cys Gly Arg Gly Gly Trp Ser Tyr Tyr Ala<br>　　 2605　　　　　　　 2610　　　　　　　 2615 | | 7949 |
| gca acc ctg aag aag gtc cag gaa gtc aga gga tac acg aaa ggt<br>Ala Thr Leu Lys Lys Val Gln Glu Val Arg Gly Tyr Thr Lys Gly<br>2620　　　　　　　 2625　　　　　　　 2630 | | 7994 |
| ggg gcg gga cat gaa gaa ccg atg ctc atg cag agc tac ggc tgg<br>Gly Ala Gly His Glu Glu Pro Met Leu Met Gln Ser Tyr Gly Trp<br>　　 2635　　　　　　　 2640　　　　　　　 2645 | | 8039 |
| aac ctg gtc tcc atg aag agt gga gtg gac gtg ttt tac aaa cct<br>Asn Leu Val Ser Met Lys Ser Gly Val Asp Val Phe Tyr Lys Pro<br>2650　　　　　　　 2655　　　　　　　 2660 | | 8084 |
| tca gag ccc agt gac act ctg ttc tgc gac ata ggg gaa tcc tcc<br>Ser Glu Pro Ser Asp Thr Leu Phe Cys Asp Ile Gly Glu Ser Ser<br>　　 2665　　　　　　　 2670　　　　　　　 2675 | | 8129 |
| ccg agt cca gaa gta gaa gaa caa gcg aca cta cgc gtc cta gag<br>Pro Ser Pro Glu Val Glu Glu Gln Arg Thr Leu Arg Val Leu Glu<br>2680　　　　　　　 2685　　　　　　　 2690 | | 8174 |

| | | | | | | | | | | | |
|---|---|---|---|---|---|---|---|---|---|---|---|
| atg | aca | tct | gac | tgg | ttg | cac | cga | gga | cct | aga | gag | ttc | tgt | ata | 8219 |
| Met | Thr | Ser | Asp | Trp | Leu | His | Arg | Gly | Pro | Arg | Glu | Phe | Cys | Ile | |
| | 2695 | | | | 2700 | | | | | 2705 | | | | | |

```
atg aca tct gac tgg ttg cac cga gga cct aga gag ttc tgt ata    8219
Met Thr Ser Asp Trp Leu His Arg Gly Pro Arg Glu Phe Cys Ile
    2695                2700                2705 aaa gtt ctt tgc ccc tac atg ccc aag gtt ata gaa aaa atg gaa    8264
Lys Val Leu Cys Pro Tyr Met Pro Lys Val Ile Glu Lys Met Glu
    2710                2715                2720 gtc ctg caa cgc cgc ttc gga ggt ggg cta gtg cgt ctt ccc ctg    8309
Val Leu Gln Arg Arg Phe Gly Gly Gly Leu Val Arg Leu Pro Leu
    2725                2730                2735 tcc cgc aac tcc aat cac gag atg tac tgg gtt agt gga gcc gct    8354
Ser Arg Asn Ser Asn His Glu Met Tyr Trp Val Ser Gly Ala Ala
    2740                2745                2750 ggc aat gtg gtg cac gct gtg aac atg acc agc cag gta cta ctg    8399
Gly Asn Val Val His Ala Val Asn Met Thr Ser Gln Val Leu Leu
    2755                2760                2765 ggg cga atg gat cgc aca gtg tgg aga ggg cca aag tat gag gaa    8444
Gly Arg Met Asp Arg Thr Val Trp Arg Gly Pro Lys Tyr Glu Glu
    2770                2775                2780 gat gtc aac tta ggg agc gga aca aga gcc gtg gga aag gga gaa    8489
Asp Val Asn Leu Gly Ser Gly Thr Arg Ala Val Gly Lys Gly Glu
    2785                2790                2795 gtc cat agc aat cag gag aaa atc aag aag aga atc cag aag ctt    8534
Val His Ser Asn Gln Glu Lys Ile Lys Lys Arg Ile Gln Lys Leu
    2800                2805                2810 aaa gaa gaa ttc gcc aca acg tgg cac aaa gac cct gag cat cca    8579
Lys Glu Glu Phe Ala Thr Thr Trp His Lys Asp Pro Glu His Pro
    2815                2820                2825 tac cgc act tgg aca tac cac gga agc tat gaa gtg aag gct act    8624
Tyr Arg Thr Trp Thr Tyr His Gly Ser Tyr Glu Val Lys Ala Thr
    2830                2835                2840 ggc tca gct agt tct ctc gtc aac gga gtg gtg aag ctc atg agc    8669
Gly Ser Ala Ser Ser Leu Val Asn Gly Val Val Lys Leu Met Ser
    2845                2850                2855 aaa cct tgg gac gcc att gcc aac gtc acc acc atg gcc atg act    8714
Lys Pro Trp Asp Ala Ile Ala Asn Val Thr Thr Met Ala Met Thr
    2860                2865                2870 gac acc acc cct ttt gga cag caa aga gtt ttc aag gag aaa gtt    8759
Asp Thr Thr Pro Phe Gly Gln Gln Arg Val Phe Lys Glu Lys Val
    2875                2880                2885 gac acg aag gct cct gag cca cca gct gga gct aag gaa gtg ctc    8804
Asp Thr Lys Ala Pro Glu Pro Pro Ala Gly Ala Lys Glu Val Leu
    2890                2895                2900 aac gag acc acc aac tgg ctg tgg gcc tac ttg tca cgg gaa aaa    8849
Asn Glu Thr Thr Asn Trp Leu Trp Ala Tyr Leu Ser Arg Glu Lys
    2905                2910                2915 aga ccc cgc ttg tgc acc aag gaa gaa ttc ata aag aaa gtc aat    8894
Arg Pro Arg Leu Cys Thr Lys Glu Glu Phe Ile Lys Lys Val Asn
    2920                2925                2930 agc aac gcg gct ctt gga gca gtg ttc gct gaa cag aat caa tgg    8939
Ser Asn Ala Ala Leu Gly Ala Val Phe Ala Glu Gln Asn Gln Trp
    2935                2940                2945 agc acg gcg cgt gag gct gtg gat gac ccg cgg ttt tgg gag atg    8984
Ser Thr Ala Arg Glu Ala Val Asp Asp Pro Arg Phe Trp Glu Met
    2950                2955                2960 gtt gat gaa gag agg gaa aac cat ctg cga gga gag tgt cac aca    9029
Val Asp Glu Glu Arg Glu Asn His Leu Arg Gly Glu Cys His Thr
    2965                2970                2975 tgt atc tat aac atg atg gga aaa aga gag aag aag cct gga gag    9074
Cys Ile Tyr Asn Met Met Gly Lys Arg Glu Lys Lys Pro Gly Glu
    2980                2985                2990
```

-continued

| | | | | | | | | | | |
|---|---|---|---|---|---|---|---|---|---|---|
| ttt<br>Phe<br>2995 | gga<br>Gly | aaa<br>Lys | gct<br>Ala | aaa<br>Lys | gga<br>Gly | agc<br>Ser<br>3000 | agg<br>Arg | gcc<br>Ala | att<br>Ile | tgg<br>Trp | ttc<br>Phe<br>3005 | atg<br>Met | tgg<br>Trp | ctt<br>Leu | 9119 |
| gga<br>Gly | gca<br>Ala<br>3010 | cgg<br>Arg | tat<br>Tyr | cta<br>Leu | gag<br>Glu | ttt<br>Phe<br>3015 | gaa<br>Glu | gct<br>Ala | ttg<br>Leu | ggg<br>Gly | ttc<br>Phe<br>3020 | ctg<br>Leu | aat<br>Asn | gaa<br>Glu | 9164 |
| gat<br>Asp | cat<br>His<br>3025 | tgg<br>Trp | ctg<br>Leu | agc<br>Ser | cga<br>Arg | gag<br>Glu<br>3030 | aat<br>Asn | tca<br>Ser | gga<br>Gly | ggt<br>Gly | gga<br>Gly<br>3035 | gtg<br>Val | gaa<br>Glu | ggc<br>Gly | 9209 |
| tca<br>Ser | ggc<br>Gly<br>3040 | gtc<br>Val | caa<br>Gln | aag<br>Lys | ctg<br>Leu | gga<br>Gly<br>3045 | tac<br>Tyr | atc<br>Ile | ctc<br>Leu | cgt<br>Arg | gat<br>Asp<br>3050 | ata<br>Ile | gca<br>Ala | gga<br>Gly | 9254 |
| aag<br>Lys | caa<br>Gln<br>3055 | gga<br>Gly | gga<br>Gly | aaa<br>Lys | atg<br>Met | tac<br>Tyr<br>3060 | gct<br>Ala | gat<br>Asp | gat<br>Asp | acc<br>Thr | gcc<br>Ala<br>3065 | ggg<br>Gly | tgg<br>Trp | gac<br>Asp | 9299 |
| act<br>Thr | aga<br>Arg<br>3070 | att<br>Ile | acc<br>Thr | aga<br>Arg | act<br>Thr | gat<br>Asp<br>3075 | tta<br>Leu | gaa<br>Glu | aat<br>Asn | gaa<br>Glu | gcc<br>Ala<br>3080 | aag<br>Lys | gtg<br>Val | ctg<br>Leu | 9344 |
| gag<br>Glu | ctt<br>Leu<br>3085 | cta<br>Leu | gac<br>Asp | ggt<br>Gly | gaa<br>Glu | cac<br>His<br>3090 | cgc<br>Arg | atg<br>Met | ctc<br>Leu | gcc<br>Ala | cga<br>Arg<br>3095 | gcc<br>Ala | ata<br>Ile | att<br>Ile | 9389 |
| gaa<br>Glu | ttg<br>Leu<br>3100 | act<br>Thr | tac<br>Tyr | agg<br>Arg | cac<br>His | aaa<br>Lys<br>3105 | gtg<br>Val | gtc<br>Val | aag<br>Lys | gtc<br>Val | atg<br>Met<br>3110 | aga<br>Arg | cct<br>Pro | gca<br>Ala | 9434 |
| gca<br>Ala | gaa<br>Glu<br>3115 | gga<br>Gly | aag<br>Lys | acc<br>Thr | gtg<br>Val | atg<br>Met<br>3120 | gac<br>Asp | gtg<br>Val | ata<br>Ile | tca<br>Ser | agg<br>Arg<br>3125 | gag<br>Glu | gat<br>Asp | caa<br>Gln | 9479 |
| agg<br>Arg | ggg<br>Gly<br>3130 | agt<br>Ser | gga<br>Gly | cag<br>Gln | gtg<br>Val | gtc<br>Val<br>3135 | act<br>Thr | tat<br>Tyr | gct<br>Ala | ctt<br>Leu | aac<br>Asn<br>3140 | act<br>Thr | ttc<br>Phe | acg<br>Thr | 9524 |
| aac<br>Asn | atc<br>Ile<br>3145 | gct<br>Ala | gtc<br>Val | cag<br>Gln | ctc<br>Leu | gtc<br>Val<br>3150 | agg<br>Arg | ctg<br>Leu | atg<br>Met | gag<br>Glu | gct<br>Ala<br>3155 | gag<br>Glu | ggg<br>Gly | gtc<br>Val | 9569 |
| att<br>Ile | gga<br>Gly<br>3160 | cca<br>Pro | caa<br>Gln | cac<br>His | ttg<br>Leu | gaa<br>Glu<br>3165 | cag<br>Gln | cta<br>Leu | cct<br>Pro | aga<br>Arg | aaa<br>Lys<br>3170 | aac<br>Asn | aag<br>Lys | ata<br>Ile | 9614 |
| gct<br>Ala | gtc<br>Val<br>3175 | agg<br>Arg | acc<br>Thr | tgg<br>Trp | ctc<br>Leu | ttt<br>Phe<br>3180 | gag<br>Glu | aat<br>Asn | gga<br>Gly | gag<br>Glu | gag<br>Glu<br>3185 | aga<br>Arg | gtg<br>Val | tcc<br>Ser | 9659 |
| agg<br>Arg | atg<br>Met<br>3190 | gct<br>Ala | atc<br>Ile | agc<br>Ser | gga<br>Gly | gac<br>Asp<br>3195 | gac<br>Asp | tgt<br>Cys | gtc<br>Val | gtc<br>Val | aag<br>Lys<br>3200 | ccg<br>Pro | ctg<br>Leu | gac<br>Asp | 9704 |
| gac<br>Asp | aga<br>Arg<br>3205 | ttc<br>Phe | gcc<br>Ala | acg<br>Thr | gcc<br>Ala | ctc<br>Leu<br>3210 | cac<br>His | ttc<br>Phe | ctc<br>Leu | aac<br>Asn | gca<br>Ala<br>3215 | atg<br>Met | tca<br>Ser | aag<br>Lys | 9749 |
| gtc<br>Val | aga<br>Arg<br>3220 | aaa<br>Lys | gac<br>Asp | atc<br>Ile | cag<br>Gln | gaa<br>Glu<br>3225 | tgg<br>Trp | aag<br>Lys | cct<br>Pro | tca<br>Ser | cat<br>His<br>3230 | ggc<br>Gly | tgg<br>Trp | cac<br>His | 9794 |
| gat<br>Asp | tgg<br>Trp<br>3235 | cag<br>Gln | caa<br>Gln | gtt<br>Val | ccc<br>Pro | ttc<br>Phe<br>3240 | tgc<br>Cys | tct<br>Ser | aac<br>Asn | cat<br>His | ttt<br>Phe<br>3245 | cag<br>Gln | gag<br>Glu | att<br>Ile | 9839 |
| gtg<br>Val | atg<br>Met<br>3250 | aaa<br>Lys | gat<br>Asp | gga<br>Gly | agg<br>Arg | agt<br>Ser<br>3255 | ata<br>Ile | gtt<br>Val | gtc<br>Val | ccg<br>Pro | tgc<br>Cys<br>3260 | aga<br>Arg | gga<br>Gly | cag<br>Gln | 9884 |
| gat<br>Asp | gag<br>Glu<br>3265 | ctg<br>Leu | ata<br>Ile | ggc<br>Gly | agg<br>Arg | gct<br>Ala<br>3270 | cgc<br>Arg | atc<br>Ile | tcc<br>Ser | cca<br>Pro | gga<br>Gly<br>3275 | gct<br>Ala | gga<br>Gly | tgg<br>Trp | 9929 |
| aat<br>Asn | gtg<br>Val<br>3280 | aag<br>Lys | gac<br>Asp | aca<br>Thr | gct<br>Ala | tgt<br>Cys<br>3285 | ctg<br>Leu | gcc<br>Ala | aaa<br>Lys | gca<br>Ala | tat<br>Tyr<br>3290 | gca<br>Ala | cag<br>Gln | atg<br>Met | 9974 |

```
tgg cta ctc cta tac ttc cat cgt agg gac ttg cgt ctc atg gca      10019
Trp Leu Leu Leu Tyr Phe His Arg Arg Asp Leu Arg Leu Met Ala
    3295                3300                3305 aat gcg att tgc tca gca gtg cca gtg gat tgg gtg ccc acg ggc      10064
Asn Ala Ile Cys Ser Ala Val Pro Val Asp Trp Val Pro Thr Gly
    3310                3315                3320 agg aca tcc tgg tcg ata cac tcg aaa gga gag tgg atg acc aca      10109
Arg Thr Ser Trp Ser Ile His Ser Lys Gly Glu Trp Met Thr Thr
    3325                3330                3335 gaa gac atg ctg cag gtc tgg aac aga gtc tgg att gaa gaa aat      10154
Glu Asp Met Leu Gln Val Trp Asn Arg Val Trp Ile Glu Glu Asn
    3340                3345                3350 gaa tgg atg gtg gac aag act cca ata aca agc tgg aca gac gtt      10199
Glu Trp Met Val Asp Lys Thr Pro Ile Thr Ser Trp Thr Asp Val
    3355                3360                3365 ccg tat gtg gga aag cgg gag gac atc tgg tgt ggc aac ctc atc      10244
Pro Tyr Val Gly Lys Arg Glu Asp Ile Trp Cys Gly Asn Leu Ile
    3370                3375                3380 gga acg cga tcc aga gca acc tgg gct gag aac atc tac gcg gcg      10289
Gly Thr Arg Ser Arg Ala Thr Trp Ala Glu Asn Ile Tyr Ala Ala
    3385                3390                3395 ata aac cag gtt aga gct gtc att ggg aaa gaa aat tat gtt gac      10334
Ile Asn Gln Val Arg Ala Val Ile Gly Lys Glu Asn Tyr Val Asp
    3400                3405                3410 tac atg acc tca ctc agg aga tac gaa gat gtc ttg atc cag gaa      10379
Tyr Met Thr Ser Leu Arg Arg Tyr Glu Asp Val Leu Ile Gln Glu
    3415                3420                3425 gac agg gtc atc tagtgtgatt taaggtggaa aagcagatta tgtaaataat      10431
Asp Arg Val Ile
    3430 gtaaatgaga aaatgcatgc atatggagtc aggccagcaa aagctgccac cggatactgg    10491 gtagacggtg ctgtctgcgt cccagtccca ggaggactgg gttaacaaat ctgacaacag    10551 aaagtgagaa aaccctcaga accgtctcgg aagcaggtcc ctgctcactg aagttgaag     10611 gaccaacgtc aggccacaaa tttgtgccac tccgctgagg agtgcggcct gcgcagcccc    10671 aggaggactg ggttaccaaa gccgttgagc ccccacggcc caagcctcgt ctaggatgca    10731 atagacgagg tgtaaggact agaggttaga ggagaccccg tggaaacaac aacatgcggc    10791 ccaagccccc tccaagctgt agaggaggtg gaaggactag aggttagagg agaccccgca    10851 tttgcatcaa acagcatatt gacacctggg aatagactgg gagatcttct gctctatctc    10911 aacatcagct actaggcaca gagcgccgaa gtatgtagct ggtggtgagg aagaacacag    10971 gatct                                                                10976
```

<210> SEQ ID NO 2
<211> LENGTH: 3432
<212> TYPE: PRT
<213> ORGANISM: Japanese encephalitis virus

<400> SEQUENCE: 2

```
Met Thr Lys Lys Pro Gly Gly Pro Gly Lys Asn Arg Ala Ile Asn Met
1               5                   10                  15

Leu Lys Arg Gly Leu Pro Arg Val Phe Pro Leu Val Gly Val Lys Arg
                20                  25                  30

Val Val Met Ser Leu Leu Asp Gly Arg Gly Pro Val Arg Phe Val Leu
            35                  40                  45

Ala Leu Ile Thr Phe Phe Lys Phe Thr Ala Leu Ala Pro Thr Lys Ala
        50                  55                  60
```

```
Leu Leu Gly Arg Trp Lys Ala Val Glu Lys Ser Val Ala Met Lys His
 65                  70                  75                  80

Leu Thr Ser Phe Lys Arg Glu Leu Gly Thr Leu Ile Asp Ala Val Asn
                 85                  90                  95

Lys Arg Gly Arg Lys Gln Asn Lys Arg Gly Asn Glu Gly Ser Ile
            100                 105                 110

Met Trp Leu Ala Ser Leu Ala Val Val Ile Ala Cys Ala Gly Ala Ile
            115                 120                 125

Lys Leu Ser Asn Phe Gln Gly Lys Leu Leu Met Thr Ile Asn Asn Thr
130                 135                 140

Asp Ile Ala Asp Val Ile Val Ile Pro Thr Ser Lys Gly Glu Asn Arg
145                 150                 155                 160

Cys Trp Val Arg Ala Ile Asp Val Gly Tyr Met Cys Glu Asp Thr Ile
                165                 170                 175

Thr Tyr Glu Cys Pro Lys Leu Ala Met Gly Asn Asp Pro Glu Asp Val
            180                 185                 190

Asp Cys Trp Cys Asp Asn Gln Glu Val Tyr Val Gln Tyr Gly Arg Cys
            195                 200                 205

Thr Arg Thr Arg His Ser Lys Arg Ser Arg Arg Ser Val Ser Val Gln
            210                 215                 220

Thr His Gly Glu Ser Ser Leu Val Asn Lys Lys Glu Ala Trp Leu Asp
225                 230                 235                 240

Ser Thr Lys Ala Thr Arg Tyr Leu Met Lys Thr Glu Asn Trp Ile Ile
                245                 250                 255

Arg Asn Pro Gly Tyr Ala Phe Leu Ala Ala Val Leu Gly Trp Met Leu
            260                 265                 270

Gly Ser Thr Asn Gly Gln Arg Val Val Phe Thr Ile Leu Leu Leu Leu
            275                 280                 285

Val Ala Pro Ala Tyr Ser Phe Asn Cys Leu Gly Met Gly Asn Arg Asp
290                 295                 300

Phe Ile Glu Gly Ala Ser Gly Ala Thr Trp Val Asp Leu Val Leu Glu
305                 310                 315                 320

Gly Asp Ser Cys Leu Thr Ile Met Ala Asn Asp Lys Pro Thr Leu Asp
                325                 330                 335

Val Arg Met Ile Asn Ile Glu Ala Ser Gln Leu Ala Glu Val Arg Ser
            340                 345                 350

Tyr Cys Tyr His Ala Ser Val Thr Asp Ile Ser Thr Val Ala Arg Cys
            355                 360                 365

Pro Thr Thr Gly Glu Ala His Asn Glu Lys Arg Ala Asp Ser Ser Tyr
370                 375                 380

Val Cys Lys Gln Gly Phe Thr Asp Arg Gly Trp Gly Asn Gly Cys Gly
385                 390                 395                 400

Leu Phe Gly Lys Gly Ser Ile Asp Thr Cys Ala Lys Phe Ser Cys Thr
                405                 410                 415

Ser Lys Ala Ile Gly Arg Thr Ile Gln Pro Glu Asn Ile Lys Tyr Lys
            420                 425                 430

Val Gly Ile Phe Val His Gly Ala Thr Thr Ser Glu Asn His Gly Asn
            435                 440                 445

Tyr Ser Ala Gln Val Gly Ala Ser Gln Ala Ala Lys Phe Thr Val Thr
            450                 455                 460

Pro Asn Ala Pro Ser Ile Thr Leu Lys Leu Gly Asp Tyr Gly Glu Val
465                 470                 475                 480

Thr Leu Asp Cys Glu Pro Arg Ser Gly Leu Asn Thr Glu Ala Phe Tyr
```

```
                        485                 490                 495
Val Met Thr Val Gly Ser Lys Ser Phe Leu Val His Arg Glu Trp Phe
                    500                 505                 510

His Asp Leu Ala Leu Pro Trp Thr Ser Pro Ser Ser Thr Ala Trp Arg
            515                 520                 525

Asn Arg Glu Leu Leu Met Glu Phe Glu Glu Ala His Ala Thr Lys Gln
        530                 535                 540

Ser Val Val Ala Leu Gly Ser Gln Glu Gly Leu His Gln Ala Leu
545                 550                 555                 560

Ala Gly Ala Ile Val Val Glu Tyr Ser Ser Val Lys Leu Thr Ser
                565                 570                 575

Gly His Leu Lys Cys Arg Leu Lys Met Asp Lys Leu Ala Leu Lys Gly
            580                 585                 590

Thr Thr Tyr Gly Met Cys Thr Glu Lys Phe Ser Phe Ala Lys Asn Pro
        595                 600                 605

Ala Asp Thr Gly His Gly Thr Val Val Ile Glu Leu Ser Tyr Ser Gly
    610                 615                 620

Ser Asp Gly Pro Cys Lys Ile Pro Ile Val Ser Val Ala Ser Leu Asn
625                 630                 635                 640

Asp Met Thr Pro Val Gly Arg Leu Val Thr Val Asn Pro Phe Val Ala
                645                 650                 655

Thr Ser Ser Ala Asn Ser Lys Val Leu Val Glu Met Glu Pro Pro Phe
            660                 665                 670

Gly Asp Ser Tyr Ile Val Val Gly Arg Gly Asp Lys Gln Ile Asn His
        675                 680                 685

His Trp His Lys Ala Gly Ser Thr Leu Gly Lys Ala Phe Ser Thr Thr
    690                 695                 700

Leu Lys Gly Ala Gln Arg Leu Ala Ala Leu Gly Asp Thr Ala Trp Asp
705                 710                 715                 720

Phe Gly Ser Ile Gly Gly Val Phe Asn Ser Ile Gly Lys Ala Val His
                725                 730                 735

Gln Val Phe Gly Gly Ala Phe Arg Thr Leu Phe Gly Gly Met Ser Trp
            740                 745                 750

Ile Thr Gln Gly Leu Met Gly Ala Leu Leu Leu Trp Met Gly Val Asn
        755                 760                 765

Ala Arg Asp Arg Ser Ile Ala Leu Ala Phe Leu Ala Thr Gly Gly Val
    770                 775                 780

Leu Val Phe Leu Ala Thr Asn Val His Ala Asp Thr Gly Cys Ala Ile
785                 790                 795                 800

Asp Ile Thr Arg Lys Glu Met Arg Cys Gly Ser Gly Ile Phe Val His
                805                 810                 815

Asn Asp Val Glu Ala Trp Val Asp Arg Tyr Lys Tyr Leu Pro Glu Thr
            820                 825                 830

Pro Arg Ser Leu Ala Lys Ile Val His Lys Ala His Lys Glu Gly Val
        835                 840                 845

Cys Gly Val Arg Ser Val Thr Arg Leu Glu His Gln Met Trp Glu Ala
    850                 855                 860

Val Arg Asp Glu Leu Asn Val Leu Leu Lys Glu Asn Ala Val Asp Leu
865                 870                 875                 880

Ser Val Val Val Asn Lys Pro Val Gly Arg Tyr Arg Ser Ala Pro Lys
                885                 890                 895

Arg Leu Ser Met Thr Gln Glu Lys Phe Glu Met Gly Trp Lys Ala Trp
            900                 905                 910
```

-continued

```
Gly Lys Ser Ile Leu Phe Ala Pro Glu Leu Ala Asn Ser Thr Phe Val
        915                 920                 925

Val Asp Gly Pro Glu Thr Lys Glu Cys Pro Asp Glu His Arg Ala Trp
    930                 935                 940

Asn Ser Met Gln Ile Glu Asp Phe Gly Phe Gly Ile Thr Ser Thr Arg
945                 950                 955                 960

Val Trp Leu Lys Ile Arg Glu Glu Ser Thr Asp Glu Cys Asp Gly Ala
                965                 970                 975

Ile Ile Gly Thr Ala Val Lys Gly His Val Ala Val His Ser Asp Leu
            980                 985                 990

Ser Tyr Trp Ile Glu Ser Arg Tyr Asn Asp Thr Trp Lys Leu Glu Arg
        995                 1000                1005

Ala Val Phe Gly Glu Val Lys Ser Cys Thr Trp Pro Glu Thr His
    1010                1015                1020

Thr Leu Trp Gly Asp Gly Val Glu Glu Ser Glu Leu Ile Ile Pro
    1025                1030                1035

His Thr Ile Ala Gly Pro Lys Ser Lys His Asn Arg Arg Glu Gly
    1040                1045                1050

Tyr Lys Thr Gln Asn Gln Gly Pro Trp Asp Glu Asn Gly Ile Val
    1055                1060                1065

Leu Asp Phe Asp Tyr Cys Pro Gly Thr Lys Val Thr Ile Thr Glu
    1070                1075                1080

Asp Cys Gly Lys Arg Gly Pro Ser Val Arg Thr Thr Thr Asp Ser
    1085                1090                1095

Gly Lys Leu Ile Thr Asp Trp Cys Cys Arg Ser Cys Ser Leu Pro
    1100                1105                1110

Pro Leu Arg Phe Arg Thr Glu Asn Gly Cys Trp Tyr Gly Met Glu
    1115                1120                1125

Ile Arg Pro Val Arg His Asp Glu Thr Thr Leu Val Arg Ser Gln
    1130                1135                1140

Val Asp Ala Phe Asn Gly Glu Met Val Asp Pro Phe Gln Leu Gly
    1145                1150                1155

Leu Leu Val Met Phe Leu Ala Thr Gln Glu Val Leu Arg Lys Arg
    1160                1165                1170

Trp Thr Ala Arg Leu Thr Ile Pro Ala Val Leu Gly Ala Leu Leu
    1175                1180                1185

Val Leu Met Leu Gly Gly Ile Thr Tyr Thr Asp Leu Ala Arg Tyr
    1190                1195                1200

Val Val Leu Val Ala Ala Ser Phe Ala Glu Ala Asn Ser Gly Gly
    1205                1210                1215

Asp Val Leu His Leu Ala Leu Ile Ala Val Phe Lys Ile Gln Pro
    1220                1225                1230

Ala Phe Leu Val Met Asn Met Leu Ser Thr Arg Trp Thr Asn Gln
    1235                1240                1245

Glu Asn Val Val Leu Val Leu Gly Ala Ala Phe Phe Gln Leu Ala
    1250                1255                1260

Ser Val Asp Leu Gln Ile Gly Val His Gly Ile Leu Asn Ala Ala
    1265                1270                1275

Ala Ile Ala Trp Met Ile Val Arg Ala Ile Thr Phe Pro Thr Thr
    1280                1285                1290

Ser Ser Val Thr Met Pro Val Leu Ala Leu Leu Thr Pro Gly Met
    1295                1300                1305

Arg Ala Leu Tyr Leu Asp Thr Tyr Arg Ile Ile Leu Leu Val Ile
    1310                1315                1320
```

```
Gly Ile Cys Ser Leu Leu Gln Glu Arg Lys Lys Thr Met Ala Lys
    1325                1330                1335

Lys Lys Gly Ala Val Leu Leu Gly Leu Ala Leu Thr Ser Thr Gly
    1340                1345                1350

Trp Phe Ser Pro Thr Thr Ile Ala Ala Gly Leu Met Val Cys Asn
    1355                1360                1365

Pro Asn Lys Lys Arg Gly Trp Pro Ala Thr Glu Phe Leu Ser Ala
    1370                1375                1380

Val Gly Leu Met Phe Ala Ile Val Gly Gly Leu Ala Glu Leu Asp
    1385                1390                1395

Ile Glu Ser Met Ser Ile Pro Phe Met Leu Ala Gly Leu Met Ala
    1400                1405                1410

Val Ser Tyr Val Val Ser Gly Lys Ala Thr Asp Met Trp Leu Glu
    1415                1420                1425

Arg Ala Ala Asp Ile Ser Trp Glu Met Asp Ala Ala Ile Thr Gly
    1430                1435                1440

Ser Ser Arg Arg Leu Asp Val Lys Leu Asp Asp Asp Gly Asp Phe
    1445                1450                1455

His Leu Ile Asp Asp Pro Gly Val Pro Trp Lys Val Trp Val Leu
    1460                1465                1470

Arg Met Ser Cys Ile Gly Leu Ala Ala Leu Thr Pro Trp Ala Ile
    1475                1480                1485

Val Pro Ala Ala Phe Gly Tyr Trp Leu Thr Leu Lys Thr Thr Lys
    1490                1495                1500

Arg Gly Gly Val Phe Trp Asp Thr Pro Ser Pro Lys Pro Cys Ser
    1505                1510                1515

Lys Gly Asp Thr Thr Thr Gly Val Tyr Arg Ile Met Ala Arg Gly
    1520                1525                1530

Ile Leu Gly Thr Tyr Gln Ala Gly Val Gly Val Met Tyr Glu Asn
    1535                1540                1545

Val Phe His Thr Leu Trp His Thr Thr Arg Gly Ala Ala Ile Met
    1550                1555                1560

Ser Gly Glu Gly Lys Leu Thr Pro Tyr Trp Gly Ser Val Lys Glu
    1565                1570                1575

Asp Arg Ile Ala Tyr Gly Gly Pro Trp Arg Phe Asp Arg Lys Trp
    1580                1585                1590

Asn Gly Thr Asp Asp Val Gln Val Ile Val Val Glu Pro Gly Lys
    1595                1600                1605

Ala Ala Val Asn Ile Gln Thr Lys Pro Gly Val Phe Arg Thr Pro
    1610                1615                1620

Phe Gly Glu Val Gly Ala Val Ser Leu Asp Tyr Pro Arg Gly Thr
    1625                1630                1635

Ser Gly Ser Pro Ile Leu Asp Ser Asn Gly Asp Ile Ile Gly Leu
    1640                1645                1650

Tyr Gly Asn Gly Val Glu Leu Gly Asp Gly Ser Tyr Val Ser Ala
    1655                1660                1665

Ile Val Gln Gly Asp Arg Gln Glu Glu Pro Val Pro Glu Ala Tyr
    1670                1675                1680

Thr Pro Asn Met Leu Arg Lys Arg Gln Met Thr Val Leu Asp Leu
    1685                1690                1695

His Pro Gly Ser Gly Lys Thr Lys Lys Ile Leu Pro Gln Ile Ile
    1700                1705                1710

Lys Asp Ala Ile Gln Gln Arg Leu Arg Thr Ala Val Leu Ala Pro
```

-continued

```
                1715                1720                1725

Thr Arg Val Val Ala Ala Glu Met Ala Glu Ala Leu Arg Gly Leu
    1730                1735                1740

Pro Val Arg Tyr Gln Thr Ser Ala Val Gln Arg Glu His Gln Gly
    1745                1750                1755

Asn Glu Ile Val Asp Val Met Cys His Ala Thr Leu Thr His Arg
    1760                1765                1770

Leu Met Ser Pro Asn Arg Val Pro Asn Tyr Asn Leu Phe Val Met
    1775                1780                1785

Asp Glu Ala His Phe Thr Asp Pro Ala Ser Ile Ala Ala Arg Gly
    1790                1795                1800

Tyr Ile Ala Thr Lys Val Glu Leu Gly Glu Ala Ala Ala Ile Phe
    1805                1810                1815

Met Thr Ala Thr Pro Pro Gly Thr Thr Asp Pro Phe Pro Asp Ser
    1820                1825                1830

Asn Ala Pro Ile His Asp Leu Gln Asp Glu Ile Pro Asp Arg Ala
    1835                1840                1845

Trp Ser Ser Gly Tyr Glu Trp Ile Thr Glu Tyr Ala Gly Lys Thr
    1850                1855                1860

Val Trp Phe Val Ala Ser Val Lys Met Gly Asn Glu Ile Ala Met
    1865                1870                1875

Cys Leu Gln Arg Ala Gly Lys Lys Val Ile Gln Leu Asn Arg Lys
    1880                1885                1890

Ser Tyr Asp Thr Glu Tyr Pro Lys Cys Lys Asn Gly Asp Trp Asp
    1895                1900                1905

Phe Val Ile Thr Thr Asp Ile Ser Glu Met Gly Ala Asn Phe Gly
    1910                1915                1920

Ala Ser Arg Val Ile Asp Cys Arg Lys Ser Val Lys Pro Thr Ile
    1925                1930                1935

Leu Glu Glu Gly Glu Gly Arg Val Ile Leu Gly Asn Pro Ser Pro
    1940                1945                1950

Ile Thr Ser Ala Ser Ala Ala Gln Arg Arg Gly Arg Val Gly Arg
    1955                1960                1965

Asn Pro Asn Gln Val Gly Asp Glu Tyr His Tyr Gly Gly Ala Thr
    1970                1975                1980

Ser Glu Asp Asp Ser Asn Leu Ala His Trp Thr Glu Ala Lys Ile
    1985                1990                1995

Met Leu Asp Asn Ile His Met Pro Asn Gly Leu Val Ala Gln Leu
    2000                2005                2010

Tyr Gly Pro Glu Arg Glu Lys Ala Phe Thr Met Asp Gly Glu Tyr
    2015                2020                2025

Arg Leu Arg Gly Glu Glu Lys Lys Asn Phe Leu Glu Leu Leu Arg
    2030                2035                2040

Thr Ala Asp Leu Pro Val Trp Leu Ala Tyr Lys Val Ala Ser Asn
    2045                2050                2055

Gly Ile Gln Tyr Thr Asp Arg Lys Trp Cys Phe Asp Gly Pro Arg
    2060                2065                2070

Thr Asn Ala Ile Leu Glu Asp Asn Thr Glu Val Glu Ile Val Thr
    2075                2080                2085

Arg Met Gly Glu Arg Lys Ile Leu Lys Pro Arg Trp Leu Asp Ala
    2090                2095                2100

Arg Val Tyr Ala Asp His Gln Ala Leu Lys Trp Phe Lys Asp Phe
    2105                2110                2115
```

-continued

```
Ala Ala Gly Lys Arg Ser Ala Val Ser Phe Ile Glu Val Leu Gly
2120                2125                2130

Arg Met Pro Glu His Phe Met Gly Lys Thr Arg Glu Ala Leu Asp
2135                2140                2145

Thr Met Tyr Leu Val Ala Thr Ala Glu Lys Gly Gly Lys Ala His
2150                2155                2160

Arg Met Ala Leu Glu Glu Leu Pro Asp Ala Leu Glu Thr Ile Thr
2165                2170                2175

Leu Ile Val Ala Ile Thr Val Met Thr Gly Gly Phe Phe Leu Leu
2180                2185                2190

Met Met Gln Arg Lys Gly Ile Gly Lys Met Gly Leu Gly Ala Leu
2195                2200                2205

Val Leu Thr Leu Ala Thr Phe Phe Leu Trp Ala Ala Glu Val Pro
2210                2215                2220

Gly Thr Lys Ile Ala Gly Thr Leu Leu Ile Ala Leu Leu Leu Met
2225                2230                2235

Val Val Leu Ile Pro Glu Pro Glu Lys Gln Arg Ser Gln Thr Asp
2240                2245                2250

Asn Gln Leu Ala Val Phe Leu Ile Cys Val Leu Thr Val Val Gly
2255                2260                2265

Val Val Ala Ala Asn Glu Tyr Gly Met Leu Glu Lys Thr Lys Ala
2270                2275                2280

Asp Leu Lys Ser Met Phe Gly Gly Lys Thr Gln Ala Ser Gly Leu
2285                2290                2295

Thr Gly Leu Pro Ser Met Ala Leu Asp Leu Arg Pro Ala Thr Ala
2300                2305                2310

Trp Ala Leu Tyr Gly Gly Ser Thr Val Val Leu Thr Pro Leu Leu
2315                2320                2325

Lys His Leu Ile Thr Ser Glu Tyr Val Thr Thr Ser Leu Ala Ser
2330                2335                2340

Ile Asn Ser Gln Ala Gly Ser Leu Phe Val Leu Pro Arg Gly Val
2345                2350                2355

Pro Phe Thr Asp Leu Asp Leu Thr Val Gly Leu Val Phe Leu Gly
2360                2365                2370

Cys Trp Gly Gln Ile Thr Leu Thr Thr Phe Leu Thr Ala Met Val
2375                2380                2385

Leu Ala Thr Leu His Tyr Gly Tyr Met Leu Pro Gly Trp Gln Ala
2390                2395                2400

Glu Ala Leu Arg Ala Ala Gln Arg Arg Thr Ala Ala Gly Ile Met
2405                2410                2415

Lys Asn Ala Val Val Asp Gly Met Val Ala Thr Asp Val Pro Glu
2420                2425                2430

Leu Glu Arg Thr Thr Pro Leu Met Gln Lys Lys Val Gly Gln Val
2435                2440                2445

Leu Leu Ile Gly Val Ser Val Ala Ala Phe Leu Val Asn Pro Lys
2450                2455                2460

Ile Thr Thr Val Arg Glu Ala Gly Val Leu Val Thr Ala Ala Thr
2465                2470                2475

Leu Ser Leu Trp Asp Asn Gly Ala Ser Ala Val Trp Asn Ser Thr
2480                2485                2490

Thr Ala Thr Gly Leu Cys His Val Met Arg Gly Ser Tyr Leu Ala
2495                2500                2505

Gly Gly Ser Ile Ala Trp Thr Leu Ile Lys Asn Ala Asp Lys Pro
2510                2515                2520
```

```
Ser Leu Lys Arg Gly Arg Pro Gly Gly Arg Thr Leu Gly Glu Gln
    2525                2530                2535

Trp Lys Glu Lys Leu Asn Ala Met Ser Arg Glu Glu Phe Phe Lys
    2540                2545                2550

Tyr Arg Arg Glu Ala Ile Ile Glu Val Asp Arg Thr Glu Ala Arg
    2555                2560                2565

Arg Ala Arg Arg Glu Asn Asn Ile Val Gly Gly His Pro Val Ser
    2570                2575                2580

Arg Gly Ser Ala Lys Leu Arg Trp Leu Val Glu Lys Gly Phe Val
    2585                2590                2595

Ser Pro Ile Gly Lys Val Ile Asp Leu Gly Cys Gly Arg Gly Gly
    2600                2605                2610

Trp Ser Tyr Tyr Ala Ala Thr Leu Lys Lys Val Gln Glu Val Arg
    2615                2620                2625

Gly Tyr Thr Lys Gly Gly Ala Gly His Glu Glu Pro Met Leu Met
    2630                2635                2640

Gln Ser Tyr Gly Trp Asn Leu Val Ser Met Lys Ser Gly Val Asp
    2645                2650                2655

Val Phe Tyr Lys Pro Ser Glu Pro Ser Asp Thr Leu Phe Cys Asp
    2660                2665                2670

Ile Gly Glu Ser Ser Pro Ser Pro Glu Val Glu Glu Gln Arg Thr
    2675                2680                2685

Leu Arg Val Leu Glu Met Thr Ser Asp Trp Leu His Arg Gly Pro
    2690                2695                2700

Arg Glu Phe Cys Ile Lys Val Leu Cys Pro Tyr Met Pro Lys Val
    2705                2710                2715

Ile Glu Lys Met Glu Val Leu Gln Arg Arg Phe Gly Gly Gly Leu
    2720                2725                2730

Val Arg Leu Pro Leu Ser Arg Asn Ser Asn His Glu Met Tyr Trp
    2735                2740                2745

Val Ser Gly Ala Ala Gly Asn Val Val His Ala Val Asn Met Thr
    2750                2755                2760

Ser Gln Val Leu Leu Gly Arg Met Asp Arg Thr Val Trp Arg Gly
    2765                2770                2775

Pro Lys Tyr Glu Glu Asp Val Asn Leu Gly Ser Gly Thr Arg Ala
    2780                2785                2790

Val Gly Lys Gly Glu Val His Ser Asn Gln Glu Lys Ile Lys Lys
    2795                2800                2805

Arg Ile Gln Lys Leu Lys Glu Glu Phe Ala Thr Thr Trp His Lys
    2810                2815                2820

Asp Pro Glu His Pro Tyr Arg Thr Trp Thr Tyr His Gly Ser Tyr
    2825                2830                2835

Glu Val Lys Ala Thr Gly Ser Ala Ser Ser Leu Val Asn Gly Val
    2840                2845                2850

Val Lys Leu Met Ser Lys Pro Trp Asp Ala Ile Ala Asn Val Thr
    2855                2860                2865

Thr Met Ala Met Thr Asp Thr Thr Pro Phe Gly Gln Gln Arg Val
    2870                2875                2880

Phe Lys Glu Lys Val Asp Thr Lys Ala Pro Glu Pro Pro Ala Gly
    2885                2890                2895

Ala Lys Glu Val Leu Asn Glu Thr Thr Asn Trp Leu Trp Ala Tyr
    2900                2905                2910

Leu Ser Arg Glu Lys Arg Pro Arg Leu Cys Thr Lys Glu Glu Phe
```

```
                2915                2920                2925

Ile Lys Lys Val Asn Ser Asn Ala Ala Leu Gly Ala Val Phe Ala
    2930                2935                2940

Glu Gln Asn Gln Trp Ser Thr Ala Arg Glu Ala Val Asp Asp Pro
    2945                2950                2955

Arg Phe Trp Glu Met Val Asp Glu Arg Glu Asn His Leu Arg
    2960                2965                2970

Gly Glu Cys His Thr Cys Ile Tyr Asn Met Met Gly Lys Arg Glu
    2975                2980                2985

Lys Lys Pro Gly Glu Phe Gly Lys Ala Lys Gly Ser Arg Ala Ile
    2990                2995                3000

Trp Phe Met Trp Leu Gly Ala Arg Tyr Leu Glu Phe Glu Ala Leu
    3005                3010                3015

Gly Phe Leu Asn Glu Asp His Trp Leu Ser Arg Glu Asn Ser Gly
    3020                3025                3030

Gly Gly Val Glu Gly Ser Gly Val Gln Lys Leu Gly Tyr Ile Leu
    3035                3040                3045

Arg Asp Ile Ala Gly Lys Gln Gly Gly Lys Met Tyr Ala Asp Asp
    3050                3055                3060

Thr Ala Gly Trp Asp Thr Arg Ile Thr Arg Thr Asp Leu Glu Asn
    3065                3070                3075

Glu Ala Lys Val Leu Glu Leu Leu Asp Gly Glu His Arg Met Leu
    3080                3085                3090

Ala Arg Ala Ile Ile Glu Leu Thr Tyr Arg His Lys Val Val Lys
    3095                3100                3105

Val Met Arg Pro Ala Ala Glu Gly Lys Thr Val Met Asp Val Ile
    3110                3115                3120

Ser Arg Glu Asp Gln Arg Gly Ser Gly Gln Val Val Thr Tyr Ala
    3125                3130                3135

Leu Asn Thr Phe Thr Asn Ile Ala Val Gln Leu Val Arg Leu Met
    3140                3145                3150

Glu Ala Glu Gly Val Ile Gly Pro Gln His Leu Glu Gln Leu Pro
    3155                3160                3165

Arg Lys Asn Lys Ile Ala Val Arg Thr Trp Leu Phe Glu Asn Gly
    3170                3175                3180

Glu Glu Arg Val Ser Arg Met Ala Ile Ser Gly Asp Asp Cys Val
    3185                3190                3195

Val Lys Pro Leu Asp Asp Arg Phe Ala Thr Ala Leu His Phe Leu
    3200                3205                3210

Asn Ala Met Ser Lys Val Arg Lys Asp Ile Gln Glu Trp Lys Pro
    3215                3220                3225

Ser His Gly Trp His Asp Trp Gln Gln Val Pro Phe Cys Ser Asn
    3230                3235                3240

His Phe Gln Glu Ile Val Met Lys Asp Gly Arg Ser Ile Val Val
    3245                3250                3255

Pro Cys Arg Gly Gln Asp Glu Leu Ile Gly Arg Ala Arg Ile Ser
    3260                3265                3270

Pro Gly Ala Gly Trp Asn Val Lys Asp Thr Ala Cys Leu Ala Lys
    3275                3280                3285

Ala Tyr Ala Gln Met Trp Leu Leu Leu Tyr Phe His Arg Arg Asp
    3290                3295                3300

Leu Arg Leu Met Ala Asn Ala Ile Cys Ser Ala Val Pro Val Asp
    3305                3310                3315
```

```
Trp Val Pro Thr Gly Arg Thr Ser Trp Ser Ile His Ser Lys Gly
    3320                3325                3330

Glu Trp Met Thr Thr Glu Asp Met Leu Gln Val Trp Asn Arg Val
    3335                3340                3345

Trp Ile Glu Glu Asn Glu Trp Met Val Asp Lys Thr Pro Ile Thr
    3350                3355                3360

Ser Trp Thr Asp Val Pro Tyr Val Gly Lys Arg Glu Asp Ile Trp
    3365                3370                3375

Cys Gly Asn Leu Ile Gly Thr Arg Ser Arg Ala Thr Trp Ala Glu
    3380                3385                3390

Asn Ile Tyr Ala Ala Ile Asn Gln Val Arg Ala Val Ile Gly Lys
    3395                3400                3405

Glu Asn Tyr Val Asp Tyr Met Thr Ser Leu Arg Arg Tyr Glu Asp
    3410                3415                3420

Val Leu Ile Gln Glu Asp Arg Val Ile
    3425                3430

<210> SEQ ID NO 3
<211> LENGTH: 10976
<212> TYPE: DNA
<213> ORGANISM: Japanese encephalitis virus
<220> FEATURE:
<221> NAME/KEY: CDS
<222> LOCATION: (96)..(10391)

<400> SEQUENCE: 3
agaagtttat ctgtgtgaac ttcttggctt agtatcgttg agaagaatcg agagattagt      60
gcagtttaaa cagtttttta gaacggaaga taacc atg act aaa aaa cca gga        113
                                      Met Thr Lys Lys Pro Gly
                                        1               5 ggg ccc ggt aaa aac cgg gct atc aat atg ctg aaa cgc ggc cta ccc       161
Gly Pro Gly Lys Asn Arg Ala Ile Asn Met Leu Lys Arg Gly Leu Pro
            10                  15                  20 cgc gta ttc cca cta gtg gga gtg aag agg gta gta atg agc ttg ttg       209
Arg Val Phe Pro Leu Val Gly Val Lys Arg Val Val Met Ser Leu Leu
        25                  30                  35 gac ggc aga ggg cca gta cgt ttc gtg ctg gct ctt atc acg ttc ttc       257
Asp Gly Arg Gly Pro Val Arg Phe Val Leu Ala Leu Ile Thr Phe Phe
    40                  45                  50 aag ttt aca gca tta gcc ccg acc aag gcg ctt tta ggc cga tgg aaa       305
Lys Phe Thr Ala Leu Ala Pro Thr Lys Ala Leu Leu Gly Arg Trp Lys
55                  60                  65                  70 gca gtg gaa aag agt gta gca atg aaa cat ctc act agt ttc aaa cga       353
Ala Val Glu Lys Ser Val Ala Met Lys His Leu Thr Ser Phe Lys Arg
                75                  80                  85 gaa ctt gga aca ctc att gac gcc gtg aac aag cgg ggc aga aag caa       401
Glu Leu Gly Thr Leu Ile Asp Ala Val Asn Lys Arg Gly Arg Lys Gln
            90                  95                 100 aac aaa aga gga gga aat gaa ggc tca atc atg tgg ctt gcg agc ttg       449
Asn Lys Arg Gly Gly Asn Glu Gly Ser Ile Met Trp Leu Ala Ser Leu
        105                 110                 115 gca gtt gtc ata gct tgt gca gga gcc atg aag ttg tca aat ttc cag       497
Ala Val Val Ile Ala Cys Ala Gly Ala Met Lys Leu Ser Asn Phe Gln
    120                 125                 130 ggg aag ctt ttg atg acc att aac aac acg gac att gca gac gtt atc       545
Gly Lys Leu Leu Met Thr Ile Asn Asn Thr Asp Ile Ala Asp Val Ile
135                 140                 145                 150 gta att ccc acc tca aaa gga gag aac aga tgc tgg gtc cgg gca atc       593
Val Ile Pro Thr Ser Lys Gly Glu Asn Arg Cys Trp Val Arg Ala Ile
                155                 160                 165
```

```
gac gtc ggc tac atg tgt gag gac act atc acg tac gaa tgt cct aag       641
Asp Val Gly Tyr Met Cys Glu Asp Thr Ile Thr Tyr Glu Cys Pro Lys
        170                 175                 180 ctt gcc atg ggc aat gat cca gag gat gtg gac tgc tgg tgt gac aac       689
Leu Ala Met Gly Asn Asp Pro Glu Asp Val Asp Cys Trp Cys Asp Asn
            185                 190                 195 caa gaa gtc tac gtc caa tat gga cgg tgc acg cgg acc agg cat tcc       737
Gln Glu Val Tyr Val Gln Tyr Gly Arg Cys Thr Arg Thr Arg His Ser
200                 205                 210 aag cga agc agg aga tcc gtg tcg gtc caa aca cat ggg gag agt tca       785
Lys Arg Ser Arg Arg Ser Val Ser Val Gln Thr His Gly Glu Ser Ser
215                 220                 225                 230 cta gtg aat aaa aaa gag gct tgg ctg gat tca acg aaa gcc aca cga       833
Leu Val Asn Lys Lys Glu Ala Trp Leu Asp Ser Thr Lys Ala Thr Arg
            235                 240                 245 tat ctc atg aaa act gag aac tgg atc ata agg aat cct ggc tat gct       881
Tyr Leu Met Lys Thr Glu Asn Trp Ile Ile Arg Asn Pro Gly Tyr Ala
        250                 255                 260 ttc ctg gcg gcg gta ctc ggc tgg atg ctt ggc agt aac aac ggt caa       929
Phe Leu Ala Ala Val Leu Gly Trp Met Leu Gly Ser Asn Asn Gly Gln
            265                 270                 275 cgc gtg gta ttc acc atc ctg ctg ctg gtc gct ccg gct tac agt           977
Arg Val Val Phe Thr Ile Leu Leu Leu Val Ala Pro Ala Tyr Ser
        280                 285                 290 ttt aat tgt ctg gga atg ggc aat cgt gac ttc ata gaa gga gcc agt      1025
Phe Asn Cys Leu Gly Met Gly Asn Arg Asp Phe Ile Glu Gly Ala Ser
295                 300                 305                 310 gga gcc act tgg gtg gac ttg gtg cta gaa gga gat agc tgc ttg aca      1073
Gly Ala Thr Trp Val Asp Leu Val Leu Glu Gly Asp Ser Cys Leu Thr
            315                 320                 325 att atg gca aac gac aaa cca aca ttg gac gtc cgc atg atc aac atc      1121
Ile Met Ala Asn Asp Lys Pro Thr Leu Asp Val Arg Met Ile Asn Ile
        330                 335                 340 gaa gct agc caa ctt gct gag gtt aga agt tac tgt tat cat gct tca      1169
Glu Ala Ser Gln Leu Ala Glu Val Arg Ser Tyr Cys Tyr His Ala Ser
            345                 350                 355 gtc act gac atc tcg acg gtg gct cgg tgc ccc acg act gga gaa gcc      1217
Val Thr Asp Ile Ser Thr Val Ala Arg Cys Pro Thr Thr Gly Glu Ala
        360                 365                 370 cac aac gag aag cga gct gat agt agc tat gtg tgc aaa caa ggc ttc      1265
His Asn Glu Lys Arg Ala Asp Ser Ser Tyr Val Cys Lys Gln Gly Phe
375                 380                 385                 390 act gat cgt ggg tgg ggc aac gga tgt gga ctt ttc ggg aag gga agc      1313
Thr Asp Arg Gly Trp Gly Asn Gly Cys Gly Leu Phe Gly Lys Gly Ser
            395                 400                 405 att gac aca tgt gca aaa ttc tcc tgc acc agc aaa gcg att ggg aga      1361
Ile Asp Thr Cys Ala Lys Phe Ser Cys Thr Ser Lys Ala Ile Gly Arg
        410                 415                 420 aca atc cag cca gaa aac atc aaa tac aaa gtt ggc att ttt gtg cat      1409
Thr Ile Gln Pro Glu Asn Ile Lys Tyr Lys Val Gly Ile Phe Val His
            425                 430                 435 gga gcc act act tcg gaa aac cat ggg aat tat tca gcg caa gtt ggg      1457
Gly Ala Thr Thr Ser Glu Asn His Gly Asn Tyr Ser Ala Gln Val Gly
        440                 445                 450 gcg tcc cag gcg gca aag ttc aca gta aca ccc aat gct cct tcg ata      1505
Ala Ser Gln Ala Ala Lys Phe Thr Val Thr Pro Asn Ala Pro Ser Ile
455                 460                 465                 470 acc ctc aaa ctt ggt gac tac gga gaa gtc aca ctg gac tgt gag cca      1553
Thr Leu Lys Leu Gly Asp Tyr Gly Glu Val Thr Leu Asp Cys Glu Pro
            475                 480                 485
```

```
agg agt gga ctg aac act gaa gcg ttt tac gtc atg acc gtg ggg tca      1601
Arg Ser Gly Leu Asn Thr Glu Ala Phe Tyr Val Met Thr Val Gly Ser
            490                 495                 500 aag tca ttt ctg gtc cat agg gaa tgg ttt cat gac ctc gct ctc ccc      1649
Lys Ser Phe Leu Val His Arg Glu Trp Phe His Asp Leu Ala Leu Pro
        505                 510                 515 tgg acg tcc cct tcg agc aca gcg tgg aga aac aga gaa ctc ctc atg      1697
Trp Thr Ser Pro Ser Ser Thr Ala Trp Arg Asn Arg Glu Leu Leu Met
    520                 525                 530 gag ttt gaa gag gcg cac gcc aca aaa cag tcc gtt gtt gct ctt ggg      1745
Glu Phe Glu Glu Ala His Ala Thr Lys Gln Ser Val Val Ala Leu Gly
535                 540                 545                 550 tca cag gaa gga ggc ctc cat cag gcg ttg gca gga gcc atc gtg gtg      1793
Ser Gln Glu Gly Gly Leu His Gln Ala Leu Ala Gly Ala Ile Val Val
            555                 560                 565 gag tac tca agt tca gtg aag tta aca tca ggc cac ctg aaa tgt agg      1841
Glu Tyr Ser Ser Ser Val Lys Leu Thr Ser Gly His Leu Lys Cys Arg
        570                 575                 580 ctg aaa atg gac aaa ctg gct ctg aaa ggc aca acc tat ggc atg tgc      1889
Leu Lys Met Asp Lys Leu Ala Leu Lys Gly Thr Thr Tyr Gly Met Cys
    585                 590                 595 aca gaa aaa ttc tcc ttc gcg aaa aat ccg gcg gac act ggt cac ggg      1937
Thr Glu Lys Phe Ser Phe Ala Lys Asn Pro Ala Asp Thr Gly His Gly
600                 605                 610 aca gtt gtc att gaa ctc tcc tac tct ggg agt gat ggc ccc tgc aaa      1985
Thr Val Val Ile Glu Leu Ser Tyr Ser Gly Ser Asp Gly Pro Cys Lys
            615                 620                 625         630 att ccg att gtc tcc gtt gcg agc ctc aat gac atg acc ccc gtc ggg      2033
Ile Pro Ile Val Ser Val Ala Ser Leu Asn Asp Met Thr Pro Val Gly
        635                 640                 645 cgg ctg gtg aca gtg aac ccc ttc gtc gcg act tcc agt gcc aat tca      2081
Arg Leu Val Thr Val Asn Pro Phe Val Ala Thr Ser Ser Ala Asn Ser
    650                 655                 660 aag gtg ctg gtc gag atg gaa ccc ccc ttc gga gac tcc tac atc gta      2129
Lys Val Leu Val Glu Met Glu Pro Pro Phe Gly Asp Ser Tyr Ile Val
665                 670                 675 gtt gga cgg gga gac aag cag atc aac cac cat tgg cat aaa gct gga      2177
Val Gly Arg Gly Asp Lys Gln Ile Asn His His Trp His Lys Ala Gly
            680                 685                 690 agc acg ctg ggc aaa gcc ttt tca aca act ttg aag gga gct cag aga      2225
Ser Thr Leu Gly Lys Ala Phe Ser Thr Thr Leu Lys Gly Ala Gln Arg
695                 700                 705                 710 ctg gca gcg ttg ggt gac aca gcc tgg gac ttt ggc tcc att gga ggg      2273
Leu Ala Ala Leu Gly Asp Thr Ala Trp Asp Phe Gly Ser Ile Gly Gly
            715                 720                 725 gtc ttc aac tcc ata gga aaa gcc gtt cac caa gtg ttt ggt ggt gcc      2321
Val Phe Asn Ser Ile Gly Lys Ala Val His Gln Val Phe Gly Gly Ala
        730                 735                 740 ttc aga aca ctc ttc ggg gga atg tct tgg atc aca caa ggg cta atg      2369
Phe Arg Thr Leu Phe Gly Gly Met Ser Trp Ile Thr Gln Gly Leu Met
    745                 750                 755 ggt gcc cta cta ctc tgg atg ggc gtc aac gca cga gac cga tca att      2417
Gly Ala Leu Leu Leu Trp Met Gly Val Asn Ala Arg Asp Arg Ser Ile
760                 765                 770 gct ttg gcc ttc tta gcc aca gga ggt gtc ctc gtg ttc tta gcg acc      2465
Ala Leu Ala Phe Leu Ala Thr Gly Gly Val Leu Val Phe Leu Ala Thr
775                 780                 785                 790 aat gtg cat gct gac act gga tgt gcc att gac atc aca aga aaa gag      2513
Asn Val His Ala Asp Thr Gly Cys Ala Ile Asp Ile Thr Arg Lys Glu
            795                 800                 805
```

| | |
|---|---:|
| atg agg tgt gga agt ggc atc ttc gtg cac aac gac gtg gaa gcc tgg<br>Met Arg Cys Gly Ser Gly Ile Phe Val His Asn Asp Val Glu Ala Trp<br>810                815               820 | 2561 |
| gtg gat agg tat aaa tat ttg cca gaa acg ccc aga tcc cta gca aag<br>Val Asp Arg Tyr Lys Tyr Leu Pro Glu Thr Pro Arg Ser Leu Ala Lys<br>825                830               835 | 2609 |
| atc gtc cac aaa gcg cac aag gaa ggc gtg tgc gga gtc aga tct gtc<br>Ile Val His Lys Ala His Lys Glu Gly Val Cys Gly Val Arg Ser Val<br>840                845               850 | 2657 |
| act aga ctg gag cat caa atg tgg gaa gcc gta cgg gat gaa ttg aac<br>Thr Arg Leu Glu His Gln Met Trp Glu Ala Val Arg Asp Glu Leu Asn<br>855                860               865               870 | 2705 |
| gtc ctg ctc aaa gag aat gca gtg gac ctc agt gtg gtt gtg aac aag<br>Val Leu Leu Lys Glu Asn Ala Val Asp Leu Ser Val Val Val Asn Lys<br>875                880               885 | 2753 |
| ccc gtg ggg aga tat cgc tca gcc cct aaa cgc ctg tcc atg acg caa<br>Pro Val Gly Arg Tyr Arg Ser Ala Pro Lys Arg Leu Ser Met Thr Gln<br>890                895               900 | 2801 |
| gag aag ttt gaa atg ggc tgg aaa gca tgg gga aaa agc att ctc ttt<br>Glu Lys Phe Glu Met Gly Trp Lys Ala Trp Gly Lys Ser Ile Leu Phe<br>905                910               915 | 2849 |
| gcc ccg gaa ttg gcc aac tcc aca ttt gtc gta gat gga cct gag aca<br>Ala Pro Glu Leu Ala Asn Ser Thr Phe Val Val Asp Gly Pro Glu Thr<br>920                925               930 | 2897 |
| aag gaa tgc cct gat gag cac aga gct tgg aac agc atg caa atc gaa<br>Lys Glu Cys Pro Asp Glu His Arg Ala Trp Asn Ser Met Gln Ile Glu<br>935                940               945               950 | 2945 |
| gac ttc ggc ttt ggc atc aca tca acc cgt gtg tgg ctg aag att aga<br>Asp Phe Gly Phe Gly Ile Thr Ser Thr Arg Val Trp Leu Lys Ile Arg<br>955                960               965 | 2993 |
| gag gag agc act gac gag tgt gat gga gcg atc ata ggt acg gct gtc<br>Glu Glu Ser Thr Asp Glu Cys Asp Gly Ala Ile Ile Gly Thr Ala Val<br>970                975               980 | 3041 |
| aaa gga cat gtg gca gtc cat agt gac ttg tcg tac tgg att gag agt<br>Lys Gly His Val Ala Val His Ser Asp Leu Ser Tyr Trp Ile Glu Ser<br>985                990               995 | 3089 |
| cgc tac aac gac aca tgg aaa ctt gag agg gca gtc ttt gga gaa<br>Arg Tyr Asn Asp Thr Trp Lys Leu Glu Arg Ala Val Phe Gly Glu<br>1000                1005               1010 | 3134 |
| gtt aaa tcc tgc act tgg cca gag aca cac acc cta tgg gga gat<br>Val Lys Ser Cys Thr Trp Pro Glu Thr His Thr Leu Trp Gly Asp<br>1015                1020               1025 | 3179 |
| ggt gtt gag gaa agt gaa ctc atc atc ccg cac acc ata gcc gga<br>Gly Val Glu Glu Ser Glu Leu Ile Ile Pro His Thr Ile Ala Gly<br>1030                1035               1040 | 3224 |
| cca aaa agc aag cat aat cgg agg gaa ggg tat aag aca caa aac<br>Pro Lys Ser Lys His Asn Arg Arg Glu Gly Tyr Lys Thr Gln Asn<br>1045                1050               1055 | 3269 |
| cag gga cct tgg gac gag aat ggc ata gtc ttg gac ttt gac tat<br>Gln Gly Pro Trp Asp Glu Asn Gly Ile Val Leu Asp Phe Asp Tyr<br>1060                1065               1070 | 3314 |
| tgc cca ggg aca aaa gtc acc att aca gag gat tgt ggc aag aga<br>Cys Pro Gly Thr Lys Val Thr Ile Thr Glu Asp Cys Gly Lys Arg<br>1075                1080               1085 | 3359 |
| ggc cct tcg gtc aga acc act act gac agt gga aag ttg atc act<br>Gly Pro Ser Val Arg Thr Thr Thr Asp Ser Gly Lys Leu Ile Thr<br>1090                1095               1100 | 3404 |
| gac tgg tgc tgt cgc agt tgc tcc ctt ccg ccc cta cga ttc cgg<br>Asp Trp Cys Cys Arg Ser Cys Ser Leu Pro Pro Leu Arg Phe Arg<br>1105                1110               1115 | 3449 |

| | | | | | | | | | | | | |
|---|---|---|---|---|---|---|---|---|---|---|---|---|
| aca | gaa | aat | ggc | tgc | tgg | tac | gga | atg | gaa | atc | aga | cct gtc agg | 3494 |
| Thr | Glu | Asn | Gly | Cys | Trp | Tyr | Gly | Met | Glu | Ile | Arg | Pro Val Arg | |
| 1120 | | | | | 1125 | | | | | 1130 | | | |
| cat | gat | gaa | aca | aca | ctc | gtc | aga | tcg | cag | gtt | gat | gct ttt aat | 3539 |
| His | Asp | Glu | Thr | Thr | Leu | Val | Arg | Ser | Gln | Val | Asp | Ala Phe Asn | |
| 1135 | | | | | 1140 | | | | | 1145 | | | |
| ggt | gaa | atg | gtt | gac | cct | ttt | cag | ctg | ggc | ctt | ctg | gtg atg ttt | 3584 |
| Gly | Glu | Met | Val | Asp | Pro | Phe | Gln | Leu | Gly | Leu | Leu | Val Met Phe | |
| 1150 | | | | | 1155 | | | | | 1160 | | | |
| ctg | gcc | acc | cag | gag | gtc | ctt | cgc | aag | agg | tgg | acg | gcc aga ttg | 3629 |
| Leu | Ala | Thr | Gln | Glu | Val | Leu | Arg | Lys | Arg | Trp | Thr | Ala Arg Leu | |
| 1165 | | | | | 1170 | | | | | 1175 | | | |
| acc | att | cct | gcg | gtt | ttg | ggg | gcc | cta | ctt | gtg | ctg | atg ctt ggg | 3674 |
| Thr | Ile | Pro | Ala | Val | Leu | Gly | Ala | Leu | Leu | Val | Leu | Met Leu Gly | |
| 1180 | | | | | 1185 | | | | | 1190 | | | |
| ggc | atc | act | tac | act | gat | ttg | gcg | agg | tat | gtg | gtg | cta gtc gct | 3719 |
| Gly | Ile | Thr | Tyr | Thr | Asp | Leu | Ala | Arg | Tyr | Val | Val | Leu Val Ala | |
| 1195 | | | | | 1200 | | | | | 1205 | | | |
| gcc | gct | ttc | gca | gag | gcc | aac | agt | gga | gga | gat | gtc | ctg cac ctt | 3764 |
| Ala | Ala | Phe | Ala | Glu | Ala | Asn | Ser | Gly | Gly | Asp | Val | Leu His Leu | |
| 1210 | | | | | 1215 | | | | | 1220 | | | |
| gct | ttg | att | gcc | gtt | ttc | aag | atc | caa | cca | gca | ttt | tta gtg atg | 3809 |
| Ala | Leu | Ile | Ala | Val | Phe | Lys | Ile | Gln | Pro | Ala | Phe | Leu Val Met | |
| 1225 | | | | | 1230 | | | | | 1235 | | | |
| aac | atg | ctt | agc | acg | aga | tgg | acg | aac | caa | gaa | aat | gtg gtt ctg | 3854 |
| Asn | Met | Leu | Ser | Thr | Arg | Trp | Thr | Asn | Gln | Glu | Asn | Val Val Leu | |
| 1240 | | | | | 1245 | | | | | 1250 | | | |
| gtc | cta | ggg | gct | gcc | ttt | ttc | caa | ttg | gcc | tca | gta | gat ctg caa | 3899 |
| Val | Leu | Gly | Ala | Ala | Phe | Phe | Gln | Leu | Ala | Ser | Val | Asp Leu Gln | |
| 1255 | | | | | 1260 | | | | | 1265 | | | |
| ata | gga | gtt | cac | gga | atc | ctg | aat | gcc | gcc | gct | ata | gca tgg atg | 3944 |
| Ile | Gly | Val | His | Gly | Ile | Leu | Asn | Ala | Ala | Ala | Ile | Ala Trp Met | |
| 1270 | | | | | 1275 | | | | | 1280 | | | |
| att | gtc | cgg | gcg | atc | acc | ttc | ccc | aca | acc | tcc | tcc | gtc acc atg | 3989 |
| Ile | Val | Arg | Ala | Ile | Thr | Phe | Pro | Thr | Thr | Ser | Ser | Val Thr Met | |
| 1285 | | | | | 1290 | | | | | 1295 | | | |
| cca | gtc | tta | gcg | ctt | cta | act | ccg | gga | atg | agg | gct | cta tac cta | 4034 |
| Pro | Val | Leu | Ala | Leu | Leu | Thr | Pro | Gly | Met | Arg | Ala | Leu Tyr Leu | |
| 1300 | | | | | 1305 | | | | | 1310 | | | |
| gat | act | tac | aga | atc | atc | ctc | ctc | gtc | ata | ggg | att | tgc tct ctg | 4079 |
| Asp | Thr | Tyr | Arg | Ile | Ile | Leu | Leu | Val | Ile | Gly | Ile | Cys Ser Leu | |
| 1315 | | | | | 1320 | | | | | 1325 | | | |
| ttg | caa | gag | agg | aaa | aag | acc | atg | gca | aaa | aag | aaa | gga gct gta | 4124 |
| Leu | Gln | Glu | Arg | Lys | Lys | Thr | Met | Ala | Lys | Lys | Lys | Gly Ala Val | |
| 1330 | | | | | 1335 | | | | | 1340 | | | |
| ctc | ttg | ggc | tta | gcg | ctc | aca | tcc | act | gga | tgg | ttt | tcg ccc acc | 4169 |
| Leu | Leu | Gly | Leu | Ala | Leu | Thr | Ser | Thr | Gly | Trp | Phe | Ser Pro Thr | |
| 1345 | | | | | 1350 | | | | | 1355 | | | |
| act | ata | gct | gcc | gga | cta | atg | gtc | tgc | aac | cca | aac | aag aag aga | 4214 |
| Thr | Ile | Ala | Ala | Gly | Leu | Met | Val | Cys | Asn | Pro | Asn | Lys Lys Arg | |
| 1360 | | | | | 1365 | | | | | 1370 | | | |
| ggg | tgg | cca | gct | act | gag | ttt | ttg | tcg | gca | gtt | gga | ttg atg ttt | 4259 |
| Gly | Trp | Pro | Ala | Thr | Glu | Phe | Leu | Ser | Ala | Val | Gly | Leu Met Phe | |
| 1375 | | | | | 1380 | | | | | 1385 | | | |
| gcc | atc | gta | ggt | ggt | ttg | gcg | gag | ttg | gat | att | gaa | tcc atg tca | 4304 |
| Ala | Ile | Val | Gly | Gly | Leu | Ala | Glu | Leu | Asp | Ile | Glu | Ser Met Ser | |
| 1390 | | | | | 1395 | | | | | 1400 | | | |
| ata | ccc | ttc | atg | ctg | gca | ggt | ctc | atg | gca | gtg | tcc | tac gtg gtg | 4349 |
| Ile | Pro | Phe | Met | Leu | Ala | Gly | Leu | Met | Ala | Val | Ser | Tyr Val Val | |
| 1405 | | | | | 1410 | | | | | 1415 | | | |

-continued

| | | |
|---|---|---|
| tca gga aaa gca aca gat atg tgg ctt gaa cgg gct gcc gac atc<br>Ser Gly Lys Ala Thr Asp Met Trp Leu Glu Arg Ala Ala Asp Ile<br>　　 1420　　　　　　　 1425　　　　　　　 1430 | 4394 |
| agc tgg gag atg gat gct gca atc aca gga agc agt cgg agg ctg<br>Ser Trp Glu Met Asp Ala Ala Ile Thr Gly Ser Ser Arg Arg Leu<br>1435　　　　　　　 1440　　　　　　　 1445 | 4439 |
| gat gtg aag cta gat gat gac gga gat ttt cac ttg att gac gat<br>Asp Val Lys Leu Asp Asp Asp Gly Asp Phe His Leu Ile Asp Asp<br>　　 1450　　　　　　　 1455　　　　　　　 1460 | 4484 |
| ccc ggt gtt cca tgg aag gtc tgg gtc ctg cgc atg tct tgc att<br>Pro Gly Val Pro Trp Lys Val Trp Val Leu Arg Met Ser Cys Ile<br>1465　　　　　　　 1470　　　　　　　 1475 | 4529 |
| ggg tta gcc gcc ctc acg cct tgg gcc att gtt ccc gcc gct ttt<br>Gly Leu Ala Ala Leu Thr Pro Trp Ala Ile Val Pro Ala Ala Phe<br>　　 1480　　　　　　　 1485　　　　　　　 1490 | 4574 |
| ggt tat tgg ctc act tta aaa aca aca aaa aga ggg ggc gtg ttt<br>Gly Tyr Trp Leu Thr Leu Lys Thr Thr Lys Arg Gly Gly Val Phe<br>1495　　　　　　　 1500　　　　　　　 1505 | 4619 |
| tgg gac acg cca tcc cca aaa cct tgc tca aaa gga gac acc act<br>Trp Asp Thr Pro Ser Pro Lys Pro Cys Ser Lys Gly Asp Thr Thr<br>　　 1510　　　　　　　 1515　　　　　　　 1520 | 4664 |
| aca gga gtt tac cgc att atg gct aga ggg att ctt ggc act tac<br>Thr Gly Val Tyr Arg Ile Met Ala Arg Gly Ile Leu Gly Thr Tyr<br>1525　　　　　　　 1530　　　　　　　 1535 | 4709 |
| cag gcc ggc gtc gga gtc atg tac gag aat gtt ttc cac aca cta<br>Gln Ala Gly Val Gly Val Met Tyr Glu Asn Val Phe His Thr Leu<br>　　 1540　　　　　　　 1545　　　　　　　 1550 | 4754 |
| tgg cac aca act aga gga gca gct att atg agt gga gaa gga aaa<br>Trp His Thr Thr Arg Gly Ala Ala Ile Met Ser Gly Glu Gly Lys<br>1555　　　　　　　 1560　　　　　　　 1565 | 4799 |
| ttg acg cca tac tgg ggt agt gtg aaa gaa gac cgc ata gct tac<br>Leu Thr Pro Tyr Trp Gly Ser Val Lys Glu Asp Arg Ile Ala Tyr<br>　　 1570　　　　　　　 1575　　　　　　　 1580 | 4844 |
| gga ggc cca tgg agg ttt gat cga aaa tgg aat gga act gat gac<br>Gly Gly Pro Trp Arg Phe Asp Arg Lys Trp Asn Gly Thr Asp Asp<br>1585　　　　　　　 1590　　　　　　　 1595 | 4889 |
| gtg caa gtg atc gtg gta gaa ccg ggg aag gct gca gta aac atc<br>Val Gln Val Ile Val Val Glu Pro Gly Lys Ala Ala Val Asn Ile<br>　　 1600　　　　　　　 1605　　　　　　　 1610 | 4934 |
| cag aca aaa cca gga gtg ttt cgg act ccc ttc ggg gag gtt ggg<br>Gln Thr Lys Pro Gly Val Phe Arg Thr Pro Phe Gly Glu Val Gly<br>1615　　　　　　　 1620　　　　　　　 1625 | 4979 |
| gct gtt agt ctg gat tac ccg cga gga aca tcc ggc tca ccc att<br>Ala Val Ser Leu Asp Tyr Pro Arg Gly Thr Ser Gly Ser Pro Ile<br>　　 1630　　　　　　　 1635　　　　　　　 1640 | 5024 |
| ctg gat tcc aat gga gac atc ata ggc ctg tac ggc aat gga gtt<br>Leu Asp Ser Asn Gly Asp Ile Ile Gly Leu Tyr Gly Asn Gly Val<br>1645　　　　　　　 1650　　　　　　　 1655 | 5069 |
| gag ctt ggc gat ggc tca tac gtc agc gcc atc gtg cag ggt gac<br>Glu Leu Gly Asp Gly Ser Tyr Val Ser Ala Ile Val Gln Gly Asp<br>　　 1660　　　　　　　 1665　　　　　　　 1670 | 5114 |
| cgt cag gag gaa cca gtc cca gaa gct tac acc cca aac atg ttg<br>Arg Gln Glu Glu Pro Val Pro Glu Ala Tyr Thr Pro Asn Met Leu<br>1675　　　　　　　 1680　　　　　　　 1685 | 5159 |
| aga aag aga cag atg acc gta cta gat ttg cac cct ggt tca ggg<br>Arg Lys Arg Gln Met Thr Val Leu Asp Leu His Pro Gly Ser Gly<br>　　 1690　　　　　　　 1695　　　　　　　 1700 | 5204 |
| aaa acc aag aaa att ctg cca caa ata att aag gac gct att cag<br>Lys Thr Lys Lys Ile Leu Pro Gln Ile Ile Lys Asp Ala Ile Gln<br>1705　　　　　　　 1710　　　　　　　 1715 | 5249 |

```
cag cgc cta aga aca gct gtg ttg gca ccg acg cgg gtg gta gca         5294
Gln Arg Leu Arg Thr Ala Val Leu Ala Pro Thr Arg Val Val Ala
    1720            1725            1730 gca gaa atg gca gaa gct ttg aga ggg ctc cca gta cga tat caa         5339
Ala Glu Met Ala Glu Ala Leu Arg Gly Leu Pro Val Arg Tyr Gln
1735            1740            1745 act tca gca gtg cag aga gag cac caa ggg aat gaa ata gtg gat         5384
Thr Ser Ala Val Gln Arg Glu His Gln Gly Asn Glu Ile Val Asp
    1750            1755            1760 gtg atg tgc cac gcc act ctg acc cat aga ctg atg tca ccg aac         5429
Val Met Cys His Ala Thr Leu Thr His Arg Leu Met Ser Pro Asn
1765            1770            1775 aga gtg ccc aac tac aac cta ttt gtc atg gat gaa gct cat ttc         5474
Arg Val Pro Asn Tyr Asn Leu Phe Val Met Asp Glu Ala His Phe
    1780            1785            1790 acc gac cca gcc agt ata gcc gca cga gga tac att gct acc aag         5519
Thr Asp Pro Ala Ser Ile Ala Ala Arg Gly Tyr Ile Ala Thr Lys
1795            1800            1805 gtg gaa tta ggg gag gca gca gcc atc ttt atg aca gcg acc ccg         5564
Val Glu Leu Gly Glu Ala Ala Ala Ile Phe Met Thr Ala Thr Pro
    1810            1815            1820 cct gga acc acg gat cct ttt cct gac tca aat gcc cca atc cat         5609
Pro Gly Thr Thr Asp Pro Phe Pro Asp Ser Asn Ala Pro Ile His
1825            1830            1835 gat ttg caa gat gag ata cca gac agg gcg tgg agc agt gga tac         5654
Asp Leu Gln Asp Glu Ile Pro Asp Arg Ala Trp Ser Ser Gly Tyr
    1840            1845            1850 gaa tgg atc aca gaa tat gcg gga aaa acc gtg tgg ttt gtg gca         5699
Glu Trp Ile Thr Glu Tyr Ala Gly Lys Thr Val Trp Phe Val Ala
1855            1860            1865 agc gtg aaa atg ggg aac gag att gca atg tgc ctc caa aga gcg         5744
Ser Val Lys Met Gly Asn Glu Ile Ala Met Cys Leu Gln Arg Ala
    1870            1875            1880 ggg aaa aag gtc atc caa ctc aac cgc aag tcc tat gac aca gaa         5789
Gly Lys Lys Val Ile Gln Leu Asn Arg Lys Ser Tyr Asp Thr Glu
1885            1890            1895 tac cca aaa tgt aag aat gga gac tgg gat ttt gtc atc acc act         5834
Tyr Pro Lys Cys Lys Asn Gly Asp Trp Asp Phe Val Ile Thr Thr
    1900            1905            1910 gac att tct gaa atg ggg gcc aac ttc ggt gcg agc agg gtc atc         5879
Asp Ile Ser Glu Met Gly Ala Asn Phe Gly Ala Ser Arg Val Ile
1915            1920            1925 gac tgt aga aag agc gtg aag ccc acc atc tta gaa gag gga gaa         5924
Asp Cys Arg Lys Ser Val Lys Pro Thr Ile Leu Glu Glu Gly Glu
    1930            1935            1940 ggc aga gtc atc ctc gga aac cca tcg ccc ata acc agt gca agc         5969
Gly Arg Val Ile Leu Gly Asn Pro Ser Pro Ile Thr Ser Ala Ser
1945            1950            1955 gca gct caa cgg agg ggc aga gta ggc aga aac cct aac cag gtt         6014
Ala Ala Gln Arg Arg Gly Arg Val Gly Arg Asn Pro Asn Gln Val
    1960            1965            1970 gga gat gaa tac cac tat ggg ggg gcc acc agt gaa gat gac agt         6059
Gly Asp Glu Tyr His Tyr Gly Gly Ala Thr Ser Glu Asp Asp Ser
1975            1980            1985 aac cta gcc cat tgg aca gag gca aag atc atg tta gat aac ata         6104
Asn Leu Ala His Trp Thr Glu Ala Lys Ile Met Leu Asp Asn Ile
    1990            1995            2000 cac atg ccc aat gga ctg gtg gcc cag ctc tat gga cca gag agg         6149
His Met Pro Asn Gly Leu Val Ala Gln Leu Tyr Gly Pro Glu Arg
2005            2010            2015
```

```
gaa aag gcc ttc aca atg gat ggc gaa tac cgt ctc aga ggt gaa    6194
Glu Lys Ala Phe Thr Met Asp Gly Glu Tyr Arg Leu Arg Gly Glu
    2020            2025            2030 gaa aag aaa aac ttc tta gag ctg ctt agg acg gct gac ctc ccg    6239
Glu Lys Lys Asn Phe Leu Glu Leu Leu Arg Thr Ala Asp Leu Pro
    2035            2040            2045 gtg tgg ctg gcc tac aag gtg gcg tcc aat ggc atc cag tac acc    6284
Val Trp Leu Ala Tyr Lys Val Ala Ser Asn Gly Ile Gln Tyr Thr
    2050            2055            2060 gat aga aag tgg tgt ttt gat ggg ccg cgt acg aat gcc ata ctg    6329
Asp Arg Lys Trp Cys Phe Asp Gly Pro Arg Thr Asn Ala Ile Leu
    2065            2070            2075 gag gac aac acc gag gta gag ata gtc acc cgg atg ggt gag agg    6374
Glu Asp Asn Thr Glu Val Glu Ile Val Thr Arg Met Gly Glu Arg
    2080            2085            2090 aaa atc ctc aag ccg aga tgg ctt gat gca aga gtt tat gca gat    6419
Lys Ile Leu Lys Pro Arg Trp Leu Asp Ala Arg Val Tyr Ala Asp
    2095            2100            2105 cac caa gct ctc aag tgg ttc aaa gac ttc gca gca gga aag aga    6464
His Gln Ala Leu Lys Trp Phe Lys Asp Phe Ala Ala Gly Lys Arg
    2110            2115            2120 tca gcc gtt agc ttc ata gag gtg ctc ggt cgt atg cct gag cat    6509
Ser Ala Val Ser Phe Ile Glu Val Leu Gly Arg Met Pro Glu His
    2125            2130            2135 ttc atg gga aag acg cgg gaa gct tta gac acc atg tac ttg gtt    6554
Phe Met Gly Lys Thr Arg Glu Ala Leu Asp Thr Met Tyr Leu Val
    2140            2145            2150 gca acg gct gag aaa ggt ggg aaa gca cac cga atg gct ctc gaa    6599
Ala Thr Ala Glu Lys Gly Gly Lys Ala His Arg Met Ala Leu Glu
    2155            2160            2165 gag ctg cca gat gca ctg gaa acc att aca ctt att gtt gct atc    6644
Glu Leu Pro Asp Ala Leu Glu Thr Ile Thr Leu Ile Val Ala Ile
    2170            2175            2180 act gtg atg aca gga gga ttc ttt cta ctc atg atg cag cga aag    6689
Thr Val Met Thr Gly Gly Phe Phe Leu Leu Met Met Gln Arg Lys
    2185            2190            2195 ggt ata ggg aag atg ggt ctt gga gct cta gtg ctc acg cta gct    6734
Gly Ile Gly Lys Met Gly Leu Gly Ala Leu Val Leu Thr Leu Ala
    2200            2205            2210 acc ttc ttc ctg tgg gcg gca gag gtt ccc gga aca aaa ata gca    6779
Thr Phe Phe Leu Trp Ala Ala Glu Val Pro Gly Thr Lys Ile Ala
    2215            2220            2225 ggg acc ctg ctg atc gcc ctg ctt atg gtg gtt ctc atc cca    6824
Gly Thr Leu Leu Ile Ala Leu Leu Met Val Val Leu Ile Pro
    2230            2235            2240 gaa ccg gaa aag cag agg tca caa aca gat aat caa ctg gcg gtg    6869
Glu Pro Glu Lys Gln Arg Ser Gln Thr Asp Asn Gln Leu Ala Val
    2245            2250            2255 ttt ctc atc tgt gtc ttg acc gtg gtt gga gtg gtg gca gca aac    6914
Phe Leu Ile Cys Val Leu Thr Val Val Gly Val Val Ala Ala Asn
    2260            2265            2270 gag tac ggg atg cta gaa aaa acc aaa gca gac ctc aag agc atg    6959
Glu Tyr Gly Met Leu Glu Lys Thr Lys Ala Asp Leu Lys Ser Met
    2275            2280            2285 ttt ggc gga aag acg cag gca tca gga ctg act gga tta cca agc    7004
Phe Gly Gly Lys Thr Gln Ala Ser Gly Leu Thr Gly Leu Pro Ser
    2290            2295            2300 atg gca ctg gac ctg cgt cca gcc aca gct tgg gca ctg tat ggg    7049
Met Ala Leu Asp Leu Arg Pro Ala Thr Ala Trp Ala Leu Tyr Gly
    2305            2310            2315
```

-continued

| | | | | | | | | | | | | | | |
|---|---|---|---|---|---|---|---|---|---|---|---|---|---|---|
| ggg | agc | aca | gtc | gtg | cta | acc | cct | ctt | ctg | aag | cac | ctg | atc | acg | 7094 |
| Gly | Ser | Thr | Val | Val | Leu | Thr | Pro | Leu | Leu | Lys | His | Leu | Ile | Thr | |
| | 2320 | | | | 2325 | | | | | 2330 | | | | | |
| tcg | gaa | tac | gtc | acc | aca | tcg | cta | gcc | tca | att | aac | tca | caa | gct | 7139 |
| Ser | Glu | Tyr | Val | Thr | Thr | Ser | Leu | Ala | Ser | Ile | Asn | Ser | Gln | Ala | |
| | | 2335 | | | | 2340 | | | | | 2345 | | | | |
| ggc | tca | tta | ttt | gtc | ttg | cca | cga | ggc | gtg | cct | ttt | acc | gac | cta | 7184 |
| Gly | Ser | Leu | Phe | Val | Leu | Pro | Arg | Gly | Val | Pro | Phe | Thr | Asp | Leu | |
| 2350 | | | | | 2355 | | | | | 2360 | | | | | |
| gac | ttg | acc | gtt | ggc | ctc | gtc | ttc | ctt | ggc | tgt | tgg | ggt | caa | atc | 7229 |
| Asp | Leu | Thr | Val | Gly | Leu | Val | Phe | Leu | Gly | Cys | Trp | Gly | Gln | Ile | |
| | 2365 | | | | | 2370 | | | | | 2375 | | | | |
| acc | ctc | aca | acg | ttt | ttg | aca | gcc | atg | gtt | ctg | gcg | aca | ctt | cac | 7274 |
| Thr | Leu | Thr | Thr | Phe | Leu | Thr | Ala | Met | Val | Leu | Ala | Thr | Leu | His | |
| | | 2380 | | | | | 2385 | | | | | 2390 | | | |
| tat | ggg | tac | atg | ctc | cct | gga | tgg | caa | gca | gaa | gca | ctc | agg | gca | 7319 |
| Tyr | Gly | Tyr | Met | Leu | Pro | Gly | Trp | Gln | Ala | Glu | Ala | Leu | Arg | Ala | |
| | 2395 | | | | | 2400 | | | | | 2405 | | | | |
| gcc | cag | aga | agg | aca | gcg | gct | gga | ata | atg | aag | aat | gcc | gtt | gtt | 7364 |
| Ala | Gln | Arg | Arg | Thr | Ala | Ala | Gly | Ile | Met | Lys | Asn | Ala | Val | Val | |
| 2410 | | | | | 2415 | | | | | 2420 | | | | | |
| gac | gga | atg | gtc | gcc | act | gat | gtg | cct | gaa | ctg | gaa | agg | acc | act | 7409 |
| Asp | Gly | Met | Val | Ala | Thr | Asp | Val | Pro | Glu | Leu | Glu | Arg | Thr | Thr | |
| | 2425 | | | | | 2430 | | | | | 2435 | | | | |
| cct | ctg | atg | caa | aag | aaa | gtc | gga | cag | gtg | ctc | ctc | ata | ggg | gta | 7454 |
| Pro | Leu | Met | Gln | Lys | Lys | Val | Gly | Gln | Val | Leu | Leu | Ile | Gly | Val | |
| | | 2440 | | | | | 2445 | | | | | 2450 | | | |
| agc | gtg | gca | gcg | ttc | ctc | gtc | aac | cct | aat | gtc | acc | act | gtg | aga | 7499 |
| Ser | Val | Ala | Ala | Phe | Leu | Val | Asn | Pro | Asn | Val | Thr | Thr | Val | Arg | |
| | 2455 | | | | | 2460 | | | | | 2465 | | | | |
| gaa | gca | ggg | gtg | ttg | gtg | aca | gcg | gct | acg | ctc | act | ttg | tgg | gac | 7544 |
| Glu | Ala | Gly | Val | Leu | Val | Thr | Ala | Ala | Thr | Leu | Thr | Leu | Trp | Asp | |
| 2470 | | | | | 2475 | | | | | 2480 | | | | | |
| aac | gga | gcc | agt | gcc | gtt | tgg | aat | tcc | acc | act | gcc | acg | gga | ctc | 7589 |
| Asn | Gly | Ala | Ser | Ala | Val | Trp | Asn | Ser | Thr | Thr | Ala | Thr | Gly | Leu | |
| | 2485 | | | | | 2490 | | | | | 2495 | | | | |
| tgc | cat | gta | atg | cga | ggt | agc | tac | ctg | gct | gga | ggc | tcc | att | gct | 7634 |
| Cys | His | Val | Met | Arg | Gly | Ser | Tyr | Leu | Ala | Gly | Gly | Ser | Ile | Ala | |
| | | 2500 | | | | | 2505 | | | | | 2510 | | | |
| tgg | act | ctc | atc | aag | aac | gct | gac | aag | ccc | tcc | tta | aaa | agg | gga | 7679 |
| Trp | Thr | Leu | Ile | Lys | Asn | Ala | Asp | Lys | Pro | Ser | Leu | Lys | Arg | Gly | |
| | 2515 | | | | | 2520 | | | | | 2525 | | | | |
| agg | cct | ggg | ggc | agg | acg | cta | ggg | gag | cag | tgg | aag | gaa | aaa | cta | 7724 |
| Arg | Pro | Gly | Gly | Arg | Thr | Leu | Gly | Glu | Gln | Trp | Lys | Glu | Lys | Leu | |
| 2530 | | | | | 2535 | | | | | 2540 | | | | | |
| aat | gcc | atg | agc | aga | gaa | gag | ttt | ttt | aaa | tac | cgg | aga | gag | gcc | 7769 |
| Asn | Ala | Met | Ser | Arg | Glu | Glu | Phe | Phe | Lys | Tyr | Arg | Arg | Glu | Ala | |
| | 2545 | | | | | 2550 | | | | | 2555 | | | | |
| ata | atc | gag | gtg | gac | cgc | act | gaa | gca | cgc | agg | gct | aga | cgt | gaa | 7814 |
| Ile | Ile | Glu | Val | Asp | Arg | Thr | Glu | Ala | Arg | Arg | Ala | Arg | Arg | Glu | |
| | | 2560 | | | | | 2565 | | | | | 2570 | | | |
| aat | aac | ata | gtg | gga | gga | cat | ccg | gtt | tcg | cga | ggc | tca | gca | aaa | 7859 |
| Asn | Asn | Ile | Val | Gly | Gly | His | Pro | Val | Ser | Arg | Gly | Ser | Ala | Lys | |
| 2575 | | | | | 2580 | | | | | 2585 | | | | | |
| ctc | cgt | tgg | ctc | gta | gag | aaa | gga | ttt | gtc | tcg | cca | ata | gga | aaa | 7904 |
| Leu | Arg | Trp | Leu | Val | Glu | Lys | Gly | Phe | Val | Ser | Pro | Ile | Gly | Lys | |
| | 2590 | | | | | 2595 | | | | | 2600 | | | | |
| gtc | att | gat | cta | ggg | tgt | ggg | cgt | gga | gga | tgg | agc | tac | tac | gca | 7949 |
| Val | Ile | Asp | Leu | Gly | Cys | Gly | Arg | Gly | Gly | Trp | Ser | Tyr | Tyr | Ala | |
| | 2605 | | | | | 2610 | | | | | 2615 | | | | |

```
gca acc ctg aag aag gtc cag gaa gtc aga gga tac acg aaa ggt       7994
Ala Thr Leu Lys Lys Val Gln Glu Val Arg Gly Tyr Thr Lys Gly
    2620                2625                2630 ggg gcg gga cat gaa gaa ccg atg ctc atg cag agc tac ggc tgg       8039
Gly Ala Gly His Glu Glu Pro Met Leu Met Gln Ser Tyr Gly Trp
2635                2640                2645 aac ctg gtc tcc ctg aag agt gga gtg gac gtt ttt tac aaa cct       8084
Asn Leu Val Ser Leu Lys Ser Gly Val Asp Val Phe Tyr Lys Pro
    2650                2655                2660 tca gag ccc agt gac act ctg ttc tgc gac ata ggg gaa tcc tcc       8129
Ser Glu Pro Ser Asp Thr Leu Phe Cys Asp Ile Gly Glu Ser Ser
2665                2670                2675 cca agt cca gaa gta gaa gaa caa cgc aca cta cgc gtc cta gag       8174
Pro Ser Pro Glu Val Glu Glu Gln Arg Thr Leu Arg Val Leu Glu
    2680                2685                2690 atg aca tct gac tgg ttg cac cga gga cct aga gag ttc tgt ata       8219
Met Thr Ser Asp Trp Leu His Arg Gly Pro Arg Glu Phe Cys Ile
2695                2700                2705 aaa gtt ctt tgc ccc tac atg ccc aag gtt ata gaa aaa atg gaa       8264
Lys Val Leu Cys Pro Tyr Met Pro Lys Val Ile Glu Lys Met Glu
    2710                2715                2720 gtc ctg cag cgc cgc ttc gga ggt ggg cta gtg cgt ctt ccc ctg       8309
Val Leu Gln Arg Arg Phe Gly Gly Gly Leu Val Arg Leu Pro Leu
2725                2730                2735 tcc cgc aac tcc aat cac gag atg tac tgg gtt agt gga ccg gct       8354
Ser Arg Asn Ser Asn His Glu Met Tyr Trp Val Ser Gly Pro Ala
    2740                2745                2750 ggc aat gtg gtg cac gct gtg aac atg acc agc cag gta cta ctg       8399
Gly Asn Val Val His Ala Val Asn Met Thr Ser Gln Val Leu Leu
2755                2760                2765 ggg cga atg gat cgc aca gtg tgg aga ggg cca aag tat gag gaa       8444
Gly Arg Met Asp Arg Thr Val Trp Arg Gly Pro Lys Tyr Glu Glu
    2770                2775                2780 gat gtc aac tta ggg agc gga aca aga gcc gtg gga aag gga gaa       8489
Asp Val Asn Leu Gly Ser Gly Thr Arg Ala Val Gly Lys Gly Glu
2785                2790                2795 gtc cat agc aat cag gag aaa atc aag aag aga atc cag aag ctt       8534
Val His Ser Asn Gln Glu Lys Ile Lys Lys Arg Ile Gln Lys Leu
    2800                2805                2810 aaa gaa gaa ttc gcc aca acg tgg cac aaa gac cct gag cat cca       8579
Lys Glu Glu Phe Ala Thr Thr Trp His Lys Asp Pro Glu His Pro
2815                2820                2825 tac cgc act tgg aca tac cac gga agc tat gaa gtg aag gct act       8624
Tyr Arg Thr Trp Thr Tyr His Gly Ser Tyr Glu Val Lys Ala Thr
    2830                2835                2840 ggc tca gct agt tct ctc gtc aac gga gtg gtg aag ctc atg agc       8669
Gly Ser Ala Ser Ser Leu Val Asn Gly Val Val Lys Leu Met Ser
2845                2850                2855 aaa cct tgg gac gcc att gcc aac gtc acc acc atg gcc atg act       8714
Lys Pro Trp Asp Ala Ile Ala Asn Val Thr Thr Met Ala Met Thr
    2860                2865                2870 gac acc acc cct ttt gga cag caa aga gtt ttc aag gag aaa gtt       8759
Asp Thr Thr Pro Phe Gly Gln Gln Arg Val Phe Lys Glu Lys Val
2875                2880                2885 gac acg aag gct cct gag cca cca act gga gct aag gaa gtg ctc       8804
Asp Thr Lys Ala Pro Glu Pro Pro Thr Gly Ala Lys Glu Val Leu
    2890                2895                2900 aac gag acc acc aac tgg ctg tgg gcc tac ttg tca cgg gaa aaa       8849
Asn Glu Thr Thr Asn Trp Leu Trp Ala Tyr Leu Ser Arg Glu Lys
2905                2910                2915
```

| | | | | | | | | | | | |
|---|---|---|---|---|---|---|---|---|---|---|---|
| aga | ccc | cgc | ttg | tgc | acc | aag | gaa | gaa | ttc | ata | aag | aaa | gtc | aat | 8894 |
| Arg | Pro | Arg | Leu | Cys | Thr | Lys | Glu | Glu | Phe | Ile | Lys | Lys | Val | Asn | |
| 2920 | | | | | 2925 | | | | | 2930 | | | | | |
| agc | aac | gcg | gct | ctt | gga | gca | gtg | ttc | gct | gaa | cag | aat | caa | tgg | 8939 |
| Ser | Asn | Ala | Ala | Leu | Gly | Ala | Val | Phe | Ala | Glu | Gln | Asn | Gln | Trp | |
| 2935 | | | | | 2940 | | | | | 2945 | | | | | |
| agc | acg | gcg | cgt | gag | gct | gtg | gat | gac | ccg | cgg | ttt | tgg | gag | atg | 8984 |
| Ser | Thr | Ala | Arg | Glu | Ala | Val | Asp | Asp | Pro | Arg | Phe | Trp | Glu | Met | |
| 2950 | | | | | 2955 | | | | | 2960 | | | | | |
| gtt | gat | gaa | gag | agg | gaa | aac | cat | ctg | cga | gga | gag | tgt | cac | aca | 9029 |
| Val | Asp | Glu | Glu | Arg | Glu | Asn | His | Leu | Arg | Gly | Glu | Cys | His | Thr | |
| 2965 | | | | | 2970 | | | | | 2975 | | | | | |
| tgt | atc | tat | aac | atg | atg | gga | aaa | aga | gag | aag | aag | cct | gga | gag | 9074 |
| Cys | Ile | Tyr | Asn | Met | Met | Gly | Lys | Arg | Glu | Lys | Lys | Pro | Gly | Glu | |
| 2980 | | | | | 2985 | | | | | 2990 | | | | | |
| ttt | gga | aaa | gct | aaa | gga | agc | agg | gcc | att | tgg | ttc | atg | tgg | ctt | 9119 |
| Phe | Gly | Lys | Ala | Lys | Gly | Ser | Arg | Ala | Ile | Trp | Phe | Met | Trp | Leu | |
| 2995 | | | | | 3000 | | | | | 3005 | | | | | |
| gga | gca | cgg | tat | cta | gag | ttt | gaa | gct | ttg | ggg | ttc | ctg | aat | gaa | 9164 |
| Gly | Ala | Arg | Tyr | Leu | Glu | Phe | Glu | Ala | Leu | Gly | Phe | Leu | Asn | Glu | |
| 3010 | | | | | 3015 | | | | | 3020 | | | | | |
| gat | cat | tgg | ctg | agc | cga | gag | aat | tca | gga | ggt | gga | gtg | gaa | ggc | 9209 |
| Asp | His | Trp | Leu | Ser | Arg | Glu | Asn | Ser | Gly | Gly | Gly | Val | Glu | Gly | |
| 3025 | | | | | 3030 | | | | | 3035 | | | | | |
| tca | ggc | gtc | caa | aag | ctg | gga | tac | atc | ctc | cgt | gat | ata | gca | gga | 9254 |
| Ser | Gly | Val | Gln | Lys | Leu | Gly | Tyr | Ile | Leu | Arg | Asp | Ile | Ala | Gly | |
| 3040 | | | | | 3045 | | | | | 3050 | | | | | |
| aag | caa | gga | gga | aaa | atg | tac | gct | gat | gat | acc | gcc | ggg | tgg | gac | 9299 |
| Lys | Gln | Gly | Gly | Lys | Met | Tyr | Ala | Asp | Asp | Thr | Ala | Gly | Trp | Asp | |
| 3055 | | | | | 3060 | | | | | 3065 | | | | | |
| act | aga | att | acc | aga | act | gat | tta | gaa | aat | gaa | gcc | aag | gtg | ctg | 9344 |
| Thr | Arg | Ile | Thr | Arg | Thr | Asp | Leu | Glu | Asn | Glu | Ala | Lys | Val | Leu | |
| 3070 | | | | | 3075 | | | | | 3080 | | | | | |
| gag | ctt | cta | gac | ggt | gaa | cac | cgc | atg | ctc | gcc | cga | gcc | ata | att | 9389 |
| Glu | Leu | Leu | Asp | Gly | Glu | His | Arg | Met | Leu | Ala | Arg | Ala | Ile | Ile | |
| 3085 | | | | | 3090 | | | | | 3095 | | | | | |
| gaa | ttg | act | tac | agg | cac | aaa | gtg | gtc | aag | gtc | atg | aga | cct | gca | 9434 |
| Glu | Leu | Thr | Tyr | Arg | His | Lys | Val | Val | Lys | Val | Met | Arg | Pro | Ala | |
| 3100 | | | | | 3105 | | | | | 3110 | | | | | |
| gca | gaa | gga | aag | acc | gtg | atg | gac | gtg | ata | tca | agg | gag | gat | caa | 9479 |
| Ala | Glu | Gly | Lys | Thr | Val | Met | Asp | Val | Ile | Ser | Arg | Glu | Asp | Gln | |
| 3115 | | | | | 3120 | | | | | 3125 | | | | | |
| agg | ggg | agt | gga | cag | gtg | gtc | act | tat | gct | ctt | aac | act | ttc | acg | 9524 |
| Arg | Gly | Ser | Gly | Gln | Val | Val | Thr | Tyr | Ala | Leu | Asn | Thr | Phe | Thr | |
| 3130 | | | | | 3135 | | | | | 3140 | | | | | |
| aac | atc | gct | gtc | cag | ctc | gtc | agg | ctg | atg | gag | gct | gag | ggg | gtc | 9569 |
| Asn | Ile | Ala | Val | Gln | Leu | Val | Arg | Leu | Met | Glu | Ala | Glu | Gly | Val | |
| 3145 | | | | | 3150 | | | | | 3155 | | | | | |
| att | gga | cca | caa | cac | ttg | gaa | cag | cta | cct | aga | aaa | aac | aag | ata | 9614 |
| Ile | Gly | Pro | Gln | His | Leu | Glu | Gln | Leu | Pro | Arg | Lys | Asn | Lys | Ile | |
| 3160 | | | | | 3165 | | | | | 3170 | | | | | |
| gct | gtc | agg | acc | tgg | ctc | ttt | gag | aat | gga | gag | gag | aga | gtg | tcc | 9659 |
| Ala | Val | Arg | Thr | Trp | Leu | Phe | Glu | Asn | Gly | Glu | Glu | Arg | Val | Ser | |
| 3175 | | | | | 3180 | | | | | 3185 | | | | | |
| agg | atg | gct | atc | agc | gga | gac | gac | tgt | gtc | gtc | aag | ccg | ctg | gac | 9704 |
| Arg | Met | Ala | Ile | Ser | Gly | Asp | Asp | Cys | Val | Val | Lys | Pro | Leu | Asp | |
| 3190 | | | | | 3195 | | | | | 3200 | | | | | |
| gac | aga | ttc | gcc | acg | gcc | ctc | cac | ttc | ctc | aac | gca | atg | tca | aag | 9749 |
| Asp | Arg | Phe | Ala | Thr | Ala | Leu | His | Phe | Leu | Asn | Ala | Met | Ser | Lys | |
| 3205 | | | | | 3210 | | | | | 3215 | | | | | |

```
gtc aga aaa gac atc cag gaa tgg aag cct tca cat ggc tgg cac      9794
Val Arg Lys Asp Ile Gln Glu Trp Lys Pro Ser His Gly Trp His
    3220            3225                3230 gat tgg cag caa gtt ccc ttc tgc tct aac cat ttt cag gag att      9839
Asp Trp Gln Gln Val Pro Phe Cys Ser Asn His Phe Gln Glu Ile
3235                3240                3245 gtg atg aaa gat gga agg agt ata gtt gtc ccg tgc aga gga cag      9884
Val Met Lys Asp Gly Arg Ser Ile Val Val Pro Cys Arg Gly Gln
    3250            3255                3260 gat gag ctg ata ggc agg gct cgc atc tcc cca gga gct gga tgg      9929
Asp Glu Leu Ile Gly Arg Ala Arg Ile Ser Pro Gly Ala Gly Trp
3265                3270                3275 aat gtg aag gac aca gct tgt ctg gcc aaa gca tat gca cag atg      9974
Asn Val Lys Asp Thr Ala Cys Leu Ala Lys Ala Tyr Ala Gln Met
    3280            3285                3290 tgg cta ctc cta tac ttc cat cgt agg gac ttg cgt ctc atg gca     10019
Trp Leu Leu Leu Tyr Phe His Arg Arg Asp Leu Arg Leu Met Ala
3295                3300                3305 aat gcg att tgc tca gca gtg cca gtg gat tgg gtg ccc acg ggc     10064
Asn Ala Ile Cys Ser Ala Val Pro Val Asp Trp Val Pro Thr Gly
    3310            3315                3320 agg aca tcc tgg tcg ata cac tcg aaa gga gag tgg atg acc aca     10109
Arg Thr Ser Trp Ser Ile His Ser Lys Gly Glu Trp Met Thr Thr
3325                3330                3335 gaa gac atg ctg cag gtc tgg aac aga gtc tgg att gaa gaa aat     10154
Glu Asp Met Leu Gln Val Trp Asn Arg Val Trp Ile Glu Glu Asn
    3340            3345                3350 gaa tgg atg gtg gac aag act cca ata aca agc tgg aca gac gtt     10199
Glu Trp Met Val Asp Lys Thr Pro Ile Thr Ser Trp Thr Asp Val
3355                3360                3365 ccg tat gtg gga aag cgg gag gac atc tgg tgt ggc agc ctc atc     10244
Pro Tyr Val Gly Lys Arg Glu Asp Ile Trp Cys Gly Ser Leu Ile
    3370            3375                3380 gga acg cga tcc aga gca acc tgg gct gag aac atc tac gcg gcg     10289
Gly Thr Arg Ser Arg Ala Thr Trp Ala Glu Asn Ile Tyr Ala Ala
3385                3390                3395 ata aac cag gtt aga gct gtc att ggg aaa gaa aat tat gtt gac     10334
Ile Asn Gln Val Arg Ala Val Ile Gly Lys Glu Asn Tyr Val Asp
    3400            3405                3410 tac atg acc tca ctc agg aga tac gaa gat gtc ttg atc cag gaa     10379
Tyr Met Thr Ser Leu Arg Arg Tyr Glu Asp Val Leu Ile Gln Glu
3415                3420                3425 gac agg gtc atc tagtgtgatt taaggtggaa aagcagatta tgtaataat      10431
Asp Arg Val Ile
    3430 gtaaatgaga aaatgcatgc atatggagtc aggccagcaa aagctgccac cggatactgg   10491 gtagacggtg ctgtctgcgt cccagtccca ggaggactgg gttaacaaat ctgacaacag   10551 aaagtgagaa agccctcaga accgtctcgg aagcaggtcc ctgctcactg gaagttgaag   10611 gaccaacgtc aggccacaaa tttgtgccac tccgctgagg agtgcggcct gcgcagcccc   10671 aggaggactg ggttaccaaa gccgttgagc ccccacggcc caagcctcgt ctaggatgca   10731 atagacgagg tgtaaggact agaggttaga ggagacccccg tggaaacaac aacatgcggc   10791 ccaagccccc tcgaagctgt agaggaggtg aaggactag aggttagagg agacccccgca   10851 tttgcatcaa acagcatatt gacacctggg aatagactgg gagatcttct gctctatctc   10911 aacatcagct actaggcaca gagcgccgaa gtatgtagct ggtggtgagg aagaacacag   10971 gatct                                                             10976
```

<210> SEQ ID NO 4
<211> LENGTH: 3432
<212> TYPE: PRT
<213> ORGANISM: Japanese encephalitis virus

<400> SEQUENCE: 4

```
Met Thr Lys Lys Pro Gly Gly Pro Gly Lys Asn Arg Ala Ile Asn Met
1               5                   10                  15

Leu Lys Arg Gly Leu Pro Arg Val Phe Pro Leu Val Gly Val Lys Arg
            20                  25                  30

Val Val Met Ser Leu Leu Asp Gly Arg Gly Pro Val Arg Phe Val Leu
        35                  40                  45

Ala Leu Ile Thr Phe Phe Lys Phe Thr Ala Leu Ala Pro Thr Lys Ala
    50                  55                  60

Leu Leu Gly Arg Trp Lys Ala Val Glu Lys Ser Val Ala Met Lys His
65                  70                  75                  80

Leu Thr Ser Phe Lys Arg Glu Leu Gly Thr Leu Ile Asp Ala Val Asn
                85                  90                  95

Lys Arg Gly Arg Lys Gln Asn Lys Arg Gly Gly Asn Glu Gly Ser Ile
            100                 105                 110

Met Trp Leu Ala Ser Leu Ala Val Val Ile Ala Cys Ala Gly Ala Met
        115                 120                 125

Lys Leu Ser Asn Phe Gln Gly Lys Leu Leu Met Thr Ile Asn Asn Thr
    130                 135                 140

Asp Ile Ala Asp Val Ile Val Ile Pro Thr Ser Lys Gly Glu Asn Arg
145                 150                 155                 160

Cys Trp Val Arg Ala Ile Asp Val Gly Tyr Met Cys Glu Asp Thr Ile
                165                 170                 175

Thr Tyr Glu Cys Pro Lys Leu Ala Met Gly Asn Asp Pro Glu Asp Val
            180                 185                 190

Asp Cys Trp Cys Asp Asn Gln Glu Val Tyr Val Gln Tyr Gly Arg Cys
        195                 200                 205

Thr Arg Thr Arg His Ser Lys Arg Ser Arg Arg Ser Val Ser Val Gln
    210                 215                 220

Thr His Gly Glu Ser Ser Leu Val Asn Lys Lys Glu Ala Trp Leu Asp
225                 230                 235                 240

Ser Thr Lys Ala Thr Arg Tyr Leu Met Lys Thr Glu Asn Trp Ile Ile
                245                 250                 255

Arg Asn Pro Gly Tyr Ala Phe Leu Ala Ala Val Leu Gly Trp Met Leu
            260                 265                 270

Gly Ser Asn Asn Gly Gln Arg Val Val Phe Thr Ile Leu Leu Leu Leu
        275                 280                 285

Val Ala Pro Ala Tyr Ser Phe Asn Cys Leu Gly Met Gly Asn Arg Asp
    290                 295                 300

Phe Ile Glu Gly Ala Ser Gly Ala Thr Trp Val Asp Leu Val Leu Glu
305                 310                 315                 320

Gly Asp Ser Cys Leu Thr Ile Met Ala Asn Asp Lys Pro Thr Leu Asp
                325                 330                 335

Val Arg Met Ile Asn Ile Glu Ala Ser Gln Leu Ala Glu Val Arg Ser
            340                 345                 350

Tyr Cys Tyr His Ala Ser Val Thr Asp Ile Ser Thr Val Ala Arg Cys
        355                 360                 365

Pro Thr Thr Gly Glu Ala His Asn Glu Lys Arg Ala Asp Ser Ser Tyr
    370                 375                 380
```

```
Val Cys Lys Gln Gly Phe Thr Asp Arg Gly Trp Gly Asn Gly Cys Gly
385                 390                 395                 400

Leu Phe Gly Lys Gly Ser Ile Asp Thr Cys Ala Lys Phe Ser Cys Thr
            405                 410                 415

Ser Lys Ala Ile Gly Arg Thr Ile Gln Pro Glu Asn Ile Lys Tyr Lys
            420                 425                 430

Val Gly Ile Phe Val His Gly Ala Thr Thr Ser Glu Asn His Gly Asn
            435                 440                 445

Tyr Ser Ala Gln Val Gly Ala Ser Gln Ala Ala Lys Phe Thr Val Thr
            450                 455                 460

Pro Asn Ala Pro Ser Ile Thr Leu Lys Leu Gly Asp Tyr Gly Glu Val
465                 470                 475                 480

Thr Leu Asp Cys Glu Pro Arg Ser Gly Leu Asn Thr Glu Ala Phe Tyr
            485                 490                 495

Val Met Thr Val Gly Ser Lys Ser Phe Leu Val His Arg Glu Trp Phe
            500                 505                 510

His Asp Leu Ala Leu Pro Trp Thr Ser Pro Ser Ser Thr Ala Trp Arg
            515                 520                 525

Asn Arg Glu Leu Leu Met Glu Phe Glu Glu Ala His Ala Thr Lys Gln
            530                 535                 540

Ser Val Val Ala Leu Gly Ser Gln Glu Gly Gly Leu His Gln Ala Leu
545                 550                 555                 560

Ala Gly Ala Ile Val Val Glu Tyr Ser Ser Val Lys Leu Thr Ser
            565                 570                 575

Gly His Leu Lys Cys Arg Leu Lys Met Asp Lys Leu Ala Leu Lys Gly
            580                 585                 590

Thr Thr Tyr Gly Met Cys Thr Glu Lys Phe Ser Phe Ala Lys Asn Pro
            595                 600                 605

Ala Asp Thr Gly His Gly Thr Val Val Ile Glu Leu Ser Tyr Ser Gly
            610                 615                 620

Ser Asp Gly Pro Cys Lys Ile Pro Ile Val Ser Val Ala Ser Leu Asn
625                 630                 635                 640

Asp Met Thr Pro Val Gly Arg Leu Val Thr Val Asn Pro Phe Val Ala
            645                 650                 655

Thr Ser Ser Ala Asn Ser Lys Val Leu Val Glu Met Glu Pro Pro Phe
            660                 665                 670

Gly Asp Ser Tyr Ile Val Val Gly Arg Gly Asp Lys Gln Ile Asn His
            675                 680                 685

His Trp His Lys Ala Gly Ser Thr Leu Gly Lys Ala Phe Ser Thr Thr
            690                 695                 700

Leu Lys Gly Ala Gln Arg Leu Ala Ala Leu Gly Asp Thr Ala Trp Asp
705                 710                 715                 720

Phe Gly Ser Ile Gly Gly Val Phe Asn Ser Ile Gly Lys Ala Val His
            725                 730                 735

Gln Val Phe Gly Gly Ala Phe Arg Thr Leu Phe Gly Gly Met Ser Trp
            740                 745                 750

Ile Thr Gln Gly Leu Met Gly Ala Leu Leu Leu Trp Met Gly Val Asn
            755                 760                 765

Ala Arg Asp Arg Ser Ile Ala Leu Ala Phe Leu Ala Thr Gly Gly Val
            770                 775                 780

Leu Val Phe Leu Ala Thr Asn Val His Ala Asp Thr Gly Cys Ala Ile
785                 790                 795                 800

Asp Ile Thr Arg Lys Glu Met Arg Cys Gly Ser Gly Ile Phe Val His
```

-continued

```
                805                 810                 815
Asn Asp Val Glu Ala Trp Val Asp Arg Tyr Lys Tyr Leu Pro Glu Thr
            820                 825                 830

Pro Arg Ser Leu Ala Lys Ile Val His Lys Ala His Lys Glu Gly Val
            835                 840                 845

Cys Gly Val Arg Ser Val Thr Arg Leu Glu His Gln Met Trp Glu Ala
850                 855                 860

Val Arg Asp Glu Leu Asn Val Leu Leu Lys Glu Asn Ala Val Asp Leu
865                 870                 875                 880

Ser Val Val Asn Lys Pro Val Gly Arg Tyr Arg Ser Ala Pro Lys
                885                 890                 895

Arg Leu Ser Met Thr Gln Glu Lys Phe Glu Met Gly Trp Lys Ala Trp
            900                 905                 910

Gly Lys Ser Ile Leu Phe Ala Pro Glu Leu Ala Asn Ser Thr Phe Val
            915                 920                 925

Val Asp Gly Pro Glu Thr Lys Glu Cys Pro Asp Glu His Arg Ala Trp
930                 935                 940

Asn Ser Met Gln Ile Glu Asp Phe Gly Phe Gly Ile Thr Ser Thr Arg
945                 950                 955                 960

Val Trp Leu Lys Ile Arg Glu Glu Ser Thr Asp Glu Cys Asp Gly Ala
            965                 970                 975

Ile Ile Gly Thr Ala Val Lys Gly His Val Ala Val His Ser Asp Leu
            980                 985                 990

Ser Tyr Trp Ile Glu Ser Arg Tyr Asn Asp Thr Trp Lys Leu Glu Arg
                995                1000                1005

Ala Val Phe Gly Glu Val Lys Ser Cys Thr Trp Pro Glu Thr His
   1010                1015                1020

Thr Leu Trp Gly Asp Gly Val Glu Glu Ser Glu Leu Ile Ile Pro
   1025                1030                1035

His Thr Ile Ala Gly Pro Lys Ser Lys His Asn Arg Arg Glu Gly
   1040                1045                1050

Tyr Lys Thr Gln Asn Gln Gly Pro Trp Asp Glu Asn Gly Ile Val
   1055                1060                1065

Leu Asp Phe Asp Tyr Cys Pro Gly Thr Lys Val Thr Ile Thr Glu
   1070                1075                1080

Asp Cys Gly Lys Arg Gly Pro Ser Val Arg Thr Thr Thr Asp Ser
   1085                1090                1095

Gly Lys Leu Ile Thr Asp Trp Cys Cys Arg Ser Cys Ser Leu Pro
   1100                1105                1110

Pro Leu Arg Phe Arg Thr Glu Asn Gly Cys Trp Tyr Gly Met Glu
   1115                1120                1125

Ile Arg Pro Val Arg His Asp Glu Thr Thr Leu Val Arg Ser Gln
   1130                1135                1140

Val Asp Ala Phe Asn Gly Glu Met Val Asp Pro Phe Gln Leu Gly
   1145                1150                1155

Leu Leu Val Met Phe Leu Ala Thr Gln Glu Val Leu Arg Lys Arg
   1160                1165                1170

Trp Thr Ala Arg Leu Thr Ile Pro Ala Val Leu Gly Ala Leu Leu
   1175                1180                1185

Val Leu Met Leu Gly Gly Ile Thr Tyr Thr Asp Leu Ala Arg Tyr
   1190                1195                1200

Val Val Leu Val Ala Ala Ala Phe Ala Glu Ala Asn Ser Gly Gly
   1205                1210                1215
```

```
Asp Val Leu His Leu Ala Leu Ile Ala Val Phe Lys Ile Gln Pro
    1220             1225                 1230

Ala Phe Leu Val Met Asn Met Leu Ser Thr Arg Trp Thr Asn Gln
    1235             1240                 1245

Glu Asn Val Val Leu Val Leu Gly Ala Ala Phe Gln Leu Ala
    1250             1255                 1260

Ser Val Asp Leu Gln Ile Gly Val His Gly Ile Leu Asn Ala Ala
    1265             1270                 1275

Ala Ile Ala Trp Met Ile Val Arg Ala Ile Thr Phe Pro Thr Thr
    1280             1285                 1290

Ser Ser Val Thr Met Pro Val Leu Ala Leu Leu Thr Pro Gly Met
    1295             1300                 1305

Arg Ala Leu Tyr Leu Asp Thr Tyr Arg Ile Ile Leu Leu Val Ile
    1310             1315                 1320

Gly Ile Cys Ser Leu Leu Gln Glu Arg Lys Lys Thr Met Ala Lys
    1325             1330                 1335

Lys Lys Gly Ala Val Leu Leu Gly Leu Ala Leu Thr Ser Thr Gly
    1340             1345                 1350

Trp Phe Ser Pro Thr Thr Ile Ala Ala Gly Leu Met Val Cys Asn
    1355             1360                 1365

Pro Asn Lys Lys Arg Gly Trp Pro Ala Thr Glu Phe Leu Ser Ala
    1370             1375                 1380

Val Gly Leu Met Phe Ala Ile Val Gly Gly Leu Ala Glu Leu Asp
    1385             1390                 1395

Ile Glu Ser Met Ser Ile Pro Phe Met Leu Ala Gly Leu Met Ala
    1400             1405                 1410

Val Ser Tyr Val Val Ser Gly Lys Ala Thr Asp Met Trp Leu Glu
    1415             1420                 1425

Arg Ala Ala Asp Ile Ser Trp Glu Met Asp Ala Ala Ile Thr Gly
    1430             1435                 1440

Ser Ser Arg Arg Leu Asp Val Lys Leu Asp Asp Gly Asp Phe
    1445             1450                 1455

His Leu Ile Asp Asp Pro Gly Val Pro Trp Lys Val Trp Val Leu
    1460             1465                 1470

Arg Met Ser Cys Ile Gly Leu Ala Ala Leu Thr Pro Trp Ala Ile
    1475             1480                 1485

Val Pro Ala Ala Phe Gly Tyr Trp Leu Thr Leu Lys Thr Thr Lys
    1490             1495                 1500

Arg Gly Gly Val Phe Trp Asp Thr Pro Ser Pro Lys Pro Cys Ser
    1505             1510                 1515

Lys Gly Asp Thr Thr Thr Gly Val Tyr Arg Ile Met Ala Arg Gly
    1520             1525                 1530

Ile Leu Gly Thr Tyr Gln Ala Gly Val Gly Val Met Tyr Glu Asn
    1535             1540                 1545

Val Phe His Thr Leu Trp His Thr Thr Arg Gly Ala Ala Ile Met
    1550             1555                 1560

Ser Gly Glu Gly Lys Leu Thr Pro Tyr Trp Gly Ser Val Lys Glu
    1565             1570                 1575

Asp Arg Ile Ala Tyr Gly Gly Pro Trp Arg Phe Asp Arg Lys Trp
    1580             1585                 1590

Asn Gly Thr Asp Asp Val Gln Val Ile Val Val Glu Pro Gly Lys
    1595             1600                 1605

Ala Ala Val Asn Ile Gln Thr Lys Pro Gly Val Phe Arg Thr Pro
    1610             1615                 1620
```

```
Phe Gly Glu Val Gly Ala Val Ser Leu Asp Tyr Pro Arg Gly Thr
    1625            1630                1635
Ser Gly Ser Pro Ile Leu Asp Ser Asn Gly Asp Ile Ile Gly Leu
    1640            1645                1650
Tyr Gly Asn Gly Val Glu Leu Gly Asp Gly Ser Tyr Val Ser Ala
    1655            1660                1665
Ile Val Gln Gly Asp Arg Gln Glu Pro Val Pro Glu Ala Tyr
    1670            1675                1680
Thr Pro Asn Met Leu Arg Lys Arg Gln Met Thr Val Leu Asp Leu
    1685            1690                1695
His Pro Gly Ser Gly Lys Thr Lys Lys Ile Leu Pro Gln Ile Ile
    1700            1705                1710
Lys Asp Ala Ile Gln Gln Arg Leu Arg Thr Ala Val Leu Ala Pro
    1715            1720                1725
Thr Arg Val Val Ala Ala Glu Met Ala Glu Ala Leu Arg Gly Leu
    1730            1735                1740
Pro Val Arg Tyr Gln Thr Ser Ala Val Gln Arg Glu His Gln Gly
    1745            1750                1755
Asn Glu Ile Val Asp Val Met Cys His Ala Thr Leu Thr His Arg
    1760            1765                1770
Leu Met Ser Pro Asn Arg Val Pro Asn Tyr Asn Leu Phe Val Met
    1775            1780                1785
Asp Glu Ala His Phe Thr Asp Pro Ala Ser Ile Ala Ala Arg Gly
    1790            1795                1800
Tyr Ile Ala Thr Lys Val Glu Leu Gly Glu Ala Ala Ala Ile Phe
    1805            1810                1815
Met Thr Ala Thr Pro Pro Gly Thr Thr Asp Pro Phe Pro Asp Ser
    1820            1825                1830
Asn Ala Pro Ile His Asp Leu Gln Asp Glu Ile Pro Asp Arg Ala
    1835            1840                1845
Trp Ser Ser Gly Tyr Glu Trp Ile Thr Glu Tyr Ala Gly Lys Thr
    1850            1855                1860
Val Trp Phe Val Ala Ser Val Lys Met Gly Asn Glu Ile Ala Met
    1865            1870                1875
Cys Leu Gln Arg Ala Gly Lys Lys Val Ile Gln Leu Asn Arg Lys
    1880            1885                1890
Ser Tyr Asp Thr Glu Tyr Pro Lys Cys Lys Asn Gly Asp Trp Asp
    1895            1900                1905
Phe Val Ile Thr Thr Asp Ile Ser Glu Met Gly Ala Asn Phe Gly
    1910            1915                1920
Ala Ser Arg Val Ile Asp Cys Arg Lys Ser Val Lys Pro Thr Ile
    1925            1930                1935
Leu Glu Glu Gly Glu Gly Arg Val Ile Leu Gly Asn Pro Ser Pro
    1940            1945                1950
Ile Thr Ser Ala Ser Ala Ala Gln Arg Arg Gly Arg Val Gly Arg
    1955            1960                1965
Asn Pro Asn Gln Val Gly Asp Glu Tyr His Tyr Gly Gly Ala Thr
    1970            1975                1980
Ser Glu Asp Asp Ser Asn Leu Ala His Trp Thr Glu Ala Lys Ile
    1985            1990                1995
Met Leu Asp Asn Ile His Met Pro Asn Gly Leu Val Ala Gln Leu
    2000            2005                2010
Tyr Gly Pro Glu Arg Glu Lys Ala Phe Thr Met Asp Gly Glu Tyr
```

```
                2015                    2020                    2025

Arg Leu Arg Gly Glu Glu Lys Lys Asn Phe Leu Glu Leu Leu Arg
    2030                    2035                    2040

Thr Ala Asp Leu Pro Val Trp Leu Ala Tyr Lys Val Ala Ser Asn
    2045                    2050                    2055

Gly Ile Gln Tyr Thr Asp Arg Lys Trp Cys Phe Asp Gly Pro Arg
    2060                    2065                    2070

Thr Asn Ala Ile Leu Glu Asp Asn Thr Glu Val Glu Ile Val Thr
    2075                    2080                    2085

Arg Met Gly Glu Arg Lys Ile Leu Lys Pro Arg Trp Leu Asp Ala
    2090                    2095                    2100

Arg Val Tyr Ala Asp His Gln Ala Leu Lys Trp Phe Lys Asp Phe
    2105                    2110                    2115

Ala Ala Gly Lys Arg Ser Ala Val Ser Phe Ile Glu Val Leu Gly
    2120                    2125                    2130

Arg Met Pro Glu His Phe Met Gly Lys Thr Arg Glu Ala Leu Asp
    2135                    2140                    2145

Thr Met Tyr Leu Val Ala Thr Ala Glu Lys Gly Gly Lys Ala His
    2150                    2155                    2160

Arg Met Ala Leu Glu Glu Leu Pro Asp Ala Leu Glu Thr Ile Thr
    2165                    2170                    2175

Leu Ile Val Ala Ile Thr Val Met Thr Gly Gly Phe Phe Leu Leu
    2180                    2185                    2190

Met Met Gln Arg Lys Gly Ile Gly Lys Met Gly Leu Gly Ala Leu
    2195                    2200                    2205

Val Leu Thr Leu Ala Thr Phe Phe Leu Trp Ala Ala Glu Val Pro
    2210                    2215                    2220

Gly Thr Lys Ile Ala Gly Thr Leu Leu Ile Ala Leu Leu Leu Met
    2225                    2230                    2235

Val Val Leu Ile Pro Glu Pro Glu Lys Gln Arg Ser Gln Thr Asp
    2240                    2245                    2250

Asn Gln Leu Ala Val Phe Leu Ile Cys Val Leu Thr Val Val Gly
    2255                    2260                    2265

Val Val Ala Ala Asn Glu Tyr Gly Met Leu Glu Lys Thr Lys Ala
    2270                    2275                    2280

Asp Leu Lys Ser Met Phe Gly Gly Lys Thr Gln Ala Ser Gly Leu
    2285                    2290                    2295

Thr Gly Leu Pro Ser Met Ala Leu Asp Leu Arg Pro Ala Thr Ala
    2300                    2305                    2310

Trp Ala Leu Tyr Gly Gly Ser Thr Val Val Leu Thr Pro Leu Leu
    2315                    2320                    2325

Lys His Leu Ile Thr Ser Glu Tyr Val Thr Thr Ser Leu Ala Ser
    2330                    2335                    2340

Ile Asn Ser Gln Ala Gly Ser Leu Phe Val Leu Pro Arg Gly Val
    2345                    2350                    2355

Pro Phe Thr Asp Leu Asp Leu Thr Val Gly Leu Val Phe Leu Gly
    2360                    2365                    2370

Cys Trp Gly Gln Ile Thr Leu Thr Thr Phe Leu Thr Ala Met Val
    2375                    2380                    2385

Leu Ala Thr Leu His Tyr Gly Tyr Met Leu Pro Gly Trp Gln Ala
    2390                    2395                    2400

Glu Ala Leu Arg Ala Ala Gln Arg Arg Thr Ala Ala Gly Ile Met
    2405                    2410                    2415
```

-continued

Lys Asn Ala Val Val Asp Gly Met Val Ala Thr Asp Val Pro Glu
2420                2425                2430

Leu Glu Arg Thr Thr Pro Leu Met Gln Lys Lys Val Gly Gln Val
2435                2440                2445

Leu Leu Ile Gly Val Ser Val Ala Ala Phe Leu Val Asn Pro Asn
2450                2455                2460

Val Thr Thr Val Arg Glu Ala Gly Val Leu Val Thr Ala Ala Thr
2465                2470                2475

Leu Thr Leu Trp Asp Asn Gly Ala Ser Ala Val Trp Asn Ser Thr
2480                2485                2490

Thr Ala Thr Gly Leu Cys His Val Met Arg Gly Ser Tyr Leu Ala
2495                2500                2505

Gly Gly Ser Ile Ala Trp Thr Leu Ile Lys Asn Ala Asp Lys Pro
2510                2515                2520

Ser Leu Lys Arg Gly Arg Pro Gly Gly Arg Thr Leu Gly Glu Gln
2525                2530                2535

Trp Lys Glu Lys Leu Asn Ala Met Ser Arg Glu Glu Phe Phe Lys
2540                2545                2550

Tyr Arg Arg Glu Ala Ile Ile Glu Val Asp Arg Thr Glu Ala Arg
2555                2560                2565

Arg Ala Arg Arg Glu Asn Asn Ile Val Gly Gly His Pro Val Ser
2570                2575                2580

Arg Gly Ser Ala Lys Leu Arg Trp Leu Val Glu Lys Gly Phe Val
2585                2590                2595

Ser Pro Ile Gly Lys Val Ile Asp Leu Gly Cys Gly Arg Gly Gly
2600                2605                2610

Trp Ser Tyr Tyr Ala Ala Thr Leu Lys Lys Val Gln Glu Val Arg
2615                2620                2625

Gly Tyr Thr Lys Gly Gly Ala Gly His Glu Glu Pro Met Leu Met
2630                2635                2640

Gln Ser Tyr Gly Trp Asn Leu Val Ser Leu Lys Ser Gly Val Asp
2645                2650                2655

Val Phe Tyr Lys Pro Ser Glu Pro Ser Asp Thr Leu Phe Cys Asp
2660                2665                2670

Ile Gly Glu Ser Ser Pro Ser Pro Glu Val Glu Glu Gln Arg Thr
2675                2680                2685

Leu Arg Val Leu Glu Met Thr Ser Asp Trp Leu His Arg Gly Pro
2690                2695                2700

Arg Glu Phe Cys Ile Lys Val Leu Cys Pro Tyr Met Pro Lys Val
2705                2710                2715

Ile Glu Lys Met Glu Val Leu Gln Arg Arg Phe Gly Gly Gly Leu
2720                2725                2730

Val Arg Leu Pro Leu Ser Arg Asn Ser Asn His Glu Met Tyr Trp
2735                2740                2745

Val Ser Gly Pro Ala Gly Asn Val Val His Ala Val Asn Met Thr
2750                2755                2760

Ser Gln Val Leu Leu Gly Arg Met Asp Arg Thr Val Trp Arg Gly
2765                2770                2775

Pro Lys Tyr Glu Glu Asp Val Asn Leu Gly Ser Gly Thr Arg Ala
2780                2785                2790

Val Gly Lys Gly Glu Val His Ser Asn Gln Glu Lys Ile Lys Lys
2795                2800                2805

Arg Ile Gln Lys Leu Lys Glu Glu Phe Ala Thr Thr Trp His Lys
2810                2815                2820

```
Asp Pro Glu His Pro Tyr Arg Thr Trp Thr Tyr His Gly Ser Tyr
    2825            2830                2835

Glu Val Lys Ala Thr Gly Ser Ala Ser Ser Leu Val Asn Gly Val
    2840            2845                2850

Val Lys Leu Met Ser Lys Pro Trp Asp Ala Ile Ala Asn Val Thr
    2855            2860                2865

Thr Met Ala Met Thr Asp Thr Pro Phe Gly Gln Gln Arg Val
    2870            2875                2880

Phe Lys Glu Lys Val Asp Thr Lys Ala Pro Glu Pro Pro Thr Gly
    2885            2890                2895

Ala Lys Glu Val Leu Asn Glu Thr Thr Asn Trp Leu Trp Ala Tyr
    2900            2905                2910

Leu Ser Arg Glu Lys Arg Pro Arg Leu Cys Thr Lys Glu Glu Phe
    2915            2920                2925

Ile Lys Lys Val Asn Ser Asn Ala Ala Leu Gly Ala Val Phe Ala
    2930            2935                2940

Glu Gln Asn Gln Trp Ser Thr Ala Arg Glu Ala Val Asp Asp Pro
    2945            2950                2955

Arg Phe Trp Glu Met Val Asp Glu Glu Arg Glu Asn His Leu Arg
    2960            2965                2970

Gly Glu Cys His Thr Cys Ile Tyr Asn Met Met Gly Lys Arg Glu
    2975            2980                2985

Lys Lys Pro Gly Glu Phe Gly Lys Ala Lys Gly Ser Arg Ala Ile
    2990            2995                3000

Trp Phe Met Trp Leu Gly Ala Arg Tyr Leu Glu Phe Glu Ala Leu
    3005            3010                3015

Gly Phe Leu Asn Glu Asp His Trp Leu Ser Arg Glu Asn Ser Gly
    3020            3025                3030

Gly Gly Val Glu Gly Ser Gly Val Gln Lys Leu Gly Tyr Ile Leu
    3035            3040                3045

Arg Asp Ile Ala Gly Lys Gln Gly Gly Lys Met Tyr Ala Asp Asp
    3050            3055                3060

Thr Ala Gly Trp Asp Thr Arg Ile Thr Arg Thr Asp Leu Glu Asn
    3065            3070                3075

Glu Ala Lys Val Leu Glu Leu Leu Asp Gly Glu His Arg Met Leu
    3080            3085                3090

Ala Arg Ala Ile Ile Glu Leu Thr Tyr Arg His Lys Val Val Lys
    3095            3100                3105

Val Met Arg Pro Ala Ala Glu Gly Lys Thr Val Met Asp Val Ile
    3110            3115                3120

Ser Arg Glu Asp Gln Arg Gly Ser Gly Gln Val Val Thr Tyr Ala
    3125            3130                3135

Leu Asn Thr Phe Thr Asn Ile Ala Val Gln Leu Val Arg Leu Met
    3140            3145                3150

Glu Ala Glu Gly Val Ile Gly Pro Gln His Leu Glu Gln Leu Pro
    3155            3160                3165

Arg Lys Asn Lys Ile Ala Val Arg Thr Trp Leu Phe Glu Asn Gly
    3170            3175                3180

Glu Glu Arg Val Ser Arg Met Ala Ile Ser Gly Asp Asp Cys Val
    3185            3190                3195

Val Lys Pro Leu Asp Asp Arg Phe Ala Thr Ala Leu His Phe Leu
    3200            3205                3210

Asn Ala Met Ser Lys Val Arg Lys Asp Ile Gln Glu Trp Lys Pro
```

-continued

```
                    3215                3220                3225

Ser His Gly Trp His Asp Trp Gln Gln Val Pro Phe Cys Ser Asn
    3230                3235                3240

His Phe Gln Glu Ile Val Met Lys Asp Gly Arg Ser Ile Val Val
    3245                3250                3255

Pro Cys Arg Gly Gln Asp Glu Leu Ile Gly Arg Ala Arg Ile Ser
    3260                3265                3270

Pro Gly Ala Gly Trp Asn Val Lys Asp Thr Ala Cys Leu Ala Lys
    3275                3280                3285

Ala Tyr Ala Gln Met Trp Leu Leu Leu Tyr Phe His Arg Arg Asp
    3290                3295                3300

Leu Arg Leu Met Ala Asn Ala Ile Cys Ser Ala Val Pro Val Asp
    3305                3310                3315

Trp Val Pro Thr Gly Arg Thr Ser Trp Ser Ile His Ser Lys Gly
    3320                3325                3330

Glu Trp Met Thr Thr Glu Asp Met Leu Gln Val Trp Asn Arg Val
    3335                3340                3345

Trp Ile Glu Glu Asn Glu Trp Met Val Asp Lys Thr Pro Ile Thr
    3350                3355                3360

Ser Trp Thr Asp Val Pro Tyr Val Gly Lys Arg Glu Asp Ile Trp
    3365                3370                3375

Cys Gly Ser Leu Ile Gly Thr Arg Ser Arg Ala Thr Trp Ala Glu
    3380                3385                3390

Asn Ile Tyr Ala Ala Ile Asn Gln Val Arg Ala Val Ile Gly Lys
    3395                3400                3405

Glu Asn Tyr Val Asp Tyr Met Thr Ser Leu Arg Arg Tyr Glu Asp
    3410                3415                3420

Val Leu Ile Gln Glu Asp Arg Val Ile
    3425                3430

<210> SEQ ID NO 5
<211> LENGTH: 34
<212> TYPE: DNA
<213> ORGANISM: Japanese encephalitis virus

<400> SEQUENCE: 5
agaagtttat ctgtgtgaac ttcttggctt agta                              34

<210> SEQ ID NO 6
<211> LENGTH: 35
<212> TYPE: DNA
<213> ORGANISM: Japanese encephalitis virus

<400> SEQUENCE: 6
gcaaagagaa tgcttttttcc ccatgctttc cagcc                            35

<210> SEQ ID NO 7
<211> LENGTH: 35
<212> TYPE: DNA
<213> ORGANISM: Japanese encephalitis virus

<400> SEQUENCE: 7
tcctgctcaa agagaatgca gtggacctca gtgtg                             35

<210> SEQ ID NO 8
<211> LENGTH: 35
<212> TYPE: DNA
<213> ORGANISM: Japanese encephalitis virus
```

```
<400> SEQUENCE: 8
gtcatgaaga tggctgctgc ctcccctaat tccac                          35

<210> SEQ ID NO 9
<211> LENGTH: 36
<212> TYPE: DNA
<213> ORGANISM: Japanese encephalitis virus

<400> SEQUENCE: 9
actgatgtca ccgaacagag tgcccaacta caacct                         36

<210> SEQ ID NO 10
<211> LENGTH: 35
<212> TYPE: DNA
<213> ORGANISM: Japanese encephalitis virus

<400> SEQUENCE: 10
ttttctataa ccttgggcat gtaagggcag agaac                          35

<210> SEQ ID NO 11
<211> LENGTH: 35
<212> TYPE: DNA
<213> ORGANISM: Japanese encephalitis virus

<400> SEQUENCE: 11
gggaatcctc tccaagtcca gaagtagaag aacaa                          35

<210> SEQ ID NO 12
<211> LENGTH: 34
<212> TYPE: DNA
<213> ORGANISM: Japanese encephalitis virus

<400> SEQUENCE: 12
agatcctgtg ttcttcctca ccaccagcta cata                           34

<210> SEQ ID NO 13
<211> LENGTH: 20
<212> TYPE: DNA
<213> ORGANISM: Japanese encephalitis virus

<400> SEQUENCE: 13
agaagtttat ctgtgtgaac                                           20

<210> SEQ ID NO 14
<211> LENGTH: 20
<212> TYPE: DNA
<213> ORGANISM: Japanese encephalitis virus

<400> SEQUENCE: 14
aaggctcaat catgtggctc                                           20

<210> SEQ ID NO 15
<211> LENGTH: 20
<212> TYPE: DNA
<213> ORGANISM: Japanese encephalitis virus

<400> SEQUENCE: 15
gaaagccaca cggtatctca                                           20

<210> SEQ ID NO 16
<211> LENGTH: 20
<212> TYPE: DNA
<213> ORGANISM: Japanese encephalitis virus
```

```
<400> SEQUENCE: 16
ctgacatctc gacggtggct                                              20

<210> SEQ ID NO 17
<211> LENGTH: 20
<212> TYPE: DNA
<213> ORGANISM: Japanese encephalitis virus

<400> SEQUENCE: 17
tggactgaac actgaagcgt                                              20

<210> SEQ ID NO 18
<211> LENGTH: 20
<212> TYPE: DNA
<213> ORGANISM: Japanese encephalitis virus

<400> SEQUENCE: 18
ttgtcattga actatcctac                                              20

<210> SEQ ID NO 19
<211> LENGTH: 20
<212> TYPE: DNA
<213> ORGANISM: Japanese encephalitis virus

<400> SEQUENCE: 19
gaacactctt tgggggaatg                                              20

<210> SEQ ID NO 20
<211> LENGTH: 20
<212> TYPE: DNA
<213> ORGANISM: Japanese encephalitis virus

<400> SEQUENCE: 20
tgtggaagtg gcatctttgt                                              20

<210> SEQ ID NO 21
<211> LENGTH: 20
<212> TYPE: DNA
<213> ORGANISM: Japanese encephalitis virus

<400> SEQUENCE: 21
tgaacaagcc cgtgggaaga                                              20

<210> SEQ ID NO 22
<211> LENGTH: 20
<212> TYPE: DNA
<213> ORGANISM: Japanese encephalitis virus

<400> SEQUENCE: 22
acttggccag agacacacac                                              20

<210> SEQ ID NO 23
<211> LENGTH: 20
<212> TYPE: DNA
<213> ORGANISM: Japanese encephalitis virus

<400> SEQUENCE: 23
atggtgaaat ggttgaccct                                              20

<210> SEQ ID NO 24
<211> LENGTH: 20
<212> TYPE: DNA
<213> ORGANISM: Japanese encephalitis virus
```

-continued

```
<400> SEQUENCE: 24
agcatggatg attgtccgag                                              20

<210> SEQ ID NO 25
<211> LENGTH: 20
<212> TYPE: DNA
<213> ORGANISM: Japanese encephalitis virus

<400> SEQUENCE: 25
agaaaggagc tgtactcttg                                              20

<210> SEQ ID NO 26
<211> LENGTH: 20
<212> TYPE: DNA
<213> ORGANISM: Japanese encephalitis virus

<400> SEQUENCE: 26
cctacgtggt gtcaggaaaa                                              20

<210> SEQ ID NO 27
<211> LENGTH: 20
<212> TYPE: DNA
<213> ORGANISM: Japanese encephalitis virus

<400> SEQUENCE: 27
ttttccacac actatggcac                                              20

<210> SEQ ID NO 28
<211> LENGTH: 20
<212> TYPE: DNA
<213> ORGANISM: Japanese encephalitis virus

<400> SEQUENCE: 28
gaccgtcagg aggaaccagt                                              20

<210> SEQ ID NO 29
<211> LENGTH: 19
<212> TYPE: DNA
<213> ORGANISM: Japanese encephalitis virus

<400> SEQUENCE: 29
aaggtggaat taggggagg                                               19

<210> SEQ ID NO 30
<211> LENGTH: 19
<212> TYPE: DNA
<213> ORGANISM: Japanese encephalitis virus

<400> SEQUENCE: 30
aagagggaga aggcagagt                                               19

<210> SEQ ID NO 31
<211> LENGTH: 20
<212> TYPE: DNA
<213> ORGANISM: Japanese encephalitis virus

<400> SEQUENCE: 31
atgccatact ggaggacaac                                              20

<210> SEQ ID NO 32
<211> LENGTH: 20
<212> TYPE: DNA
<213> ORGANISM: Japanese encephalitis virus
```

```
<400> SEQUENCE: 32
gaaagggtat agggaagatg                                              20

<210> SEQ ID NO 33
<211> LENGTH: 20
<212> TYPE: DNA
<213> ORGANISM: Japanese encephalitis virus

<400> SEQUENCE: 33
caccacatcg ctagcctcaa                                              20

<210> SEQ ID NO 34
<211> LENGTH: 20
<212> TYPE: DNA
<213> ORGANISM: Japanese encephalitis virus

<400> SEQUENCE: 34
ggtattggtg acggcggcta                                              20

<210> SEQ ID NO 35
<211> LENGTH: 20
<212> TYPE: DNA
<213> ORGANISM: Japanese encephalitis virus

<400> SEQUENCE: 35
tgtgggcgtg gaggatggag                                              20

<210> SEQ ID NO 36
<211> LENGTH: 20
<212> TYPE: DNA
<213> ORGANISM: Japanese encephalitis virus

<400> SEQUENCE: 36
ctagtgcgtc tccccctgtc                                              20

<210> SEQ ID NO 37
<211> LENGTH: 20
<212> TYPE: DNA
<213> ORGANISM: Japanese encephalitis virus

<400> SEQUENCE: 37
ctgacaccac ccctttggga                                              20

<210> SEQ ID NO 38
<211> LENGTH: 19
<212> TYPE: DNA
<213> ORGANISM: Japanese encephalitis virus

<400> SEQUENCE: 38
gctttggggt tcctgaatg                                               19

<210> SEQ ID NO 39
<211> LENGTH: 19
<212> TYPE: DNA
<213> ORGANISM: Japanese encephalitis virus

<400> SEQUENCE: 39
agaagatcaa aggggggagt                                              19

<210> SEQ ID NO 40
<211> LENGTH: 20
<212> TYPE: DNA
<213> ORGANISM: Japanese encephalitis virus
```

```
<400> SEQUENCE: 40
ccgtgcagag gacaggatga                                              20

<210> SEQ ID NO 41
<211> LENGTH: 18
<212> TYPE: DNA
<213> ORGANISM: Japanese encephalitis virus

<400> SEQUENCE: 41
tatgcggcga taaaccag                                                18

<210> SEQ ID NO 42
<211> LENGTH: 18
<212> TYPE: DNA
<213> ORGANISM: Japanese encephalitis virus

<400> SEQUENCE: 42
gcgcagcccc aggaggac                                                18

<210> SEQ ID NO 43
<211> LENGTH: 20
<212> TYPE: DNA
<213> ORGANISM: Japanese encephalitis virus

<400> SEQUENCE: 43
cgtcaatgag tgttccaagt                                              20

<210> SEQ ID NO 44
<211> LENGTH: 20
<212> TYPE: DNA
<213> ORGANISM: Japanese encephalitis virus

<400> SEQUENCE: 44
caatccagta cgacaagtca                                              20

<210> SEQ ID NO 45
<211> LENGTH: 20
<212> TYPE: DNA
<213> ORGANISM: Japanese encephalitis virus

<400> SEQUENCE: 45
tgaccttttt ccccgctctt                                              20

<210> SEQ ID NO 46
<211> LENGTH: 20
<212> TYPE: DNA
<213> ORGANISM: Japanese encephalitis virus

<400> SEQUENCE: 46
ttcttgattt tctcctgatt                                              20

<210> SEQ ID NO 47
<211> LENGTH: 22
<212> TYPE: DNA
<213> ORGANISM: Japanese encephalitis virus

<400> SEQUENCE: 47
agatcctgtg ttcttcctca cc                                           22

<210> SEQ ID NO 48
<211> LENGTH: 62
<212> TYPE: DNA
<213> ORGANISM: Japanese encephalitis virus
```

```
<400> SEQUENCE: 48
aaatttaata cgactcacta taagaagttt atctgtgtga acttcttggc ttagtatcgt      60
tg                                                                   62

<210> SEQ ID NO 49
<211> LENGTH: 45
<212> TYPE: DNA
<213> ORGANISM: Japanese encephalitis virus

<400> SEQUENCE: 49
cgtcatcaaa agcttcccct ggaaattcga caactttatt gctcc                    45

<210> SEQ ID NO 50
<211> LENGTH: 46
<212> TYPE: DNA
<213> ORGANISM: Japanese encephalitis virus

<400> SEQUENCE: 50
cgcaagcttg gcagttgtca tagcttacgc aggagcaata aagttg                   46

<210> SEQ ID NO 51
<211> LENGTH: 45
<212> TYPE: DNA
<213> ORGANISM: Japanese encephalitis virus

<400> SEQUENCE: 51
gctccaatct agtgacagat ctgactccgc acacgccttc cttgt                    45

<210> SEQ ID NO 52
<211> LENGTH: 47
<212> TYPE: DNA
<213> ORGANISM: Japanese encephalitis virus

<400> SEQUENCE: 52
cacaagaaaa gagatgagat gtggaagtgg catctttgtg cacaacg                  47

<210> SEQ ID NO 53
<211> LENGTH: 40
<212> TYPE: DNA
<213> ORGANISM: Japanese encephalitis virus

<400> SEQUENCE: 53
agatcctgtg ttcttcctca ccaccagcta catacttcgg                          40

<210> SEQ ID NO 54
<211> LENGTH: 45
<212> TYPE: DNA
<213> ORGANISM: Japanese encephalitis virus

<400> SEQUENCE: 54
ggtaaatacc acgcgttgac cgttggtact gccaaccatc cagcc                    45

<210> SEQ ID NO 55
<211> LENGTH: 45
<212> TYPE: DNA
<213> ORGANISM: Japanese encephalitis virus

<400> SEQUENCE: 55
ttcctggcgg cgacacttgg ctggatgctt ggcagtacca acggt                    45

<210> SEQ ID NO 56
<211> LENGTH: 46
<212> TYPE: DNA
```

-continued

<213> ORGANISM: Japanese encephalitis virus

<400> SEQUENCE: 56
aagccggagc gaccaacagc aggaggatgg taaataccac gcgttg        46

<210> SEQ ID NO 57
<211> LENGTH: 46
<212> TYPE: DNA
<213> ORGANISM: Japanese encephalitis virus

<400> SEQUENCE: 57
caacgcgtgg tatttaccat cctcctgctg ttggtcgctc cggctt        46

<210> SEQ ID NO 58
<211> LENGTH: 62
<212> TYPE: DNA
<213> ORGANISM: Japanese encephalitis virus

<400> SEQUENCE: 58
aaatttaata cgactcacta taagaagttt atctgtgtga acttcttggc ttagtatcgt        60
tg        62

<210> SEQ ID NO 59
<211> LENGTH: 70
<212> TYPE: DNA
<213> ORGANISM: Artificial
<220> FEATURE:
<223> OTHER INFORMATION: derived from Japanese encephalitis virus and
      West Nile virus

<400> SEQUENCE: 59
ccaagaagtc tctgttgctc attccaaggc agttgaaact gtaagccgga gcgaccagca        60
gcaggaggat        70

<210> SEQ ID NO 60
<211> LENGTH: 70
<212> TYPE: DNA
<213> ORGANISM: Artificial
<220> FEATURE:
<223> OTHER INFORMATION: derived from Japanese encephalitis virus and
      West Nile virus

<400> SEQUENCE: 60
caccatcctc ctgctgctgg tcgctccggc ttacagtttc aactgccttg gaatgagcaa        60
cagagacttc        70

<210> SEQ ID NO 61
<211> LENGTH: 73
<212> TYPE: DNA
<213> ORGANISM: Artificial
<220> FEATURE:
<223> OTHER INFORMATION: derived from Japanese encephalitis virus and
      West Nile virus

<400> SEQUENCE: 61
ctcttttctt gtgatgtcaa tggcacatcc agtgtcagcg tgcacgttca cggagaggaa        60
gagcagaact cct        73

<210> SEQ ID NO 62
<211> LENGTH: 75
<212> TYPE: DNA
<213> ORGANISM: Artificial
<220> FEATURE:
<223> OTHER INFORMATION: derived from Japanese encephalitis virus and

```
                        West Nile virus

<400> SEQUENCE: 62
ggaggagttc tgctcttcct ctccgtgaac gtgcacgctg acactggatg tgccattgac      60
atcacaagaa aagag                                                      75

<210> SEQ ID NO 63
<211> LENGTH: 40
<212> TYPE: DNA
<213> ORGANISM: Japanese encephalitis virus

<400> SEQUENCE: 63
agatcctgtg ttcttcctca ccaccagcta catacttcgg                           40
```